(12) United States Patent
Mintz et al.

(10) Patent No.: US 12,648,783 B2
(45) Date of Patent: \*Jun. 9, 2026

(54) ASPIRATION SYSTEMS AND METHODS, AND EXPANDING-MOUTH CATHETERS

(71) Applicant: Covidien LP, Mansfield, MA (US)

(72) Inventors: Eric Mintz, Newport Beach, CA (US); Ujwal Jalgaonkar, Irvine, CA (US); Emma Hurst, Huntington Beach, CA (US); David P. Marchesiello, Fort Mill, SC (US)

(73) Assignee: Covidien LP, Mansfield, MA (US)

( \* ) Notice: Subject to any disclaimer, the term of this patent is extended or adjusted under 35 U.S.C. 154(b) by 136 days.

This patent is subject to a terminal disclaimer.

(21) Appl. No.: 18/542,171

(22) Filed: Dec. 15, 2023

(65) Prior Publication Data

US 2024/0115277 A1 Apr. 11, 2024

Related U.S. Application Data

(62) Division of application No. 17/008,234, filed on Aug. 31, 2020, now Pat. No. 11,896,250.

(51) Int. Cl.
| | |
|---|---|
| *A61B 17/22* | (2006.01) |
| *A61B 17/00* | (2006.01) |
| *A61B 17/221* | (2006.01) |

(52) U.S. Cl.
CPC ...... *A61B 17/22031* (2013.01); *A61B 17/221* (2013.01); *A61B 2017/00876* (2013.01);
(Continued)

(58) Field of Classification Search
CPC .......... A61M 25/0067; A61M 25/0074; A61M 2025/0079; A61M 2205/0272;
(Continued)

(56) References Cited

U.S. PATENT DOCUMENTS

| | | |
|---|---|---|
| 7,094,243 B2 | 8/2006 | Mulholland et al. |
| 8,366,735 B2 | 2/2013 | Bose et al. |

(Continued)

FOREIGN PATENT DOCUMENTS

EP 3335647 A2 6/2018

OTHER PUBLICATIONS

International Search Report and Written Opinion of International Application No. PCT/US2021/048272, dated Jan. 14, 2022, 17 pp.
(Continued)

*Primary Examiner* — Kankindi Rwego
(74) *Attorney, Agent, or Firm* — Shumaker & Sieffert, P.A.

(57) ABSTRACT

In some examples, a catheter includes an expandable member configured to expand radially outward from a collapsed configuration to an expanded configuration. The expandable member is configured to be expanded and contracted in a controlled manner, e.g., in response to user actuation or automatically under the control of control circuitry of a device. For example, in some examples, control circuitry of a device can be configured to control the expandable member to expand and contract according to a predetermined expansion frequency or according to an expansion frequency determined based on a cardiac cycle of a patient.

16 Claims, 19 Drawing Sheets

(52) U.S. Cl.
CPC ............... *A61B 2017/22079* (2013.01); *A61B 2217/005* (2013.01); *A61M 2205/0272* (2013.01)

(58) Field of Classification Search
CPC ........ A61M 2230/00; A61M 2230/005; A61M 2230/04; A61M 2230/06; A61M 2230/08; A61M 2230/10; A61M 2230/14; A61M 2230/16; A61M 2230/18; A61M 2230/20; A61M 2230/201; A61M 2230/202; A61M 2230/204; A61M 2230/205; A61M 2230/208; A61M 2230/30; A61M 2230/40; A61M 2230/42; A61M 2230/43; A61M 2230/432; A61M 2230/435; A61M 2230/437; A61M 2230/46; A61M 2230/50; A61M 2230/60; A61M 2230/62; A61M 2230/63; A61M 2230/65; A61B 17/22031; A61B 17/221; A61B 17/320725; A61B 2017/00876; A61B 2017/2212; A61B 2017/2215; A61B 2017/2217; A61B 2017/22034; A61B 2017/22035; A61B 2017/22079; A61B 2017/2202; A61B 2017/22001; A61B 2217/005
USPC ......................................................... 606/159
See application file for complete search history.

(56) References Cited

U.S. PATENT DOCUMENTS

| | | | |
|---|---|---|---|
| 10,603,195 B1 | 3/2020 | Sherburne | |
| 11,883,610 B2 | 1/2024 | Mintz et al. | |
| 11,896,250 B2 * | 2/2024 | Mintz | A61M 25/0074 |
| 11,918,241 B2 | 3/2024 | Mintz et al. | |
| 2002/0038125 A1 | 3/2002 | Hamilton | |
| 2002/0165618 A1 | 11/2002 | Ingenito et al. | |
| 2002/0183777 A1 | 12/2002 | Shannon | |
| 2004/0044350 A1 | 3/2004 | Martin et al. | |
| 2010/0222671 A1 | 9/2010 | Cohen et al. | |
| 2010/0263500 A1 | 10/2010 | Bannasch et al. | |
| 2010/0331825 A1 | 12/2010 | Hakky | |
| 2012/0078343 A1 | 3/2012 | Fish | |
| 2012/0116440 A1 | 5/2012 | Leynov | |
| 2012/0143170 A1 | 6/2012 | Hakky | |
| 2013/0144328 A1 | 6/2013 | Weber et al. | |
| 2014/0074144 A1 | 3/2014 | Shrivastava et al. | |
| 2015/0283319 A1 | 10/2015 | Tolkowsky et al. | |
| 2015/0367113 A1 * | 12/2015 | Vollmers | A61M 60/585 |
| | | | 606/194 |
| 2016/0302908 A1 | 10/2016 | Tafti et al. | |
| 2017/0238951 A1 | 8/2017 | Yang et al. | |
| 2017/0311966 A1 | 11/2017 | Ben-Ami | |
| 2018/0064462 A1 | 3/2018 | Walzman | |
| 2019/0298517 A1 | 10/2019 | Sanchez | |
| 2020/0094018 A1 | 3/2020 | Birdno et al. | |
| 2020/0205845 A1 | 7/2020 | Yang et al. | |
| 2020/0249105 A1 | 8/2020 | Fargahi et al. | |
| 2020/0281611 A1 | 9/2020 | Kelly | |
| 2020/0281612 A1 | 9/2020 | Kelly et al. | |
| 2021/0022758 A1 | 1/2021 | Herlinger et al. | |
| 2021/0153884 A1 | 5/2021 | Casey et al. | |
| 2021/0267779 A1 | 9/2021 | Holman et al. | |
| 2021/0331376 A1 | 10/2021 | Preston et al. | |
| 2022/0061870 A1 | 3/2022 | Mintz | |
| 2023/0041152 A1 | 2/2023 | Gifford, III et al. | |

OTHER PUBLICATIONS

Invitation to Pay Additional Fees and, Where Applicable, Protest Fee from International Application No. PCT/US2021/048272, dated Nov. 18, 2012, 10 pp.
Kim et al., "Printing ferromagnetic domains for untethered fast-transforming soft materials," Nature, vol. 558, Jun. 14, 2018, 18 pp.
Prosecution History from U.S. Appl. No. 17/008,113, dated Mar. 18, 2022 through Jan. 8, 2024, 148 pp.
Prosecution History from U.S. Appl. No. 17/008,147, dated May 26, 2023 through Dec. 21, 2023, 39 pp.
Prosecution History from U.S. Appl. No. 17/008,186, dated Nov. 18, 2022 through Nov. 3, 2023, 87 pp.
Prosecution History from U.S. Appl. No. 17/008,234, dated Jul. 7, 2023 through Jan. 10, 2024, 27 pp.
Final Office Action from U.S. Appl. No. 17/008,113 dated Jun. 7, 2024, 15 pp.
Advisory Action from U.S. Appl. No. 17/008,113 dated Aug. 27, 2024, 3 pp.
Response to Final Office Action dated Jun. 7, 2024 from U.S. Appl. No. 17/008,113 filed Aug. 7, 2024, 5 pp.
Response to Office Action dated Jan. 8, 2024 from U.S. Appl. No. 17/008,113 filed Apr. 4, 2024, 9 pp.

* cited by examiner

140 — POSITION STRUCTURAL SUPPORT MEMBER OVER INNER LINER

142 — POSITION EXPANDABLE MEMBER RELATIVE TO INNER LINER AND STRUCTURAL SUPPORT MEMBER

144 — POSITION OUTER JACKET OVER AT LEAST A PORTION OF THE STRUCTURAL SUPPORT MEMBER

150 — INTRODUCE CATHETER INTO VASCULATURE OF PATIENT

152 — DEPLOY EXPANDABLE MEMBER

154 — ASPIRATE THROMBUS

160 — DETERMINE EXPANSION FREQUENCY

162 — CONTROL EXPANSION AND CONTRACTION OF EXPANDABLE MEMBER BASED ON EXPANSION FREQUENCY

ASPIRATION SYSTEMS AND METHODS, AND EXPANDING-MOUTH CATHETERS

This application is a divisional of U.S. patent application Ser. No. 17/008,234, filed Aug. 31, 2020, and entitled, "ASPIRATION SYSTEMS AND METHODS, AND EXPANDING-MOUTH CATHETERS," the entire content of which is incorporated herein by reference.

TECHNICAL FIELD

This disclosure relates to a medical catheter.

BACKGROUND

A medical catheter defining at least one lumen has been proposed for use with various medical procedures. For example, in some cases, a medical catheter may be used to access and treat defects in blood vessels, such as, but not limited to, lesions or occlusions in blood vessels.

SUMMARY

This disclosure describes catheters that include an expandable member configured to expand radially outward from a contracted configuration to an expanded configuration within a vessel of a patient, e.g., to engage a thrombus. For example, the expandable member may include a tubular or cylindrical body configured to radially expand into a larger tubular or cylindrical shape or into a conical shape to more-fully engage a thrombus.

In some examples, the expandable member is configured to be expanded and contracted in a controlled manner, e.g., in response to user actuation or automatically under the control of control circuitry of a device, rather than self-expanding with little to no user intervention. For example, in some examples, the expandable member includes a plurality of tensile-actuated axial prongs and/or a basket comprising struts, and the prongs and/or basket are configured to be expanded radially outward in response to a tensile force applied to one or more pull members mechanically coupled to the prongs or basket. Additionally or alternatively, in some examples, the expandable member may include one or more magnetic elements configured to transition the expandable member between the contracted configuration and the expanded configuration.

This disclosure also describes examples of methods of forming the catheters described herein and methods of using the catheters.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1A:
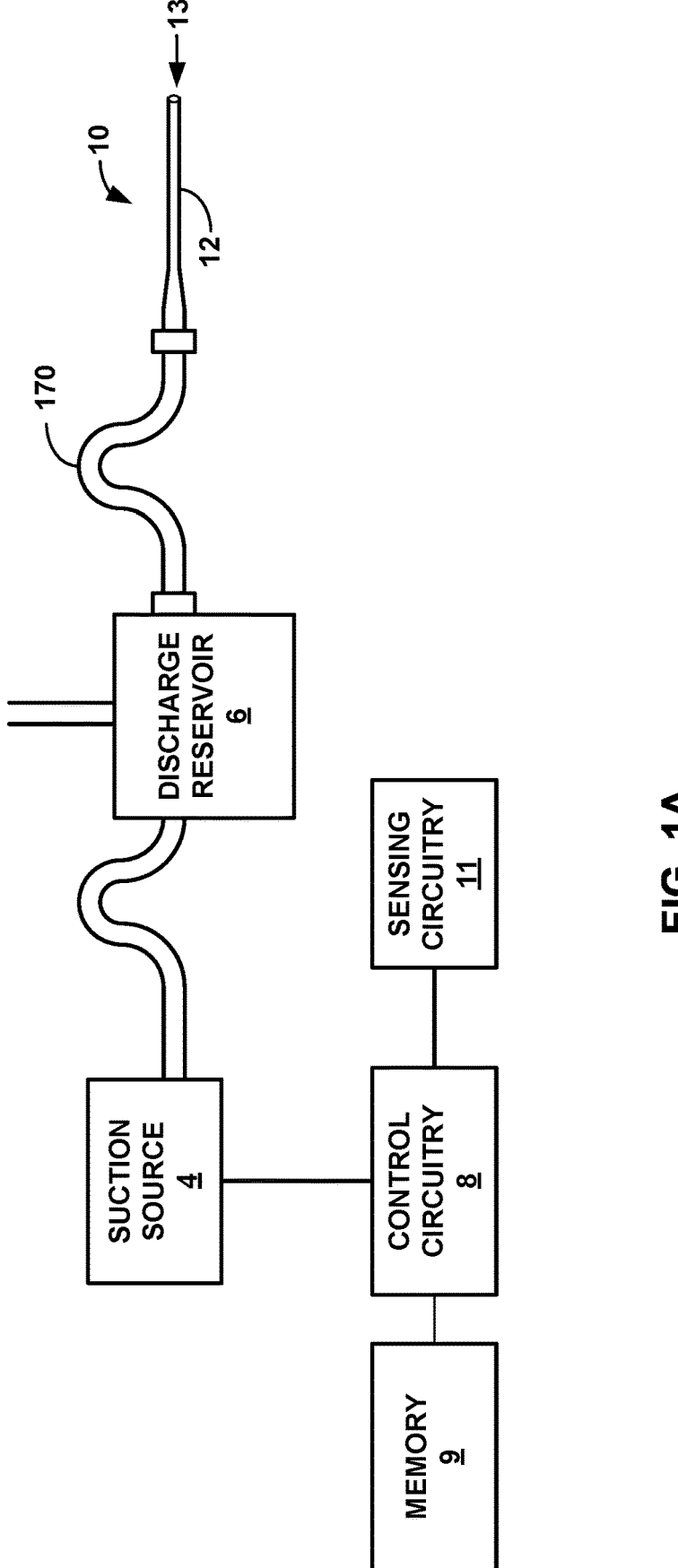
FIG. 1A is a schematic diagram illustrating an example aspiration system including an aspiration catheter.

This disclosure describes catheters and medical aspiration systems (e.g., vascular aspiration systems), as well as methods related to catheters and aspiration systems. FIG. 1A is a schematic diagram illustrating an example aspiration system 2A including a suction source 4, a discharge reservoir 6, control circuitry 8, a memory 9, an aspiration catheter 10, and sensing circuitry 11. Medical aspiration system 2A may be used to treat a variety of conditions, including thrombosis. Thrombosis occurs when a thrombus (e.g., a blood clot or other material such as plaques or foreign bodies) forms and obstructs vasculature of a patient. For example, medical aspiration system 2A may be used to treat an ischemic insult, which may occur due to occlusion of a blood vessel (arterial or venous) that deprives brain tissue, heart tissue or other tissues of oxygen-carrying blood.

Aspiration system 2A is configured to remove fluid via catheter 10, e.g., draw fluid from catheter 10 into discharge reservoir 6, via a suction force applied by suction source 4 to catheter 10 (e.g., to an inner lumen of catheter 10). Catheter 10 includes an elongated body 12 defining a lumen 22 (FIGS. 2A and 2B) terminating in a mouth 13 (also referred to herein as a distal opening). To treat a patient with thrombosis, a clinician may position mouth 13 of catheter 10 in a blood vessel of the patient near the thrombus or other occlusion, and apply a suction force (also referred to herein as suction, vacuum force, or negative pressure) to the catheter 10 (e.g., to one or more lumens of the catheter) to engage the thrombus with suction force at mouth 13 of the catheter. For example, suction source 4 can be configured to create a negative pressure within inner lumen 22 (FIG. 2A) of catheter 10 to draw a fluid, such as blood, an aspiration fluid, more solid material, or a mixture thereof, into inner lumen 22 via mouth 13 of catheter 10. The negative pressure within inner lumen 22 can create a pressure differential between inner lumen 22 and the environment external to at least a distal portion of catheter 10 that causes fluid and other material to be introduced into inner lumen 22 via mouth 13. For example, the fluid may flow from patient vasculature, into inner lumen 22 via mouth 13, and subsequently through aspiration tubing 170 into discharge reservoir 6.

In some examples, aspiration system 2A is also configured to deliver fluid from a fluid source 3 (FIG. 1B), for example, a fluid reservoir different from discharge reservoir 6, through inner lumen 22 of catheter 10 via a positive pressure applied by suction source 4.

As used herein, "suction force" is intended to include within its scope related concepts such as suction pressure, vacuum force, vacuum pressure, negative pressure, fluid flow rate, and the like. A suction force can be generated by a vacuum, e.g. by creating a partial vacuum within a sealed volume fluidically connected to a catheter, or by direct displacement of liquid in a catheter or tubing via (e.g.) a peristaltic pump, or otherwise. Accordingly, suction forces or suction as specified herein can be measured, estimated, computed, etc. without need for direct sensing or measurement of force. A "higher," "greater," or "larger" (or "lower," "lesser," or "smaller") suction force described herein may refer to the absolute value of the negative pressure generated by the suction source on a catheter or another component, such as a discharge reservoir 6.

Figure 1B:
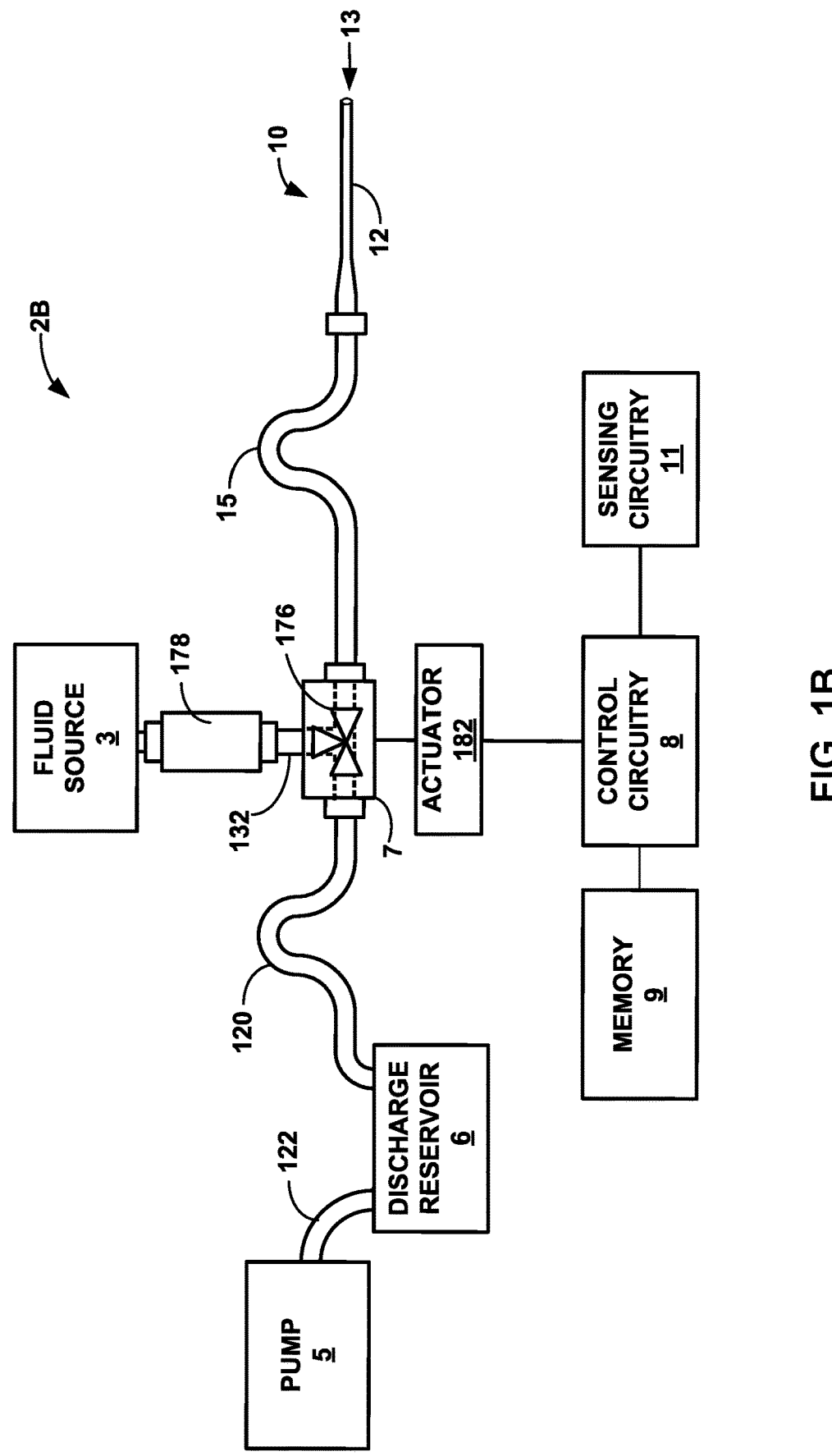
FIG. 1B is a schematic diagram illustrating another example aspiration system including an aspiration catheter.

In some examples, suction source 4 can comprise a pump 5 (FIG. 1B). The suction source 4 can include a direct-acting pump, which acts directly on a liquid to be displaced, or a tube containing the liquid. A direct-displacement pump can comprise a peristaltic pump, or a lobe, vane, gear, or piston pump, or other suitable pumps of this type. A pump can also comprise an indirect-acting pump, which acts indirectly on the liquid to be displaced. An indirect-acting pump can comprise a vacuum pump, which creates a partial vacuum in an evacuation volume fluidically coupled to the liquid to be displaced. The vacuum pump displaces a compressible fluid (e.g., a gas such as air) from the evacuation volume (e.g., discharge reservoir 6, which can comprise a canister), generating suction force on the liquid. Accordingly, the evacuation volume (when present) can be considered part of the suction source. In other examples, suction source 4 can also comprise a pulsator 7, as shown and described with reference to FIG. 1B.

Control, operation, etc. of suction source 4 can comprise control, operation, and the like, of any one or combination of the component(s) making up the suction source. Accordingly, in examples in which suction source 4 includes a pump, evacuation volume, and pulsator, control of the suction source can comprise control of only the pump, of only the evacuation volume, or of only the pulsator, or of any combination of those components. As In examples in which suction source 4 includes only a pump, control of suction source 4 comprises control of the pump. Control of other suction sources may comprise control of only the pulsator, or of only the evacuation volume, or of only the pump, or of any combination of the components which are employed in the suction source.

Once mouth 13 of aspiration catheter 10 has engaged the thrombus, the clinician may remove aspiration catheter 10 with the thrombus held within mouth 13 or attached to the distal tip of elongated body 12, or suction off pieces of the thrombus (or the thrombus as a whole) until the thrombus is removed from the blood vessel of the patient through a lumen of aspiration catheter 10 itself and/or through the lumen of an outer catheter in which aspiration catheter 10 is at least partially positioned. The outer catheter can be, for example, a guide catheter configured to provide additional structural support to the aspiration catheter. The aspiration of the thrombus may be part of an aspiration procedure, such as, but not limited to, a medical procedure using A Direct Aspiration First Pass Technique (ADAPT) for acute stroke thrombectomy, or any other procedure for aspiration of thrombus or other material from the neurovasculature or other blood vessels. In addition, aspiration of thrombus can be performed concurrently with use of a thrombectomy device, such as a stent retriever, to facilitate removal of thrombus via mechanical thrombectomy as well as via aspiration.

Suction source 4 can have any suitable configuration. For example, the pump (as well as pumps generally within the present disclosure) can include one or more of a positive displacement pump (e.g., a peristaltic pump, a rotary pump, a reciprocating pump, or a linear pump), a centrifugal pump, and the like. In some examples, suction source 4 includes a motor driven pump, while in other examples, suction source 4 can include a syringe configured to be controlled by control circuitry 8, and mechanical elements such as linear actuators, stepper motors, etc. As further examples, the suction source 4 could comprise a water aspiration venturi or ejector jet.

In some examples, suction source 4 may be configured for bi-directional operation. For example, suction source 4 may be configured to create a negative pressure that draws fluid from inner lumen 22 of catheter 10 in a first flow direction and create a positive pressure that pumps fluid to catheter 10 and through inner lumen 22 in a second, opposite flow direction. As an example of this bi-directional operation, an operator of aspiration system 2A may operate suction source 4 to pump an aspiration/irrigating fluid, such as saline, from an aspiration fluid reservoir 3 (FIG. 1B) to flush and/or prime catheter 10 (e.g., an infusion state) and subsequently draw fluid from a site of mouth 13 of catheter 10, such as saline and/or blood, into discharge reservoir 6.

Control circuitry 8 is configured to control a suction force applied by suction source 4 to catheter 10. For example, control circuitry 8 can be configured to directly control an operation of suction source 4 to vary the suction force applied by suction source 4 to inner lumen 22, e.g. by controlling the motor speed, or stroke length, volume or frequency, or other operating parameters, of suction source 4. As another example, as described with reference to FIG. 1B, control circuitry 8 can be configured to control a pulsator (e.g., valve) that modifies the suction force applied by suction source 4 to inner lumen 22 of catheter 10. Other techniques for modifying a suction force applied by suction source 4 to inner lumen 22 of catheter 10 can be used in other examples.

Control circuitry 8, as well as other processors, processing circuitry, controllers, control circuitry, and the like, described herein, may include any combination of integrated circuitry, discrete logic circuitry, analog circuitry, such as one or more microprocessors, digital signal processors (DSPs), application specific integrated circuits (ASICs), or field-programmable gate arrays (FPGAs). In some examples, control circuitry 8 may include multiple components, such as any combination of one or more microprocessors, one or more DSPs, one or more ASICs, or one or more FPGAs, as well as other discrete or integrated logic circuitry, and/or analog circuitry.

Memory 9 may store program instructions, such as software, which may include one or more program modules, which are executable by control circuitry 8. When executed by control circuitry 8, such program instructions may cause control circuitry 8 to provide the functionality ascribed to control circuitry 8 herein. The program instructions may be embodied in software and/or firmware. Memory 9, as well as other memories described herein, may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

In some examples, aspiration system 2A includes sensing circuitry 11, which is configured to generate signals (also referred to herein physiological signals) indicative of physiological parameters and communicate the physiological signals to control circuitry 8. Sensing circuitry 11 may include any sensing hardware configured to sense a physiological parameter of a patient, such as, but not limited to, one or more electrodes, optical receivers, pressure sensors, blood pressure cuffs, or the like. In some examples, the sensed physiological signals may include signals indicative of a cardiac cycle of a patient, such as, but not limited to, an electrocardiogram (ECG), an electrogram (EGM), a photoplethysmogram (PPG), or a blood pressure signal. Thus, in some examples, sensing circuitry 11 can be configured to include any suitable hardware configured to sense an electrical cardiac signal, blood pressure, or blood oxygen saturation (e.g., pulse oximetry) of a patient.

In some examples, sensing circuitry 11 and/or control circuitry 8 may include signal processing circuitry configured to perform any suitable analog conditioning of the sensed physiological signals. For example, sensing circuitry 11 may communicate to control circuitry 8 an unaltered (e.g., raw) signal. Control circuitry 8 may be configured to modify a raw signal to a usable signal by, for example, filtering (e.g., low pass, high pass, band pass, notch, or any other suitable filtering), amplifying, performing an operation on the received signal (e.g., taking a derivative, averaging), performing any other suitable signal conditioning (e.g., converting a current signal to a voltage signal), or any combination thereof. In some examples, the conditioned analog signals may be processed by an analog-to-digital converter of control circuitry 8 or other component to convert the conditioned analog signals into digital signals. In some examples, control circuitry 8 may operate on the analog or digital form of the signals to separate out different components of the signals. In some examples, sensing circuitry 11 and/or control circuitry 8 may perform any suitable digital conditioning of the converted digital signals, such as low pass, high pass, band pass, notch, averaging, or any other suitable filtering, amplifying, performing an operation on the signal, performing any other suitable digital conditioning, or any combination thereof. Additionally or alternatively, sensing circuitry 11 may include signal processing circuitry to modify one or more raw signals and communicate to control circuitry 8 one or more modified signals.

In some examples, sensing circuitry 11 includes an ECG sensor, which includes electrodes with which control circuitry 8 may detect an electrical cardiac signal indicative of electrical activity of a heart of a patient. In addition to or instead of the ECG sensor, in some examples, sensing circuitry 11 includes a blood oxygen saturation sensor with which control circuitry 8 can sense blood oxygen saturation levels of a patient and generate an oxygen saturation signal indicative of blood oxygen saturation within the venous, arterial, and/or capillary systems within a region of the patient. For example, sensing circuitry 11 may include a sensor configured to non-invasively generate a PPG signal. One example of such a sensor may be one or more oximetry sensors (e.g., one or more pulse oximetry sensors) configured to be placed at one or multiple locations on a patient, such as at a fingertip of the patient, an earlobe of the patient, and the like.

In addition to or instead of the ECG sensor and/or a blood oxygen saturation sensor, sensing circuitry 11 may include a blood pressure sensor with which control circuitry 8 can sense a blood pressure of a patient and generates a blood pressure signal indicative of the sensed blood pressure. For example, blood pressure sensor may include a continuous noninvasive blood pressure monitor and/or an arterial line configured to invasively (e.g. endoluminally) monitor blood pressure in an artery of the patient. In some examples, the blood pressure signal may include at least a portion of a waveform of the arterial blood pressure.

In addition to or instead of the examples of sensors described above, sensing circuitry 11 can include an acoustic sensor configured to sense heart sounds with which control circuitry 8 or other control circuitry can determine a cardiac cycle of a patient. As one non-limiting example, sensing circuitry 11 may include a transcranial doppler, configured to generate a signal indicative of cranial blood flow rates using ultrasound.

Sensing circuitry 11 can be part of a device that includes control circuitry 8 or device separate from the device that includes control circuitry 8, such as another device co-located with the device that includes control circuitry 8 or remotely located relative to the device that includes control circuitry 8.

In some examples, control circuitry 8 operatively coupled to sensing circuitry 11 and is configured to control an operation of sensing circuitry 11. For example, control circuitry 8 may be configured to provide timing control signals to coordinate operation of sensing circuitry 11. In other examples, control circuitry 8 does not control the operation of sensing circuitry 11.

As discussed with reference to FIG. 16, in some examples, control circuitry 8 is configured to receive one or more signals generated by sensing circuitry 11 and indicative of a cardiac cycle of a patient, and control suction source 4 based on the signals.

FIG. 1B is a schematic diagram of another example aspiration system 2B, which is similar in structure and function to system 2A (FIG. 1A) except as further discussed herein. Aspiration system 2B includes catheter 10, aspiration tubing 15, 120, 122, a suction source which can be implemented in part as a pump 5, and discharge reservoir 6. In addition, aspiration system 2B includes control circuitry 8, memory 9, and sensing circuitry 11. Aspiration system 2B further comprise a pulsator 7 (which can be implemented as valve 176, or otherwise), a flow restrictor 178, a fluid source reservoir 3 connected to pulsator 7 via tubing 132, and an actuator 182.

Pulsator 7 can be employed to switch on, switch off, vary, oscillate, pulse, etc. the application of suction force from a suction source, which is shown as a pump 5 in FIG. 1B, to catheter 10. Accordingly, pulsator 7 can fluidically couple or uncouple catheter 10 to or from pump 5 as needed. For example, pulsator 7 can be configured to open and close the connection of catheter 10 to discharge reservoir 6 (e.g., when no fluid source 3 is present) or alternatingly switch the connection of catheter 10 to discharge reservoir 6 and to fluid source 3.

In the example shown in FIG. 1B, control circuitry 8 is configured to control an amount of suction force applied by pump 5 to inner lumen 22 of catheter 10 by at least controlling pulsator 7 (e.g., controlling a position of valve 176). In some examples, pump 5 is configured to apply a substantially continuous suction force (e.g., continuous or nearly continuous to the extent permitted by the hardware) to discharge reservoir 6, and the amount of this suction force that is transferred to inner lumen 22 of catheter 10 may be adjusted by pulsator 7 (e.g., the position of valve 176). In other examples, pump 5 is configured to apply pulsed aspiration, e.g., by alternating within a repeating cycle between "on" and "off" phases (during the latter of which no suction force, or reduced suction force is applied to tubing 122), rather than applying a substantially continuous suction force. The pulsed aspiration can be used alone or in combination with pulsator 7 to vary the amount of suction force applied to inner lumen 22 of catheter 10, e.g., to aspirate a clot from vasculature of a patient.

Pulsator 7 can have any suitable configuration, such as, but not limited to, a valve, tubing clamp, tubing pincher, fluid switch, or the like, configured for selective actuation as needed to fluidically couple or uncouple catheter 10 to or from pump 5 in accordance with control of aspiration system 2B. In the example shown in FIG. 1B, pulsator 7 includes a valve 176, which is movable between at least a first position and a second position. For example, valve 176 can be a two-position three-way valve, such as a three-way ball valve or another suitable valve, e.g., a pinch, poppet, diaphragm, butterfly, slide, or piston valve. Another suitable valve type is a 1-way or 2-way valve equipped with a relief vent (in which case the fluid source 3 can be omitted along with flow restrictor 178 and the connection to the valve 176). In the first position, valve 176 fluidically couples catheter 10 and fluid source reservoir 3, and catheter 10 and pump 5 are not fluidically coupled. Thus, in the first position of valve 176, pump 5 does not apply a suction force to inner lumen 22 of catheter 10 and does not draw fluid from inner lumen 22 into discharge reservoir 6. Fluid source reservoir 3 can store an incompressible fluid, such as saline; alternatively, it can be a source of compressible fluid such as a vent to ambient air via tubing 132. Fluid source reservoir 3, when present, can be vented to an external environment.

When valve 176 is in its first position, fluid source reservoir 3 is fluidically coupled to inner lumen 22 of catheter 10, thereby relieving any negative pressure in catheter 10 or tubing 15, or otherwise allowing catheter 10 and tubing 15 to equalize with ambient pressure or a desired baseline pressure. In addition, when valve 176 is in its first position, pump 5 is configured to apply a negative pressure to tubing 122, which creates and/or maintains a negative pressure in discharge reservoir 6. Control circuitry 8 or a clinician can adjust a setting of flow restrictor 178 (when present) in order to adjust a rate of fluid flow from fluid source reservoir 3 to catheter 10 and/or tubing 15 when valve 176 is in its first position (and intermediary positions, as discussed in further detail below).

In the second position of valve 176, valve 176 fluidically couples pump 5 and inner lumen 22 of catheter 10, and discharge reservoir 6 and fluid source reservoir 3 are not fluidically coupled to each other. Thus, in the second position of valve 176, pump 5 (via discharge reservoir 6) can apply a suction force to inner lumen 22 of catheter 10 and draw fluid from inner lumen 22 into discharge reservoir 6.

In some examples, valve 176 is also configured to assume positions between the first and second positions. In such intermediary positions, valve 176 is configured to permit some fluid flow from fluid source reservoir 3 to catheter 10 (the fluid flow being less than that observed when valve 176 is in its first position) and, at the same time, to permit some fluid flow from the inner lumen of catheter 10 to discharge reservoir 6 (the fluid flow being less than that observed when valve 176 is in its second position).

In addition, in some examples, fluid source reservoir 3 can be omitted along with flow restrictor 178 and the connection to the valve 176, which can take the form of a conventional two-way valve rather than the three-way valve depicted in FIG. 1B.

Control circuitry 8 is configured to control a position of valve 176 in order to control an amount of suction force applied by pump 5 to inner lumen 22 of catheter 10 using any suitable technique. In the example shown in FIG. 1B, valve 176 is configured to be actuated between the first and second positions, including any intermediary positions, based on an amount of current applied (and/or signal(s) passed) to actuator 182. In some examples, actuator 182 can comprise a solenoid; in such examples, valve 176 can be referred to as a solenoid valve. Actuator 182 can alternatively comprise a linear or rotary actuator, servo, stepper motor, piezoelectric element(s), etc., or any other suitable component(s), or any combination of the foregoing. Control circuitry 8 can control an amount of current applied to (and/or pass signal(s) to) actuator 182 in order to modify a position of valve 176.

As detailed further below, in some examples, control circuitry 8 is configured to control pulsator 7 (e.g., a position of valve 176) to modify a suction force applied by pump 5 to lumen 22 of catheter 10 based on a particular timing, which can be referred to as suction frequency. The suction frequency can be a fixed frequency over a period of time or can vary over the period of time.

In other examples, pulsator 7 employed in the system 2B of FIG. 1B can comprise one or more pinch valves. For example, a first pinch valve can be operatively coupled to tubing 120 and a second pinch valve can be operatively coupled to tubing 132. Control circuitry 8 can be configured to control such pinch valves to open and close tubing 120 and tubing 132 at appropriate times in accordance with the control techniques disclosed herein. In a first position of pulsator 7, the first pinch valve is open and the second pinch valve is closed, and in a second position of pulsator 7, the first pinch valve is closed and the second pinch valve is open. Tubing 132 can be connected to fluid source reservoir 3, with or without flow restrictor 178, or tubing 132 can terminate in an opening to ambient air. A check valve can be operatively coupled to tubing 132 on the side of the second pinch valve opposite the connection to tubing 120. The first and second pinch valves can be implemented with a common actuator forming a dual-acting pinch valve that alternatingly opens and closes the first and second pinch valves.

Figure 2A:
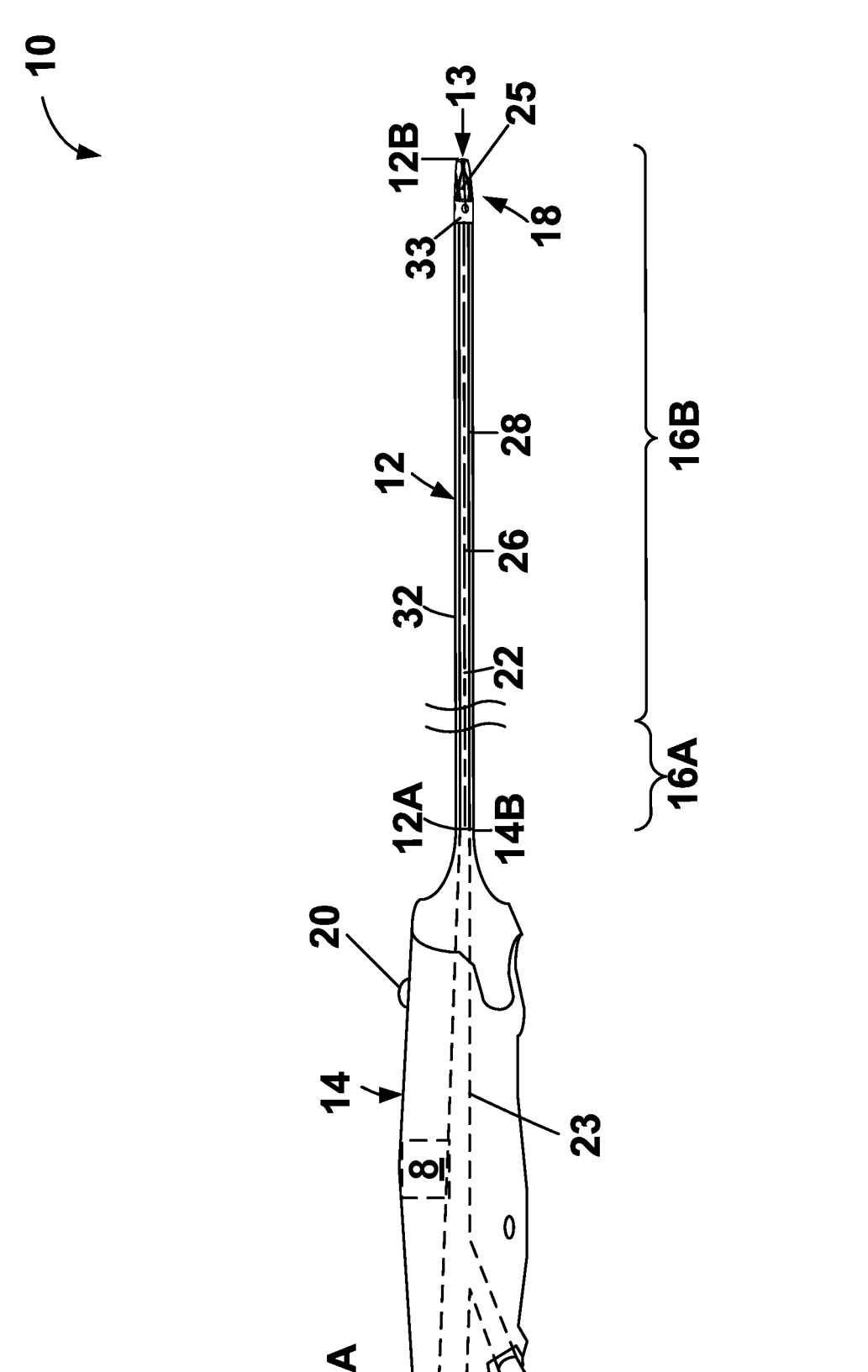
FIG. 2A is a conceptual side view of an example of the aspiration catheter of FIGS. 1A and 1B, which includes an elongated body and an expandable member at a distal portion of the elongated body.
Figure 2B:
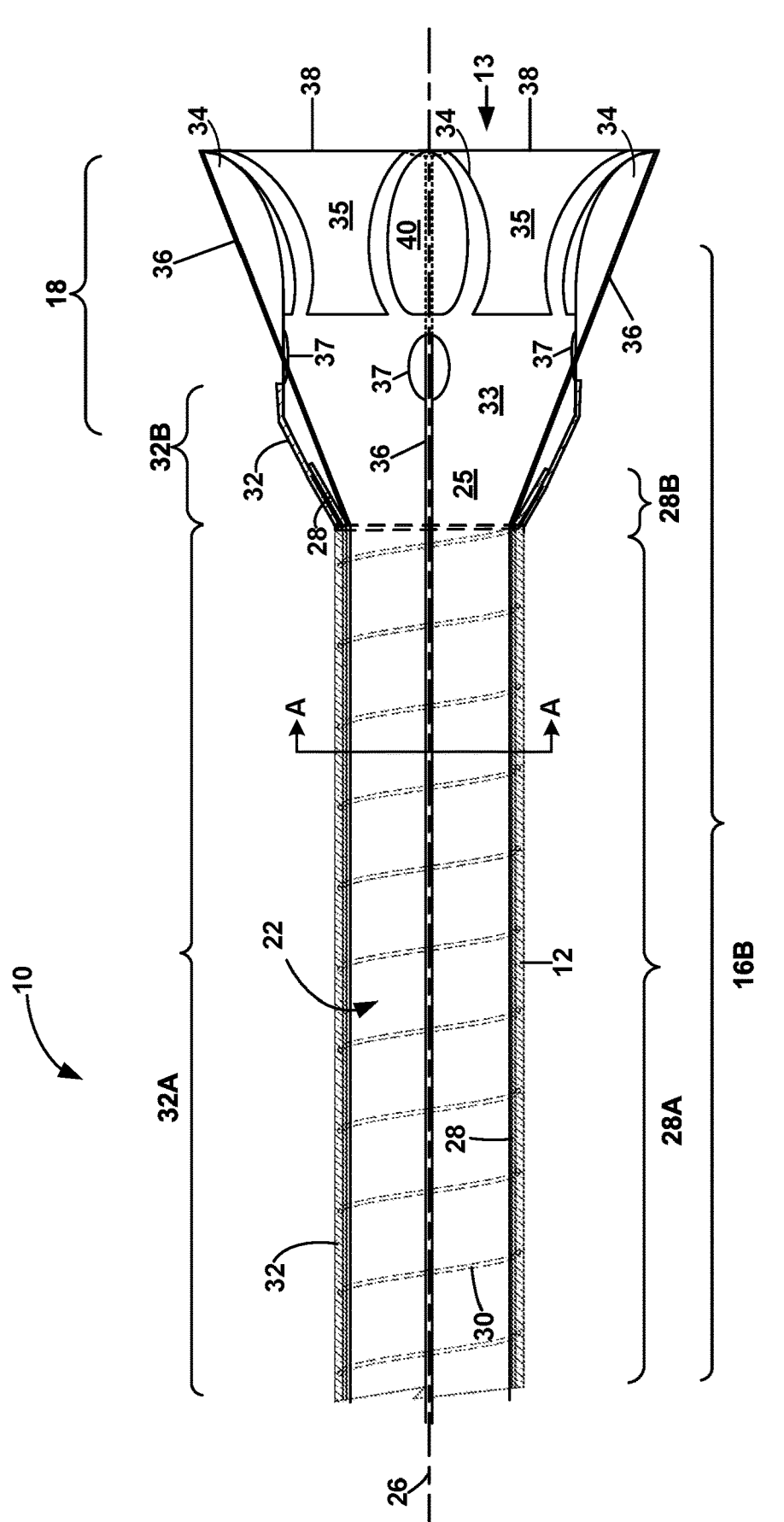
FIG. 2B is a conceptual cross-sectional view of the distal portion of the elongated body of FIG. 2A, where the cross-section is taken through a center of the elongated body and along a longitudinal axis.

FIGS. 2A and 2B illustrate an example of aspiration catheter 10 of FIGS. 1A and 1B, which includes elongated body 12, a handle 14 proximal to elongated body 12, and expandable member 18 at a distal portion 16B of the elongated body 12. As shown in FIG. 2A, catheter 10 includes a relatively flexible elongated body 12 configured to be navigated through vasculature of a patient, e.g., tortuous vasculature in a brain of the patient. In examples described herein, a distal portion 16B of elongated body 12 includes an expandable member 18, such as an expandable funnel, an expandable tubular shape configured to radially expand into a larger tubular shape, or other expandable structure, configured to expand radially outward within a vessel of the patient. This may enable, for example, expandable member 18 to engage with a clot (e.g., thrombus or embolism) during an aspiration procedure.

Expandable member 18 may help improve aspiration of the clot into the catheter 10 by providing a relatively large diameter (or other cross-sectional dimension) and interior space for the clot to engage with the elongated body compared to examples in which an otherwise similar catheter does not include an expandable member. For example, such a catheter that does not include an expandable member may have more limited (or no) radial expansion capability, and may thus make it harder to aspirate a clot (e.g., due to a smaller cross-sectional dimension of the distal end of the catheter). Expandable member 18 may overcome such radial expansion limitations, including by increasing clot engagement, reducing the amount of time required for revascularization, and increase revascularization success rates for various procedures, as compared to similar procedures used with catheters that do not include an expandable member to engage a clot. For example, expandable member 18 may be configured to radially expand along part (e.g., over 50%) or all of its axial length, forming an enlarged tubular or cylindrical shape, so as to largely envelop a clot within the vasculature. An expandable member 18 that is configured to assume a tubular or cylindrical shape in an expanded configuration, as opposed to a more conical shape, may enable a length of the expanded distal portion of catheter 10 to be increased, which can enable expandable member 18 to envelop more thrombus material. This can further contribute to the overall clot engagement and reduce an amount of time required for revascularization.

In some examples, expandable member 18 includes one or more structural features that enable the expandable member to convert between a contracted configuration and an expanded configuration. For example, expandable member 18 may include any or all of a set of tensile-actuated axial prongs, a basket having circumferential expansion struts, and/or one or more magnetic elements configured to transition the expandable member between the contracted configuration and the expanded configuration. In the contracted configuration, expandable member 18 has a lower profile than in the expanded configuration. To transition from the contracted configuration (also referred to herein as a contracted state, a collapsed configuration or state, or a compressed configuration or state), expandable member 18 expands radially outward away from central longitudinal axis 26 of elongated body 12. In some examples, a control unit, such as control circuitry 8 of FIGS. 1A and 1B, may cause expandable member 18 to expand and contract, such as in a cyclic or periodic manner.

Elongated body 12 is configured to be advanced through vasculature of a patient via a pushing force applied to proximal portion 16A (e.g., via handle 14) of elongated body 12, e.g., while resisting undesirable deformation such as buckling or kinking. In some examples, elongated body 12 includes an inner liner 28, an outer jacket 32, and a structural support member 30 (FIG. 2B) positioned between at least a portion of the inner liner 28 and at least a portion of the outer jacket 32. At distal portion 16B, elongated body 12 includes an expandable member 18 configured to radially expand within a vessel of a patient, e.g., to engage a clot within the vessel.

Elongated body 12 extends from proximal end 12A to distal end 12B and defines at least one inner lumen 22. In the example shown in FIG. 2A, proximal end 12A of elongated body 12 is mechanically connected to handle 14 via an adhesive, welding, or another suitable technique or combination of techniques. Handle 14 may define an inner lumen 23 (referred to herein as a "handle lumen") in fluid communication with inner lumen 22 of elongated body 12. Catheter 10 may be used as an aspiration catheter to remove a clot or other material such as plaques or foreign bodies from vasculature of a patient. In such examples, a suction force may be applied to a handle lumen 23, e.g., at proximal end 14A of handle 14 (e.g., via side port 24), to draw a clot or other blockage into inner lumen 22 of elongated body 12 via mouth 13 (e.g., a distal-most opening) of catheter 10. An aspiration catheter may be used in various medical procedures, such as a medical procedure to treat an ischemic insult, which may occur due to occlusion of a blood vessel (arterial or venous) that deprives brain tissue, heart tissue or other tissues of oxygen-carrying blood.

Catheter 10 is configured to be navigated to any suitable vasculature site in a patient. In some examples, catheter 10 is configured to access relatively distal locations in a patient including, for example, the middle cerebral artery (MCA), internal carotid artery (ICA), the Circle of Willis, and tissue sites more distal than the MCA, ICA, and the Circle of Willis. The MCA, as well as other vasculature in the brain or other relatively distal tissue sites (e.g., relative to the vascular access point), may be relatively difficult to reach with a catheter, due at least in part to the tortuous pathway (e.g., comprising relatively sharp twists or turns) through the vasculature to reach these tissue sites. Elongated body 12 may be structurally configured to be relatively flexible, pushable, and relatively kink- and buckle-resistant, so that it may resist buckling when a pushing force is applied to a relatively proximal section of catheter 10 (e.g., via handle 14) to advance elongated body 12 distally through vasculature, and so that it may resist kinking when traversing around a tight turn in the vasculature. In some examples, elongated body 12 is configured to substantially conform to the curvature of the vasculature. In addition, in some examples, elongated body 12 has a column strength and flexibility that allow at least distal portion 16B of elongated body 12 to be navigated from a femoral artery, through the aorta of the patient, and into the intracranial vascular system of the patient, e.g., to reach a relatively distal treatment site. Alternatively, the elongated body can have a column strength (and/or be otherwise configured) to enable the distal portion 16B of elongated body 12 to be navigated from a radial artery via an access site in the arm, e.g. at or near the wrist, through the aorta of the patient or otherwise to a common carotid or vertebral artery, and into the intracranial vascular system of the patient, e.g., to reach a relatively distal treatment site.

Although primarily described as being used to reach relatively distal vasculature sites, catheter 10 may also be configured to be used with other target tissue sites. For example, catheter 10 may be used to access tissue sites throughout the coronary and peripheral vasculature, the gastrointestinal tract, the urethra, ureters, fallopian tubes, veins and other body lumens.

A length of catheter 10 may depend on the location of the target tissue site within the body of a patient or may depend on the medical procedure for which catheter 10 is used. In some examples, catheter 10 may be described in terms of the working length of elongated body 12. The working length of elongated body 12 may be measured from distal end 14B of handle 14 to distal end 12B of elongated body 12 along a central longitudinal axis 26 of elongated body 12. For example, if catheter 10 is a distal-access catheter used to access vasculature in a brain of a patient from a femoral artery access point at the groin of the patient, then elongated body 12 may have a working length of about 115 centimeters (cm) to about 145 cm or more, such as about 130 cm, although other lengths may be used (e.g., in the case of a radial access catheter). Distal portion 16B may be about 5 cm to about 35 cm in length. The length of distal portion 16B may include the length of expandable member 18. Proximal portion 16A may be about 90 cm to about 130 cm in length, depending on the length of distal portion 16B.

Handle 14 may be positioned at a proximal portion 16A of elongated body 12. Handle 14 may define the proximal end 14A of catheter 10. In some examples, handle 14 may include a luer connector, a hemostasis valve, or another mechanism or combination of mechanisms for connecting to another device such as suction source 4 (FIG. 1A) for performing the aspiration techniques described herein. For example, suction source 4 may be fluidically connected to side port 24 of handle 14. In some examples, proximal end 14A of catheter 10 can include another structure in addition to, or instead of, handle 14, such as a catheter hub.

In some cases, a clinician may steer catheter 10 through the vasculature of a patient by pushing or rotating handle 14 and/or proximal portion 16A of catheter 10 to navigate distal portion 16B of elongated body 12 through the vasculature of a patient. The clinician may apply torque to handle 14 and/or proximal portion 16A of the catheter 10 (or at least a portion of elongated body 12 that is more proximal than distal portion 16B implanted in the patient) in order to rotate distal portion 16B of catheter 10.

In some examples, an inner liner 28 of elongated body 12 defines at least a portion of inner lumen 22 of elongated body 12, inner lumen 22 defining a passageway through elongated body 12. As discussed in further detail below, expandable member 18 may also define an inner lumen 25 that is fluid communication with inner lumen 22 of elongated body 12. In the example shown in FIG. 2B, inner lumen 25 defined by expandable member 18 distally terminates at a distal-most end of catheter 10. In some examples, inner lumen 22 may extend over the entire length of inner liner 28 (e.g., from a proximal end to a distal end of the inner liner 28). Inner lumen 22 may be sized to receive a medical device (e.g., another catheter, a guidewire, an embolic protection device, a stent, a thrombectomy device, such as a stent retriever, or any combination thereof), a therapeutic agent, or the like. Inner liner 28 may define a single inner lumen 22, or multiple inner lumens (e.g., two inner lumens or three inner lumens) of catheter 10.

Inner lumen 22 formed by inner liner 28 may define the inner diameter of elongated body 12. Although a diameter is primarily referred to as a dimension of the inner lumen 22 and an elongated body 12 having a circular cross-section (in a direction orthogonal to a longitudinal axis 26 (FIG. 2B) of elongated body 12) is primarily referred to herein, in other examples, elongated body 12 and inner lumen 22 can have other cross-sectional shapes, such as, but not limited to, oval shapes, rectangular shapes, spade shapes, and other non-circular shapes.

The diameter of inner lumen 22 (as measured in a direction perpendicular to longitudinal axis 26 (FIG. 2B) of elongated body 12) may vary based on the one or more procedures with which catheter 10 may be used. In some examples, the diameter of inner lumen 22 of elongated body 12, also referred to herein as an inner diameter of elongated body 12 or inner liner 28, may be substantially constant (e.g., constant or nearly constant) from proximal end 12A to the proximal end of expandable member 18 (e.g., substantially constant apart from the diameter change associated with expandable member 18). In some examples, the inner diameter may be about 1.524 mm (about 0.060 inches) or larger. In other examples, the inner diameter may not be constant. For example, the inner diameter of elongated body 12 may taper from a first inner diameter at proximal end 12A to a second, smaller inner diameter at a more distal section just proximal to expandable member 18. For example, an inner diameter of elongated body 12 may taper from a first inner diameter of about 0.0685 inches (about 1.74 mm) to a second inner diameter of about to 0.0605 inches (about 1.54 mm) The inner diameter may, for example, gradually taper in the direction along longitudinal axis 26, where the taper can be linear, curved, continuous, or discontinuous, e.g., the inner diameter of inner liner 28 may step-down from the first inner diameter to the second inner diameter in discrete steps. For example, expandable member 18 may define a tapered distal tip of the elongated body 12. As described further below, the inner diameter of the section of elongated body 12 that includes expandable member 18 may be larger than the inner diameter of elongated body 12 within regions proximal to expandable member 18.

An expandable member 18 that defines a tapered tip in a contracted configuration may help center distal portion 16B of elongated body 12 around a guidewire or other guide member in lumen 22 of elongated body 12, which may help prevent or reduce the occurrence of a catheter ledge-effect and improve the ease with which a clinician may guide the catheter to a relatively distal vasculature treatment site through a series of tight turns in the vasculature. A ledge-effect may otherwise cause distal end 12B of elongated body 12 to catch on or abrade certain anatomical features as it is advanced through vasculature of the patient, which may adversely affect the navigability of the catheter. In contrast to catheters without expandable members at their distal ends, expandable member 18 may enable catheter 10 to maintain a lower profile during navigation to a target site within vasculature of a patient without compromising the size of the inner diameter (or other dimension if non-circular in cross-section) of mouth 13 during aspiration.

Inner liner 28 may be formed using any suitable material, such as, but not limited to, polytetrafluoroethylene (PTFE), expanded PTFE (ePTFE, e.g., unidirectional ePTFE or bi-directional ePTFE), a fluoropolymer, perfluoroalkyoxy alkane (PFA), fluorinated ethylene propylene (FEP), poly-olefin elastomers or any combination thereof. A unidirectional ePTFE may be stretched in one of the longitudinal or radial directions, and a bi-directional ePTFE may be stretched in both the longitudinal and radial directions. Other examples of materials from which inner liner 28 may be formed include, but are not limited to, Low Density Polyethylene (LDPE) (e.g., about 42D), a PTFE having a durometer of about 60D, High Density Polyethylene (HDPE), or any combination thereof. Some such polyolefin materials may have similar coefficients of friction as PTFE, and may be conducive to processing. In some examples, inner liner 28 may include PTFE, which may provide elongated body 12 with a lubricious inner surface and allow relatively easy delivery of interventional devices through the elongated body, removal of a clot, or relatively easy tracking of the elongated body over a guide member (e.g., a guidewire or a microcatheter). In some cases, a PTFE inner liner 28 may impart stiffness to elongated body 12 to improve various navigation properties such as the pushability catheter 10 through vasculature of the patient.

Elongated body 12 includes one or more structural support members 30 positioned over inner liner 28. Structural support member 30 is configured to increase the structural integrity of elongated body 12 while allowing elongated body 12 to remain relatively flexible. For example, structural support member 30 may be configured to help elongated body 12 substantially maintain its cross-sectional shape (e.g., circular or nearly circular) or at least help prevent elongated body 12 from buckling or kinking as it is navigated through tortuous anatomy. Additionally, or alternatively, structural support member 30, together with inner liner 28, and outer jacket 32, may help distribute both pushing and rotational forces along a length of elongated body 12, which may help prevent kinking of elongated body 12 upon rotation of body 12 or help prevent buckling of body 12 upon application of a pushing force to body 12. As a result, a clinician may apply pushing forces, rotational forces, or both, to the proximal portion of elongated body 12, and such forces may cause a distal portion of elongated body 12 to advance distally, rotate, or both, respectively.

Structural support member 30 may include one or more tubular braided structures, one or more coil members defining a plurality of turns, e.g., in the shape of a helix, or a combination of a braided structure and a coil member. Thus, although the examples of the disclosure primarily describe structural support member 30 as a coil, in other examples, catheter 10 may include a braided structure instead of a coil, a braided structure in addition to a coil, or a combination that includes one or more of each structure. As one example, a proximal portion of structural support member 30 may include a braided structure and a distal portion of structural support member 30 may include a coil member. In some examples, a braided wire (e.g., a combination of round wires and flat wires) may provide elongated body 12 with better ovalization resistance and tensile strength compared to other catheter designs (e.g., a support element consisting of only one metal coil or a braid consisting of only round wires) and coil structures (e.g., wire coils) may exhibit better columnar strength (e.g., kink resistance) and/or hoop strength (e.g., resistance to ovalization) compared to other catheter designs.

Structural support member 30 can be made from any suitable material, such as, but not limited to, a metal (e.g., a nickel titanium alloy (Nitinol), stainless steel, tungsten, titanium, gold, platinum, palladium, tantalum, silver, or a nickel-chromium alloy, a cobalt-chromium alloy, or the like), a polymer, a fiber, or any combination thereof. In some examples, structural support member 30 may include one or more metal wires braided or coiled around inner liner 28. The metal wires may include round wires, flat-round wires, flat wires, or any combination thereof.

In other examples, structural support member 30 may include a spiral cut hypotube that is expanded and positioned over inner liner 28. As described further below, in some such examples, structural support member 30 may be formed integrally with expandable member 18. For example, struc-tural support member 30 and expandable member 18 may be laser-cut from the same hypotube, e.g., structural support member 30 representing a spiral cut segment of the hypotube and expandable member 18 representing a segment cut from the hypotube according to one of the examples detailed further below.

In some examples, structural support member 30 is positioned proximal to expandable member 18. In some examples, the distal end of structural support member 30 may abut the proximal end of expandable member 18 and may be coupled to expandable member 18 (e.g., mechanically coupled or bonded with adhesive, or welded). In other examples, expandable member 18 may not be coupled to structural support member 30 or may not be in direct contact (e.g., abutting contact) with structural support member 30, although the two members may be in the same radial layer of elongated body 12. For example, the distal end of structural support member 30 may be adjacent to the proximal end of expandable member 18 but separated by a relatively small gap. In such examples, structural support member 30 and expandable member 18 may be in the same radial layer and inner liner 28, outer jacket 32, or both may secure both expandable member 18 and structural support member 30 in place along elongated body 12.

Elongated body 12 also includes outer jacket 32 positioned over structural support member 30 and inner liner 28, the structural support member 30 being positioned between portions of inner liner 28 and outer jacket 32. In some examples, outer jacket 32 may be positioned around structural support member 30 such that outer jacket 32 covers at least a part or all of both inner liner 28 and structural support member 30. Outer jacket 32, together with inner liner 28 and structural support member 30, may be configured to define elongated body 12 having the desired structural characteristics (e.g., flexibility, kink resistance, torque responsiveness, structural integrity, pushability, and column strength, which may be a measure of a maximum compressive load that can be applied to elongated body 12 without taking a permanent set). For example, outer jacket 32 may have stiffness characteristics that contribute to the desired stiffness profile of elongated body 12. In some examples in which outer jacket 32 extends over expandable member 18, outer jacket 32 is configured to accommodate radial expansion of expandable member 18.

Additionally, or alternatively, outer jacket 32 may define a durometer gradient (e.g., hardness) along longitudinal axis 26. For example, outer jacket 32 may be defined by a plurality of tubular segments extending from proximal end 12A toward distal end 12B wherein each tubular segment defines a different durometer. The durometer gradient of outer jacket 32 may be selected to help provide elongated body 12 with the desired flexibility characteristics. For example, in some examples in which elongated body 12 increases in flexibility from proximal end 12A towards distal end 12B, the durometer gradient of outer jacket 32 may decrease in a direction from proximal end 12A towards distal end 12B. In some examples, the durometer of outer jacket 32 may be from about 25D to about 75D. For example, outer jacket 32 may define a durometer gradient from proximal end 12A towards distal end 12B that generally decreases from about 75D to about 25D.

In some examples, outer jacket 32 may be formed using any suitable material including, but are not limited to, polymers, such as a polyether block amide (e.g., PEBAX®, commercially available from Arkema Group of Colombes, France), an aliphatic polyamide (e.g., Grilamid®, commercially available from EMS-Chemie of Sumter, South Carolina), another thermoplastic elastomer (e.g., a thermoplastic, elastomeric polymer configured to accommodate radial expansion of expandable member 18), polyurethanes, polyamides, or other thermoplastic material, or combinations thereof. In some examples, outer jacket 32 may be formed of an elastic material, such as polyolefin thermoplastic elastomers, polyurethane elastomeric alloys or silicone, that permits the expansion of expandable member 18. For example, distal section 32B of outer jacket 32 extending at least partially coextensive with expandable member 18 may be formed with such elastic material.

Outer jacket 32 may be heat shrunk around structural support member 30 and, in some examples, at least a portion (e.g., a proximal portion) of expandable member 18 to secure the two members in the same radial layer. In some examples, during the heat shrinking of outer jacket 32 around structural support member 30, the material of outer jacket 32 may flow into at least some of the inner spacings or gaps (e.g., gaps between the adjacent turns of the coils, or between the struts or braids) within structural support member 30 or expandable member 18 such that portions of outer jacket 32 and structural support member 30 or expandable member 18 form a pseudo-coextensive layer.

In some examples, distal section 32B of outer jacket 32 is co-axial with expandable member 18 and is at least partially coextensive with expandable member 18. In some such examples, as shown in FIG. 2B, distal section 32B of outer jacket 32 may terminate prior to the distal end of expandable member 18, such that expandable member 18 extends distally past a distal end of outer jacket 32 and distal section 32B is only partially coextensive with expandable member 18. In other examples, outer jacket 32 is not coextensive with expandable member and instead terminates prior to the proximal end of expandable member 18 such that there is no overlap between expandable member 18 and outer jacket 32. In other examples, however, distal section 32B of outer jacket 32 may be fully coextensive with expandable member 18 and cover the entire outer surface of expandable member 18.

Although a coating or another material may be applied over the outer surface of outer jacket 32, outer jacket 32 may still substantially define shape and size of the outer surface of elongated body 12. In some examples, the outer diameter of elongated body 12 may be substantially constant (e.g., constant or nearly constant) along the length of elongated body 12, excluding the change in diameter created by expandable member 18. In other examples, the outer diameter of elongated body 12 may taper from the first outer diameter within proximal portion 16A of elongated body 12 to a second outer diameter at point proximate to the proximal end of expandable member 18 (e.g., at point where expandable member 18 is coupled to or positioned next to structural support member 30), and the outer diameter may increase from the referenced point to a third outer diameter of the section of elongated body 12 where expandable member 18 is positioned.

In some examples, the taper of the outer diameter of elongated body 12 (e.g., from the first diameter to the second diameter or from the second diameter to the third diameter) may be continuous along the length of elongated body 12, such that an outer surface of elongated body 12 defines a smooth transition between different diameter portions. In other examples, elongated body 12 may define discrete step-downs in outer diameter to define the taper. The size of the discrete step-downs in diameter may be selected to reduce the number of edges that may catch on anatomical features within the vasculature as elongated body 12 is advanced through vasculature.

A larger-diameter proximal portion of elongated body 12 may provide better proximal support for elongated body 12, which may help improve the pushability of elongated body 12. In addition, a generally smaller diameter within the distal portion (e.g., excluding the diameter of expandable member 18) may increase the navigability of elongated body 12 through tortuous vasculature. Thus, by reducing the outer diameter of elongated body 12 from proximal portion 16A to distal portion 16B, elongated body 12 may better traverse through tortuous vasculature while still maintaining a relatively high level of proximal pushability. In some examples, such as when expandable member 18 is in a contracted configuration, the outer diameter at distal end 12B may be the same or smaller than the second outer diameter proximal to distal end 12B. In some examples, the outer diameter(s) of elongated body 12 is in a range of about 3 French to about 10 French, such as about 3 French to about 6 French. The measurement term "French," abbreviated Fr or F, is three times the diameter of a device as measured in mm. For example, a 6 French diameter is about 2 mm.

Expandable member 18 is positioned at distal portion 16B of elongated body 12, such that a distal end of expandable member 18 defines distal end 12B of elongated body 12. Expandable member 18 is configured to provide a radially expandable mouth 13 at distal end 12B with a relatively large diameter (compared to, for example, proximal portion 16A of elongated body 12) and interior space for better engagement with a clot (e.g., thrombus or embolus). For example, expandable member 18 may be an expandable tube or funnel. In some examples, catheter 10 may be used with an aspiration procedure (e.g., ADAPT technique) and the size and shape of expandable member 18 may enable elongated body 12 to better engage a clot by increasing the opening into which the clot may be received, and/or by distributing the aspiration forces over a greater portion of the clot rather than a localized area, thereby allowing the clot to be more efficiently aspirated into catheter 10. In addition, for a given suction force applied to inner lumen 25 at proximal end 12A of elongated body 12, a larger distal opening to inner lumen 25 provided by expandable member 18 enables a greater suction force to be applied to a thrombus, even if a more proximal portion of elongated body 12 has a smaller diameter than the distal opening.

By incorporating expandable member 18 into the design of catheter 10, catheter 10 may offer several advantages over conventional aspiration catheters. For example, by constructing catheter 10 with only structural support member 30 (e.g., at the exclusion of expandable member 18), catheter 10 may exhibit one or more desired navigability characteristics (e.g., strength, flexibility, kink-resistance, or the like), but would exhibit limited-to-no expandability at the distal end. To improve the aspiration efficiency, the diameter of the catheter may be increased to provide engagement with the clot, but the increased diameter may reduce the overall navigability of the catheter through vasculature of the patient. The inclusion of expandable member 18 may allow the diameter of elongated body 12 (e.g., within proximal portion 16A) to remain relatively small and exhibit the improved navigability characteristics of a catheter body with a small diameter, while expandable member 18 would provide catheter 10 with the improved engagement and suction characteristics that may be attributed to having a large diameter of mouth 13 at distal end 12B. In some examples, the presence of expandable member 18 may lead to improved revascularization success rates, such as due to the improved clot engagement (e.g., to better pull the entirety of the clot into catheter 10 during aspiration) as described herein.

In some examples, the shape and configuration of expandable member 18 may provide better engagement with the clot. In some examples, distal movement or migration of the clot or other material relative to the expandable member 18 or catheter 10 is prevented or inhibited by the expandable member 18. For example, the inner surface of the expandable member 18 may prevent or inhibit distal movement of the clot/material relative to the expandable member 18 or catheter 10. This may involve entanglement of the clot/material in the expandable member 18, and/or frictional resistance to distal movement of the clot/material by the inner surface of the expandable member 18. For example, an inner surface of expandable member 18, e.g., defining lumen 25 and/or on a membrane if present, may define a plurality of engagement members, e.g., teeth or hooks, extending into lumen 25 and configured to engage the clot and proximally draw the clot into the mouth 13 of catheter 10 as expandable member 18 expands into an expanded configuration or as the clot is drawn into lumen 25 via a suction force applied to lumen 25 by suction source 4 (FIG. 1A).

In an expanded configuration, expandable member 18 may define a funnel shape. For example, expandable member 18 may taper from a relatively small cross-sectional dimension near the proximal end of expandable member 18 to a relatively large cross-sectional dimension of mouth 13 at distal end 12B of elongated body 12. That is, the cross-section of expandable member 18 may be wider at a distal end than a proximal end. For example, in the expanded configuration, the distal end of expandable member 18 may be about 150 percent to about 300 percent wider than an inner diameter of proximal portion 16A of elongated body 12. In some examples, the cross-sectional shape (taken in a direction orthogonal to longitudinal axis 26) of expandable member 18 may be round (e.g., circularly shaped) and the cross-sectional axis may be referred to as a diameter. In other examples, expandable member 18 may have an irregularly shaped cross-section, in which case the cross-sectional dimension may be referred to as the major dimension (e.g., a longest dimension of the cross-section). Thus, while a major dimension of expandable member 18 is primarily referred to as a diameter herein, in other examples, expandable member 18 can have other shapes in cross-section.

In an example, the increased diameter of mouth 13 at distal end 12B may allow for better sealing capabilities with the vessel wall and better engagement with a clot during aspiration. For example, during aspiration with a conventional catheter, engagement with the clot may be reduced due to the relatively small diameter of the catheter at its distal tip. Additionally, due to the size of the catheter relative to the vessel diameter, spacing between the interior of the vessel wall and the exterior of the catheter can result in a general loss of suction power. In contrast, the increased diameter of expandable member 18 may provide better sealing with the vessel wall thereby resulting in a reduced loss of suction. Additionally, in examples where the cross-section is generally round, the increased diameter and funnel shape of expandable member 18 may allow for a large portion of the clot to be received within the inner volume defined by the funnel shape to provide improved sealing and physical engagement with the clot during the aspiration procedure.

Expandable member 18 can be made from any suitable material, such as, but not limited to, a metal (e.g., a nickel titanium alloy (Nitinol), stainless steel, tungsten, titanium, gold, platinum, palladium, tantalum, silver, or a nickel-chromium alloy, a cobalt-chromium alloy, or the like), a polymer, a fiber, or any combination thereof. In some examples, expandable member 18 may be formed from a shape memory metal (e.g., nickel titanium (Nitinol)). As discussed in further detail below, in some examples, expandable member 18 may include one or more magnetic materials that facilitate expansion and/or contraction of expandable member 18. The materials of expandable member 18 may be selected so that once in an expanded configuration, expandable member 18 substantially maintains its shape, even in the presence of the vacuum force applied to catheter 10 during the aspiration process.

Expandable member 18 may be of any suitable length and diameter, which may be selected based on the target vessel or particular procedure being performed. In some examples, expandable member 18 may be about 2 centimeters to about 25 centimeters long measured in a direction parallel to longitudinal axis 26 and configured to expand to about 150 percent to about 300 percent of the outer diameter of its collapsed configuration or the diameter of the proximal end of expandable member. As discussed above, in some examples, in the collapsed state, expandable member 18 may have a cross-sectional dimension equal to or substantially equal to the outer diameter of elongated body 12 proximate to expandable member 18. In an example, expandable member 18 may be about 1.5 cm, about 2.0 cm, or about 2.5 cm in length. In some examples, the expanded outer diameter or the cross-sectional dimension of mouth 13 of elongated body 12 at distal end 12B may be about 200 percent, 250 percent, 300 percent, or another percentage larger compared to a portion of elongated body 12 that includes only structural support member 30 (e.g., the diameter or cross-section at line A-A of FIG. 2B). In some examples, to the expandability of expandable member 18 at distal portion 16B may allow the cross-sectional dimension of elongated body 12 within proximal portion 16A to remain comparatively small. As described above, such a combination may enable catheter 10 to exhibit the improved navigability characteristics of catheter body with a small diameter while still providing catheter 10 with the improved engagement and suction characteristics that may be attributed to having a large diameter of mouth 13 at distal end 12B.

In some examples, expandable member 18 may be mechanically coupled to structural support member 30 and/or layered between (at least in a proximal portion of the expandable member 18) inner liner 28 and outer jacket 32. For example, expandable member 18 and structural support member 30 can be formed independently of one another, and the proximal end of expandable member 18 may be coupled to the distal end of structural support member 30. In some examples, expandable member 18 and structural support member 30 may be joined via welding, brazing, soldering, epoxy, mechanical attachment mechanisms (e.g., hooks) or other suitable technique. In other examples, structural support member 30 and expandable member 18 may be integrally formed, e.g., have a unibody configuration. For example, structural support member 30 and expandable member 18 may be formed using the same hypotube. As an example, the proximal portion of the hypotube can be spirally cut to form a coil structure (e.g., structural support member 30) while the distal portion of the hypotube can be cut to form the components of any of the various examples of expandable member 18 described herein.

Additionally, or alternatively, expandable member 18 may be at least partially secured to structural support member 30 via inner liner 28 and/or outer jacket 32. For example, expandable member 18 may not be directly coupled to structural support member 30 or may not be in direct contact (e.g., abutting contact) with structural support member 30, although the two structures may be in the same radial layer of elongated body 12 in some cases. In an example, expandable member 18 may be positioned adjacent to structural support member 30 over inner liner 28, and outer jacket 32 may be positioned over expandable member 18 and structural support member 30. For example, outer jacket 32 may be heat-shrunk over expandable member 18 and structural support member 30 such that outer jacket 32 secures both expandable member 18 and structural support member 30 in place relative to inner liner 28. In such examples, expandable member 18 may be positioned at least partially between inner liner 28 and outer jacket 32 (e.g., layered or positioned between distal section 28B of inner liner 28 and distal section 32B of outer jacket 32). For example, at least a proximal portion of expandable member 18 may be positioned between inner liner 28 and outer jacket 32.

One or both of inner liner 28 or outer jacket 32 may extend over the entire length of expandable member 18, may extend over only a portion of the length of expandable member 18, or may not overlap with expandable member 18. For example, distal section 28B of inner liner 28 may extend over only part of the length of expandable member 18 leaving portions of expandable member 18 exposed to inner lumen 22. In some cases, the exposed portions of expandable member 18 may provide better engagement with a clot and/or prevent distal migration of clot from catheter 10 due to the texture of expandable member 18 or direct electrostatic engagement with expandable member 18. For example, as described in some examples herein, elongated body 12 may comprise an electrical conductor electrically coupled to expandable member 18, and expandable member 18 may be configured to receive an electrical signal via the conductor that causes expandable member 18 to electrostatically engage the clot.

In some examples, an inner surface of expandable member 18 may comprise a surface treatment configured to promote at least one of mechanical or chemical engagement between the inner surface and the clot. In some examples, a coating may be applied to portions of the inner surface of expandable member 18 (e.g., the inner surface of the struts) or the inner surface of inner liner 28, or the surfaces may be textured via etching or otherwise roughened (or rougher) in comparison to the outer surface of the expandable member 18 to better mechanically engage the clot. In some examples, the inner surface of the distal section 28B of inner liner 28 may be etched, such as to promote mechanical clot engagement.

In some examples, clot engagement with expandable member 18 may be enhanced by delivering electrical energy to expandable member 18. For example, a source of electrical energy (e.g., an electrical signal generator) may deliver an electrical signal to expandable member 18 via one or more electrical conductors (not shown) electrically coupled to expandable member 18. The electrical energy may be positively charged to electrostatically engage a clot. Characteristics of the electrical energy may be adjusted to better engage the clot, such as polarity, or an amount or type of current delivered. For example, pulsed direct current may be employed, optionally with a non-square and/or non-negative waveform. The electrical conductors can extend through inner lumen 22 of elongated body 12, can extend along an outer surface of elongated body 12, can be embedded in a wall of elongated body 12, or have any other suitable configuration.

Although FIG. 2B illustrates an example in which both inner liner 28 and outer jacket 32 terminate proximal to a distal end of expandable member 18, in other examples, inner liner 28 and outer jacket 32 can have other arrangements relative to expandable member 18. For example, inner liner 28 and/or outer jacket 32 may not overlap with expandable member 18 or may only overlap with a proximal-most portion of expandable member 18 that does not expand. As another example, a distal section 28B of inner liner 28 may be fully coextensive with expandable member 18, and/or outer jacket 32 may be fully coextensive with expandable member 18.

Expandable member 18 may expand from a collapsed configuration to an expanded configuration using any suitable technique, as detailed further in the examples below. In some examples, expandable member 18 is configured to self-expand. For example, expandable member 18 may be formed from a shape memory material such as Nitinol. Additionally or alternatively, expandable member 18 may include one or more magnetic elements enabling expandable member 18 to self-expand in response to the forces of magnetic repulsion and/or attraction. In some such examples, catheter 10 may include a retractable sheath over expandable member 18 that helps retain expandable member 18 in a collapsed configuration, e.g., during navigation of elongated body 12 to a target treatment site within the vasculature of a patient. Once at the target treatment site, the retractable sheath may be withdrawn proximally over elongated body 12 to allow expandable member 18 to self-expand. In other examples, an electrical energy may be used to expand expandable member 18. For example, expandable member 18 (or a portion or a layer thereof) may be formed from a material or metal that bends or deflects in response to a current passed therethrough (or to heat generated as a result of such current). One such type of material is shape memory alloy actuator material, e.g. nitinol or Flexinol™ available from Dynalloy, Inc. of Irvine, California USA. In some examples, a control unit, such as control circuitry 8 of FIGS. 1A and 1B, may cause expandable member 18 to expand and/or contract, such as in response to receiving user input, or automatically.

Expandable member 18 may include any of a number of different structural aspects, components, configurations, or applications described herein. The following examples of expandable member 18 are not mutually exclusive, e.g., any or all of the aspects of the various depicted examples may simultaneously be used in combination with one another.

Figure 3A:
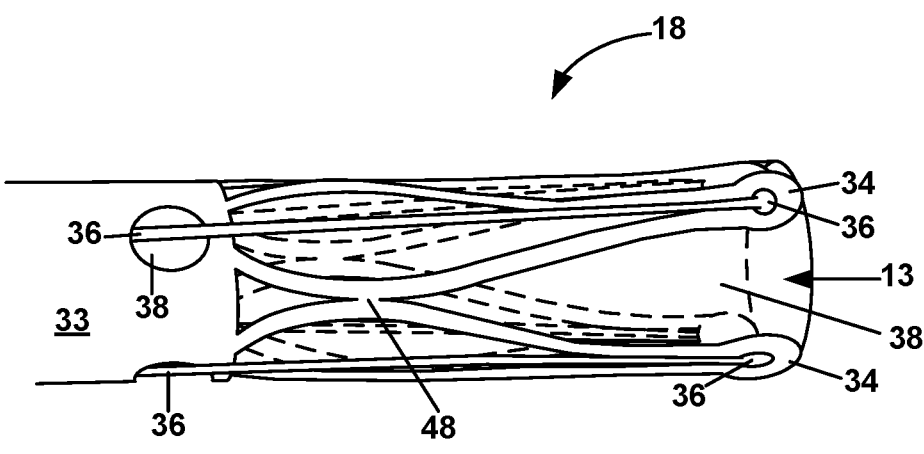
FIGS. 3A and 3B are perspective views of an example expandable member in a contracted configuration at a distal portion of a catheter.
Figure 3B:
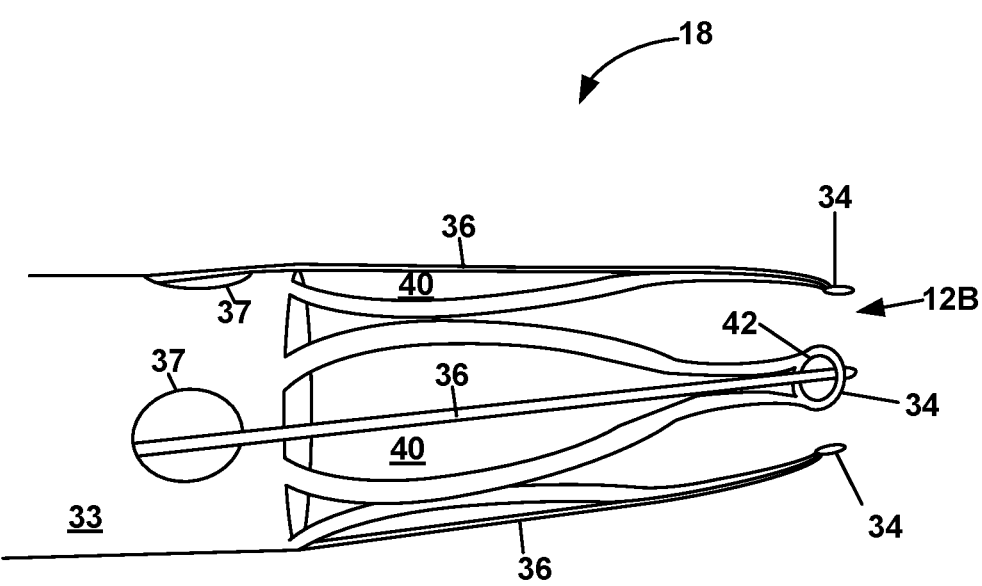
Figure 3C:
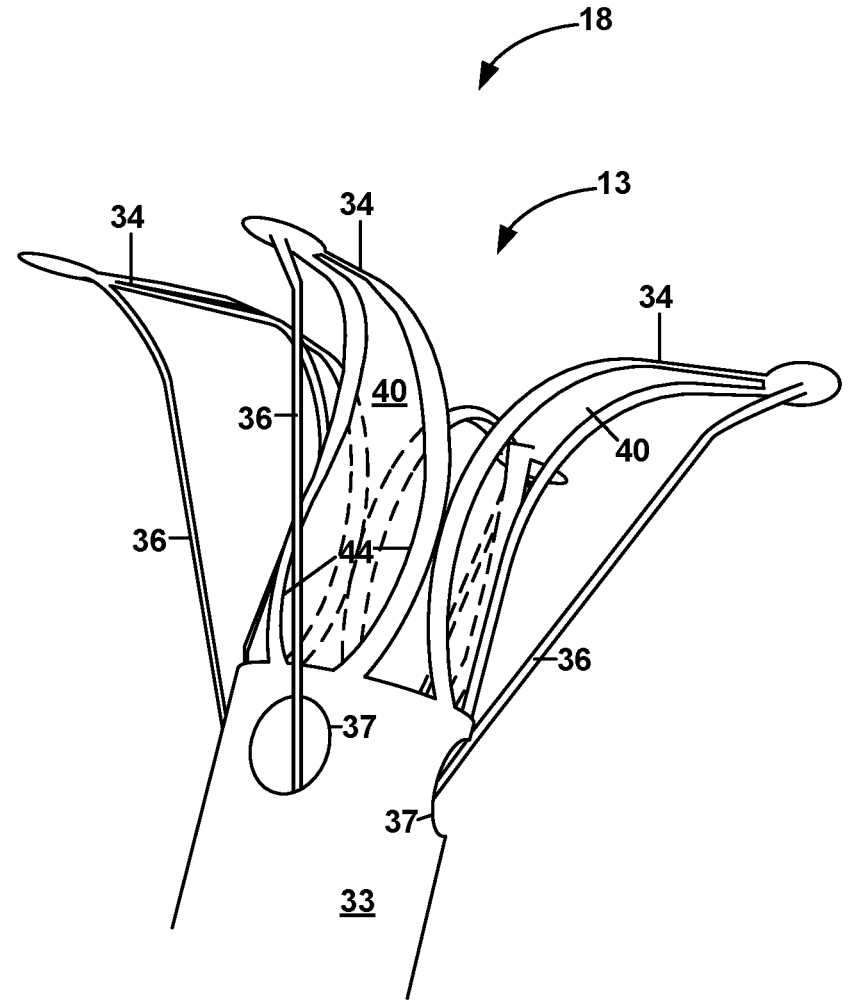
FIG. 3C is a perspective view of the expandable member of FIGS. 3A and 3B in an expanded configuration.
Figure 4:
FIG. 4 is a conceptual diagram depicting an example method for expanding an expandable member of a catheter.
Figure 4:
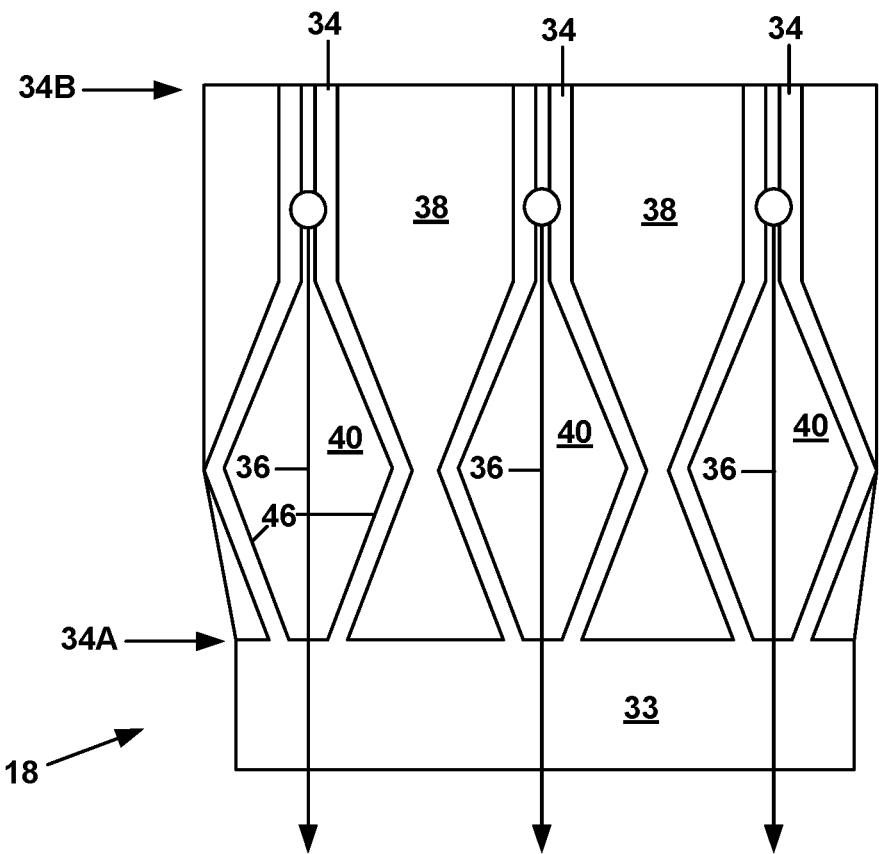
Figure 5:
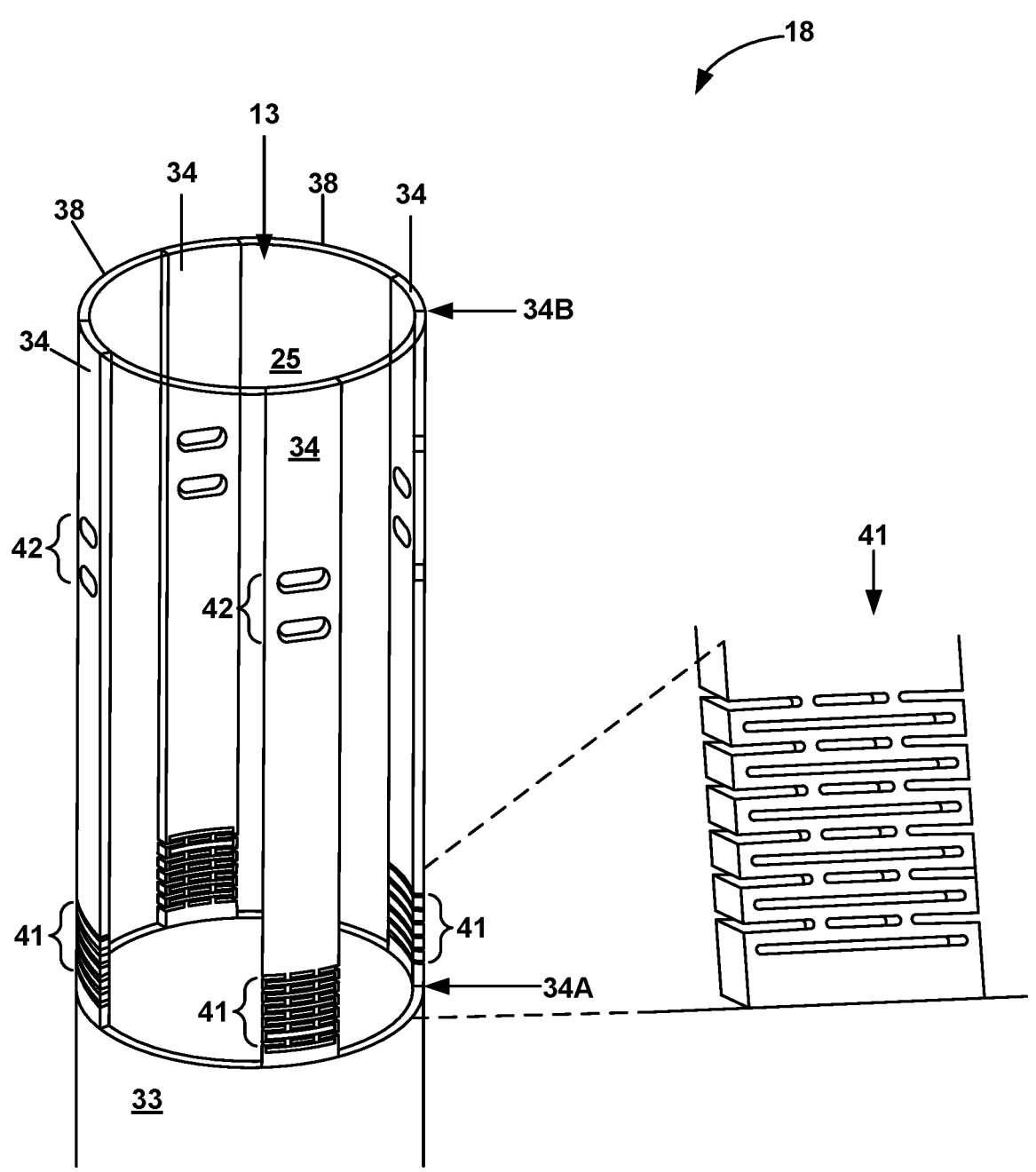
FIG. 5 is a perspective view of another example expandable member of a catheter.
Figure 6A:
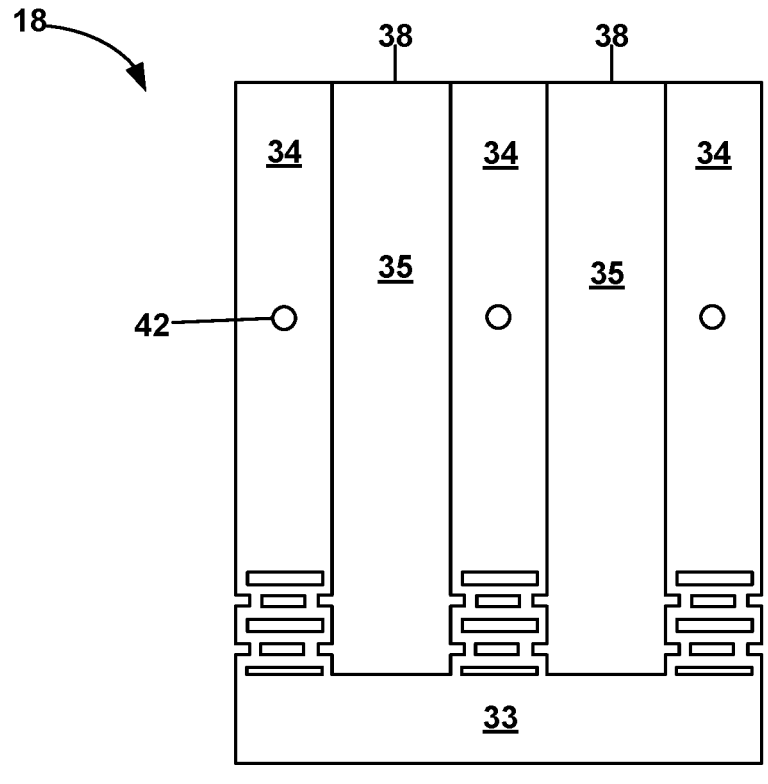
FIGS. 6A and 6B are conceptual diagrams depicting example methods for expanding the expandable member of FIG. 5.
Figure 6B:
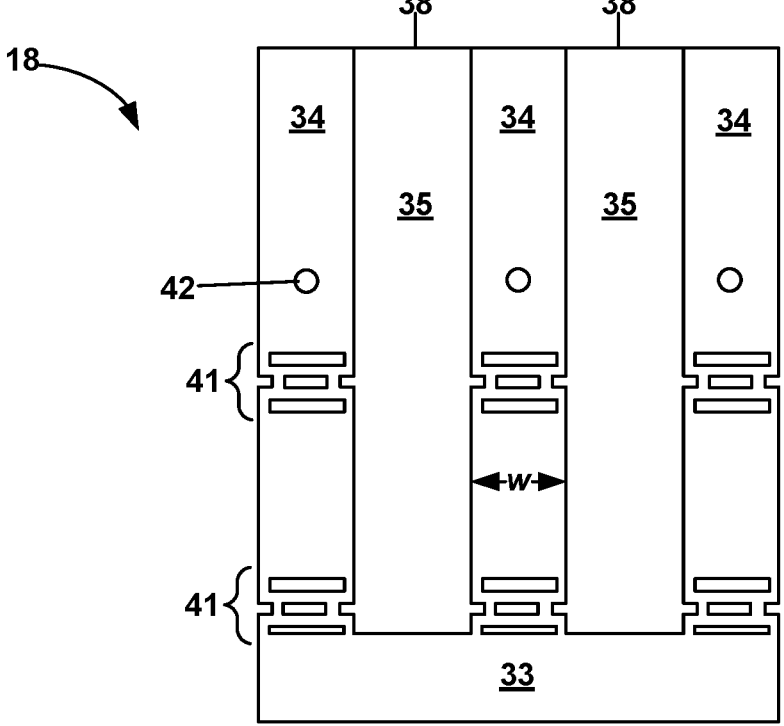

In some examples, as shown in FIGS. 2A-6B, one example of expandable member 18 includes a tubular body 33 and a plurality of flexible prongs 34 extending axially from tubular body 33 in a distal direction. Expandable member 18 is depicted in a collapsed configuration in FIGS. 2A, 3A, 3B, and 5 and in an expanded configuration in FIGS. 2B and 3C. FIGS. 4, 6A, and 6B are conceptual diagrams depicting an "unrolled" or "flattened" expandable member 18 in order to illustrate various example structural components of tubular body 33.

Flexible prongs 34 are disposed circumferentially around central longitudinal axis 26 of elongated body 12, and may be either evenly or unevenly distributed around the circumference of tubular body 33. For example, any two consecutive (e.g., circumferentially adjacent) flexible prongs 34 may define a gap 35 between them, and any two gaps may be approximately equal or not equal in size. In some examples, gaps 35 may be sufficiently small to reduce a probability that a clot or thrombus escapes through the gaps when expandable member 18 is engaged with the clot or thrombus. Flexible prongs 34 may have any suitable length, measured from a respective proximal end 34A to a respective distal end 34B (ends 34A, 34B are labeled in FIG. 4). In some examples, each flexible prong 34 may define a length from about 0.5 cm to about 2.5 cm.

Expandable member 18 may include any number of prongs 34. In some examples, expandable member 18 includes four to six prongs 34 circumferentially spaced around distal end 12B of elongated body 12. In some examples, prongs 34 may be heat-set so as to define a contracted configuration of expandable member 18 in an at-rest state, e.g., when a user has not actuated prongs 34 to expand expandable member 18 to the expanded configuration. In some examples, in a contracted configuration of expandable member 18, prongs 34 are substantially parallel (e.g., parallel or nearly parallel to the extent permitted by manufacturing tolerances) with central longitudinal axis 26 of catheter 10. In other examples, however, prongs 34 are not parallel with central longitudinal axis 26 in the collapsed configuration of expandable member 18 and are instead, for example, angled relative to central longitudinal axis 26. For example, prongs 34 may be curved or angled toward central axis 26 in a distal direction, such that, in a contracted configuration, expandable member 18 defines a tapered distal tip of elongated body 12, e.g., such that distal ends 34B of the prongs 34 are closer to central longitudinal axis 26 than the proximal ends 34A. In some of these examples, a cross-sectional dimension of elongated body 12 is smallest near distal end 12B, as compared to a cross-sectional dimension of elongated body 12 between proximal end 12A and distal end 12B.

Expandable member 18 (including prongs 34) may be formed using any suitable technique. In some examples, expandable member 18 is cut (e.g., laser cut) from a single piece of material, such as a shape memory material (e.g., Nitinol) or stainless steel. In other examples, at least some prongs 34 may be formed separate from each other and subsequently connected to each other (e.g., via a tubular body 33) to define expandable member 18.

Expandable member 18 is configured to be expanded using one or more techniques, including via a proximal force pulling back on a part of expandable member 18 (e.g., prongs 34), via one or more magnetic materials incorporated into expandable member, or any combination thereof. As shown in FIG. 2A, in some examples, catheter 10 may include a user-input device 20 (e.g., a button, dial, lever, switch, joystick, and the like) configured to activate or control expansion and/or contraction of expandable member 18. In the example of FIG. 2A, user-input device 20 is depicted as a button or slider located on handle 14. Other configurations of user-input device 20 can be used in other examples, such as a rotatable wheel, as one non-limiting example.

A user may interact with user-input device 20 to manually (e.g., mechanically) transition expandable member 18 between a contracted configuration and an expanded configuration, as detailed further below. For example, a user may slide user-input device 20 within a channel defined by handle 14 to proximally retract one or more pull members connected to expandable member 18 and input device 20 to cause expandable member 18 to expand radially outward. As another example, a user may rotate a rotatable wheel in one direction to proximally retract one or more pull members connected to expandable member 18 to cause expandable member 18 to expand radially outward and rotate the rotatable wheel in an opposite direction to cause the pull members to cause expandable member 18 to move to a contracted configuration.

In other examples, catheter 10 includes control circuitry 8 or is otherwise electrically connected to control circuitry 8 (FIGS. 1 and 2A), which is configured to control the expansion and contraction of expandable member 18, and user-input device 20 may be communicatively coupled (e.g., in wired or wireless data communication) with control circuitry 8. For example, in response to receiving user input via user-input device 20, control circuitry 8 may cause expandable member 18 to expand and contract. As another example, control circuitry 8 may be configured to control expandable member 18 to move between an expanded configuration (e.g., a fully expanded configuration or a partially expanded configuration) and contracted (e.g., a fully collapsed or partially collapsed) configuration based on the expansion frequency. The expansion frequency can indicate, for example, the number of times expandable member 18 is in the expanded configuration or the contracted configuration per unit of time. Thus, the expansion frequency can, in some examples, indicate the timing with which control circuitry 8 causes expandable member 18 to transition between the expanded configuration and the contracted configuration.

Control circuitry 8 can determine the expansion frequency using any suitable technique. For example, a clinician may provide input to control circuitry 8 via user-input device 20 or another user input device that indicates a desired expansion frequency at which control circuitry 8 cyclically expands and contracts expandable member 18.

In some examples, control circuitry 8 is configured to control the expansion and contraction of expandable member 18 based on a cardiac cycle of a patient. For example, control circuitry 8 may determine an expansion timing or expansion frequency based on the cardiac cycle based on data received from one or more sensors (e.g., part of, or connected to, sensing circuitry 11 of FIGS. 1A and 1B) configured to detect the cardiac cycle of the patient. For example, control circuitry 8 may be configured to determine which part of a cardiac cycle a heart of patient is in and control expandable member 18 to assume an expanded configuration or a collapsed configuration during a first part of the cardiac cycle, such as diastole, and to conversely, assume the other of the expanded configuration or the collapsed configuration, respectively, contract during a second part of the cardiac cycle, such as systole. A part of a cardiac cycle can include a portion of the cardiac cycle and does not span multiple cardiac cycles. It is believed that controlling the expansion and contraction of expandable member 18 based on the cardiac cycle of a patient may more quickly and more effectively remove a thrombus from a blood vessel of a patient by varying an amount of suction force applied to the clot.

Control circuitry 8 can determine the cardiac cycle (e.g., the current phase of a cardiac cycle) using any suitable technique. For example, control circuitry 8 can determine a current phase of a cardiac cycle of a patient based on an electrical cardiac signal, a blood pressure, blood oxygen saturation, or another physiological parameter that changes as a function of a cardiac cycle of the patient. In some examples, control circuitry 8 is otherwise communicatively coupled to sensing circuitry 11 configured to generate a signal indicative of a physiological parameter of the patient indicative of the cardiac cycle, and the control circuitry is configured to receive the signal and determine the cardiac cycle (e.g., a specific phase of the cardiac cycle) based on the signal. The signal can include, for example, one or more of an ECG, an EGM, a photoplethysmogram (PPG), a heart sound phonocardiogram, or a blood pressure signal. The sensing circuitry can include, for example, one or more of an electrocardiogram sensor, an electrogram sensor, a blood oxygen saturation sensor, or an arterial blood pressure sensor.

In some examples, control circuitry 8 may additionally be configured to control the amount of suction force applied to catheter 10. For example, control circuitry 8 may be configured to control a suction frequency (e.g., a frequency with which suction source 4 modifies a suction source between relatively high and relatively low suction forces) and/or the suction force applied by suction source 4 (FIG. 1A). In such examples, control circuitry 8 may be configured to control the suction frequency of suction source 4 (FIG. 1A) independently from the expansion frequency of expandable member 18. In other examples, control circuitry 8 may be configured to control the periodic suction force of the pump and the cyclical expansion of expandable member 18 according to a common frequency, such as based on the cardiac cycle as described above.

In some examples, catheter 10 may include a sensor (e.g., sensing circuitry 11 of FIGS. 1A and 1B) configured to detect a natural frequency (e.g., a resonant frequency) of a clot within the patient's vasculature. In such examples, control circuitry 8 may control the expansion frequency of expandable member 18 based on the natural frequency of the clot or a surrogate for the natural frequency (e.g., a frequency that corresponds to the natural frequency of the clot) in order to more-effectively aspirate the clot. For example, sensing circuitry 11 may include an intravascular vibrometer probe and/or an intravascular ultrasound transducer configured to measure the natural frequency of the clot. In some examples, control circuitry 8 and/or sensing circuitry 11 may be configured to indirectly determine (e.g., estimate) the natural frequency of a clot by measuring one or more parameters of the clot that are relatively strongly correlated with the natural frequency, such as the fibrin density of the clot, and then determine the natural frequency based on the known correlation relationship between the measured parameter and the natural frequency. In other examples, a clinician may determine the fibrin content of the clot during pre-procedure imaging, such as through medical imaging (e.g., computerized tomography (CT) imaging or ultrasound imaging), wherein clots having a higher fibrin density may appear relatively brighter on the CT or other medical images. The clinician may then input an indication of the determined natural frequency to control circuitry 8.

Although shown internal to handle 14 in FIG. 2A, in other examples, control circuitry 8 can be separate from handle 14 and electrically connected to components of catheter 10 via a wired or wireless connection.

In some examples, as shown in FIGS. 2B-4, expandable member 18 is configured to be expanded via at least one actuation member, which is shown in the example of FIGS. 2B-4 as at least one elongated pull member 36. Pull member 36 may include a relatively thin filament or wire, such as made from a metal, polymer, or other relatively robust material configured to withstand a proximal pulling force sufficient to pull back on prongs 34 without breaking. A distal portion (e.g., a distal-most end) of pull member 36 may be mechanically coupled (e.g., welded, glued, bonded, soldered, tied, adhered, etc.) to at least one prong 34 of the plurality of prongs 34, such that a distal portion or the distal end 34B of the respective prong 34 is configured to expand radially outward relative to the central longitudinal axis 26 in response to a tensile force (as indicated by the arrows in FIG. 4) applied to pull member 36. For example, pull member 36 may extend proximally from an exterior surface of prong 34, through an opening 37 defined by tubular body 33 of and into an interior of elongated body 12 (e.g., into inner lumen 22 and/or between inner liner 28 and outer jacket 32). Within elongated body 12, pull member 36 may proximally extend the entire length of elongated body 12 and into handle 14, for example, into handle lumen 23 (FIG. 2A).

As shown in FIG. 2A, handle 14 may include a switch, button, or other user-input device 20. In some examples, but not all examples, user-input device 20 may be configured to mechanically apply a proximal tensile force to a proximal portion (e.g., a proximal end) of pull member 36, in response to manual activation by a user. In other examples, user-input device 20 is communicatively coupled to control circuitry 8 (e.g., via a motor under control of control circuitry 8), configured to mechanically apply a proximal tensile force to a proximal portion (e.g., a proximal end) of pull member 36, in response to activation of user-input device 20 by a user.

In response to the proximal tensile force, pull member 36 distally retracts distal end 34B of prong 34, causing mouth 13 at the distal-most end 12B of elongated body 12 to expand radially outward. In this way, the techniques of this disclosure enable a user to open and close the catheter tip in a predictable and controllable manner. For example, by actuating expandable member 18 to remain in an expanded configuration, the techniques of this disclosure may reduce or prevent the distal end 126 of elongated body 12 from collapsing and/or closing in response to a proximal suction force during an aspiration procedure.

In some examples, as shown in FIGS. 2-4, expandable member 18 includes a plurality of pull members 36, wherein a distal portion of each pull member 36 is mechanically coupled to a respective prong 34. In some examples, proximal portions of all of the plurality of pull members 36 may be coupled together, such that activation of user-input device 20 on handle 14 applies a proximal force to all of pull members 36 simultaneously, causing a radially symmetric expansion of expandable member 18 (e.g., in examples in which prongs 34 are evenly distributed around tubular body 33). In other examples, catheter 10 can be configured such that one or more pull members 36 may be actuated (e.g., pulled) individually, enabling a clinician to customize the expanded shape of expandable member 18 and, therefore, the expanded shape of mouth 13 at distal end 12B of elongated body 12. For example, during aspiration of a thrombus or clot, a user (e.g., a physician) may determine that a particular expanded configuration of expandable member 18 may be more efficient or successful by conforming mouth 13 to the shape of the thrombus. Separate control over one or more pull members 36 may allow for improved control over the expansion of expandable member 18.

As shown in FIGS. 2A-4, in some examples, each of prongs 34 may be formed (e.g., laser-cut) from a relatively thin material (wherein the thickness is measured radially from central longitudinal axis 26). In some of these examples, as shown in FIG. 3C, each prong 34 is configured to bend or curve along its entire axial length in response to the proximal force from the respective pull member 36. In other examples, each prong 34 can be configured to bend or curve along only part of its length.

For example, each prong 34 may be formed or cut into a generally oval, diamond, or flower-petal shape, defining a wider central portion, narrower proximal and distal portions, and an opening 40 extending along a substantial length of the respective prong 34 (e.g., from proximal end 34A toward distal end 34B of each prong 34). For example, as shown in FIGS. 2A-3C, each prong 34 may include a pair of curvilinear members 44. In the example shown in FIG. 4, each prong 34 may include a pair of linear or V-shaped members 46. In some examples, each prong 34 may include a combination of linear and curvilinear members.

In some examples, but not all examples, directly adjacent prongs may be coupled to one another at one or more points that are located distal to tubular body 33. For example, as shown in FIG. 3A, circumferentially adjacent prongs 34 may be coupled together at a circumferentially widest point 48 of each prong, such that expandable member 18 may only bend, flex, or expand along a region distal to point 48.

In other examples, each of prongs 34 may be formed (e.g., laser-cut) from a relatively thicker material, wherein the thickness is measured radially from central longitudinal axis 26. For example, as shown in FIGS. 5-6B, each of prongs 34 may be formed (e.g., laser-cut) into a generally rectangular-prism shape (e.g., having a generally uniform width w (FIG. 6B) along its axial length between proximal end 34A and distal end 34B). In other examples, thicker prongs 34 may include other shapes, such as shapes having non-uniform widths w along their respective axial lengths. For example, some or all of the prongs 34 may decrease in width w in a distal direction, or may increase in width w along its length in a distal direction and then subsequently decrease in width w such that prongs 34 define a shape similar to the shapes shown in FIGS. 3A-4.

In examples in which each of prongs 34 may be formed from a relatively thicker material, rather than bending or curving along the entire length of the prong 34, each prong 34 may be configured to bend or flex at one or more designated hinges 41 along the length of the prong 34. For examples, hinges 41 may enable controlled bending of prongs 34 in a radial direction, as well as reduce unintended bending of prong 34 in other directions, such as circumferential bending. As an example, hinges 41 may each define a pivot point for bending of prongs 34.

Hinges 41 may have any suitable structure configured to provide a region of preferential bending relative to other regions of the prong 34. For example, each of hinges 41 may include one or more openings cut into a material of the respective prong 34, weakening that particular section of the prong 34, enabling it to bend in response to the tensile force from the pull member 36. Each prong 34 may include one hinge 41 (as shown in FIGS. 5 and 6A), two hinges 41 (as shown in FIG. 6B), or more than two hinges 41. In some examples, as shown in FIGS. 6A and 6B, a hinge 41 may be located at a proximal-most edge of the respective prong 34. In other examples, a hinge 41 may be located elsewhere along the axial length of the respective prong 34 (e.g., between proximal end 34A and distal end 34B). The axial location of hinges 41 may affect a size and/or shape of the resulting expanded configuration of expandable member 18.

As shown in FIG. 3A, in some examples, expandable member 18 may define a relatively uniform circumference (e.g., uniform radius extending from central axis 26) when in a contracted configuration. In other examples, such as the example of FIG. 3B, expandable member 18 may taper toward distal end 12B of elongated body 12, while in a contracted configuration.

As shown in FIGS. 3B, 5, 6A, and 6B, in some examples, each prong 34 may define one or more distal openings 42. Distal openings 42 are configured to receive a distal-most end of a respective pull member 36. For example, as shown in FIG. 3B, pull member 36 may distally extend from an exterior surface of each prong 34 and through a distal opening 42, where the distal-most end of pull member 36 may be attached (e.g., welded, etc.) to an interior surface of the respective prong 34. In other examples, such as shown in FIGS. 3A and 3C, the distal-most end of each pull member 36 may be attached (e.g., welded, etc.) directly onto the exterior surface of a respective prong 34.

In some examples, expandable member 18 includes a flexible substrate or membrane 38 disposed circumferentially around prongs 34 in order to fill in the gaps 35 between adjacent prongs 34. As shown in FIG. 3A, membrane 38 may be positioned radially inward of prongs 34 and/or radially outward of prongs 34. Membrane 38 may include, for example, a fluid-impermeable membrane, such as a blood impermeable membrane. For example, membrane 38 may include a polymer covering configured to complete a suction seal (e.g., to help maintain vacuum pressure within lumen 25 while engaged with clot) and prevent a flow of fluids (e.g., blood, saline, and the like) between consecutive prongs 34. Membrane 38 may also help catheter 10 to block an antegrade blood flow while inserted within a patient's vasculature, which may reduce or prevent emboli from flowing through and/or past the distal opening into lumen 25 of catheter 10 during an aspiration procedure. Membrane 38 may be configured to stretch or fold to allow for expansion and contraction of expandable member 18. In the examples depicted in FIGS. 3B and 3C, membrane 38 has been removed to show the structure of prongs 34.

In some examples, membrane 38 may not extend the entire axial length of expandable member 18, for example, may cover only a proximal portion of prongs 34, terminating proximally of the distal end 34B of prongs 34. In some examples, membrane 38 is made of ePTFE and is adhered to prongs 34 of expandable member 18 with suitable adhesive. In some examples, membrane 38, which may contact a wall of a vessel within a patient's vasculature, may be perforated with perforations or "weep holes." These perforations may facilitate purging the device of air just prior to implantation. Weep holes may also be provided in the proximal-facing surface of the membrane, if it beneficial to permit some small seepage of blood past the membrane 38.

For ease of illustration of the structure of the example expandable members described herein, membrane 38 is only shown in the example of expandable member 18 shown in FIG. 3A. Any expandable member described herein can include membrane 38 in some examples.

Figure 7:
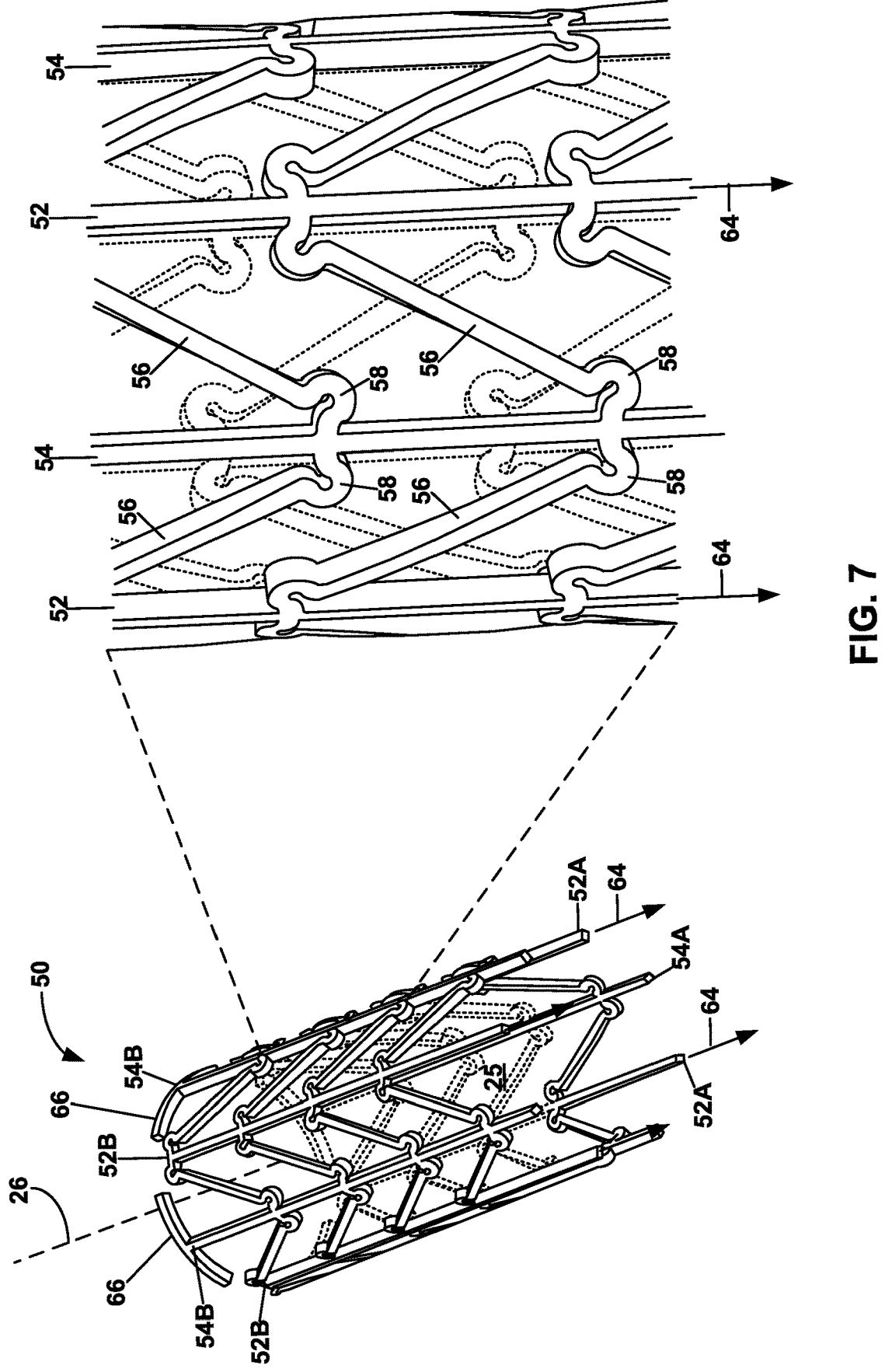
FIG. 7 is a perspective view of another example expandable member of a catheter.
Figure 8B:
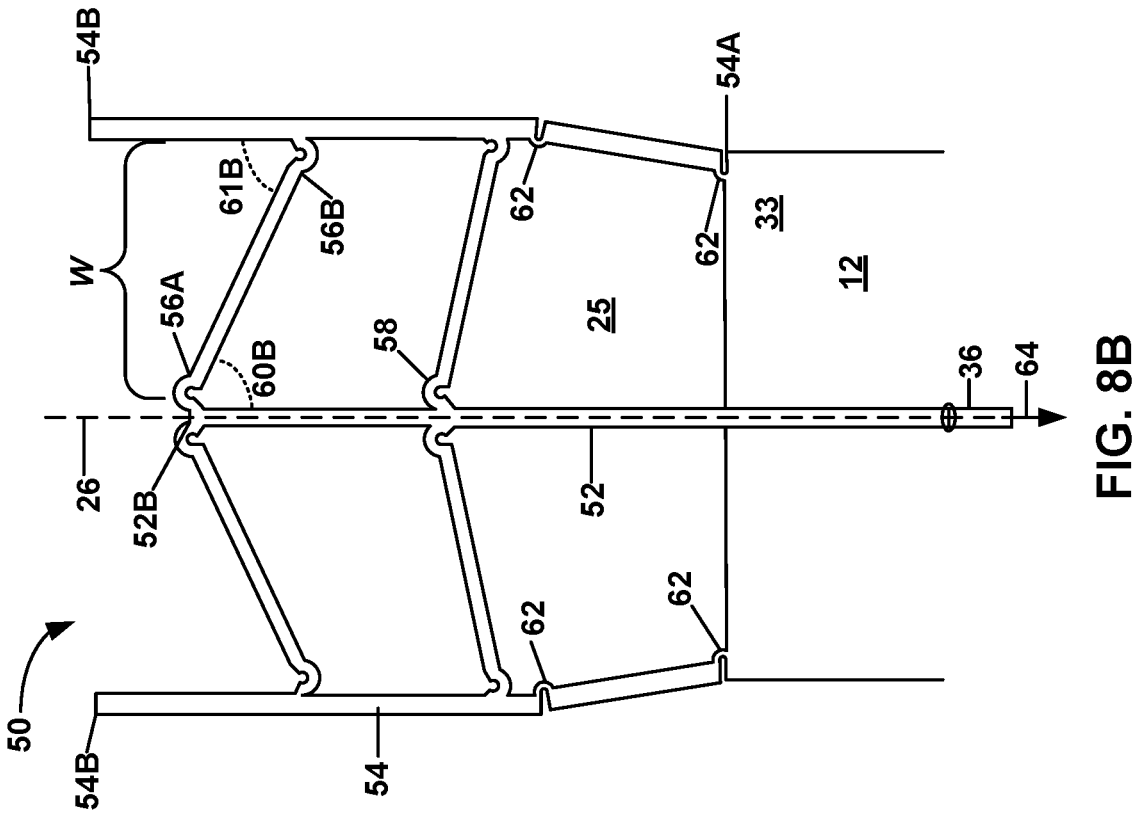
FIGS. 8A and 8B are conceptual diagrams depicting example methods for expanding the expandable member of FIG. 7.
Figure 8A:
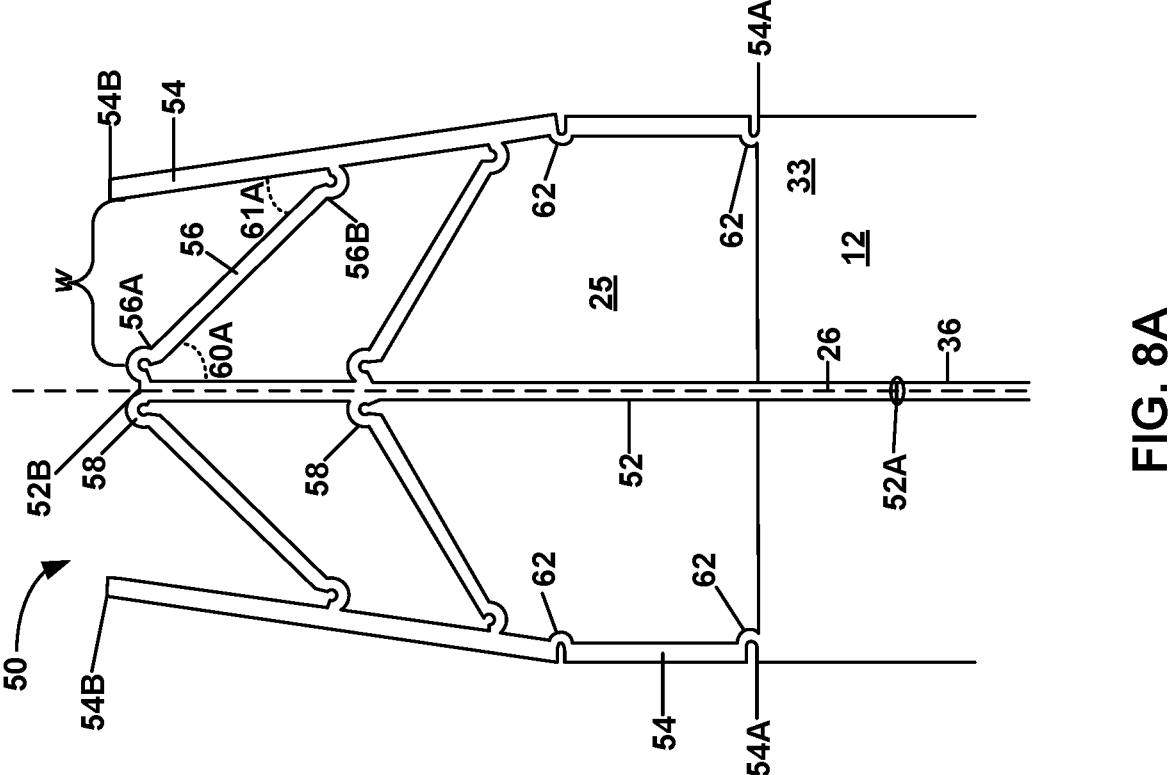

FIGS. 7-8B depict another example expandable member 50, which is an example of expandable member 18 of catheter 10. Specifically, FIG. 7 is a perspective view of an example expandable member 50, and FIGS. 8A and 8B are conceptual diagrams depicting techniques for expanding expandable member 50 from a contracted configuration (FIG. 8A) to an expanded configuration (FIG. 8B). Expandable member 50 may be an example of expandable member 18 of FIG. 2A. For example, as with expandable member 18, in some examples, expandable member 50 may be mechanically coupled to the structural support member 30 and/or layered between (at least in a proximal portion of the expandable member 50) inner liner 28 and outer jacket 32. For example, expandable member 50 and structural support member 30 can be formed independently of one another, and the proximal end of expandable member 50 may be coupled to the distal end of structural support member 30 or structural support member 30 and expandable member 50 can remain unconnected within catheter 10. In some examples, expandable member 50 and structural support member 30 may be joined via welding, brazing, soldering, epoxy, mechanical attachment mechanisms (e.g., hooks) or other suitable technique. In other examples, structural support member 30 and expandable member 50 may be integrally formed, e.g., have a unibody configuration.

As shown in FIGS. 7-8B, expandable member 50 defines a skeletal framework configured to maintain structural integrity of expandable member 50 while under a suction force, e.g., during aspiration of a clot. For example, the skeletal framework may include a tubular lattice-like structure composed of a plurality of interconnected elongated elements, including elongated legs 52, 54 and struts 56. In some examples, expandable member 50 may be formed (e.g., laser-cut) from a single piece of material, such as a nickel-titanium alloy. In other examples, individual elongated elements may be assembled and coupled (e.g., adhered, welded, bonded, etc.) accordingly.

Expandable member 50 includes at least one elongated leg 52 extending in an axial direction (e.g., a longitudinal axis of a particular leg 52 can be substantially parallel to central longitudinal axis 26 of FIG. 2A). Legs 52 may be referred to herein as "slidable legs 52," in that they may be configured to move distally and proximally relative to another portion of catheter 10 (e.g., relative to elongated body 12). For example, similar to prongs 34 of expandable member 18 of FIGS. 1-6B, expandable member 50 may be mechanically coupled to one or more actuation members or pull members 36 (FIGS. 8A-8B) configured to apply a proximal tensile force to a proximal end 52A of slidable legs 52, causing slidable legs 52 to move proximally from their natural or resting configuration in which no external pulling forces are applied to the respective leg 52. Slidable legs 52 may automatically return to their natural or resting configuration (e.g., may move distally) in response to removing the proximal tensile force from the one or more pull members (e.g., due to a natural elasticity of the material of expandable member 50), or in some examples, in response to the application of a distal tensile force to the respective pull members. In some examples, expandable member 50 includes a plurality of slidable legs 52, such as four to six slidable legs 52, disposed circumferentially around central longitudinal axis 26.

In addition to one or more slidable legs 52, expandable member 50 includes a plurality (e.g., two or more) fixed legs 54. For example, expandable member 50 may include as few as two fixed legs 54, or up to as many as double or more of the number of slidable legs 52. In some examples, expandable member 50 may include the same number of fixed legs 54 as slidable legs 52.

Similar to slidable legs 52, each fixed leg 54 may include an elongated structure generally extending in an axial direction, e.g., such that a longitudinal axis of a fixed leg 54 approximately parallel to central longitudinal axis 26 of elongated body 12. However, unlike slidable legs 52, proximal ends 54A of fixed legs 54 may be rigidly coupled to elongated body 12, such that fixed legs 54 are not designed to move proximally or distally with respect to elongated body 12. In some examples, slidable legs 52 and fixed legs 54 may be disposed circumferentially around central longitudinal axis 26 in an alternating pattern such that each slidable leg 52 is located between two fixed legs 54. In some examples, expandable member 50 may include two fixed legs 54 located between each pair of adjacent slidable legs 52, such that each slidable leg 52 includes a fixed leg 54 on either circumferential side. In these examples, immediately adjacent fixed legs 54 may be rigidly coupled to one another in order to distribute a radially expansive force around the circumference of expandable member 50.

Expandable member 50 further includes one or more struts 56 connecting at least one slidable leg 52 to at least one fixed leg 54. Each strut 56 includes an elongated body having a first end 56A that is hingedly connected to one of slidable legs 52, and a second end 56B that is hingedly connected to one of fixed legs 54, wherein the fixed leg 54 is directly adjacent (e.g., not separated by another leg 52 or 54) to the slidable leg 52. In some examples, each strut hinge 58 may be oriented such that first end 56A is located distal to the respective second end 56B. For example, as shown in FIG. 8A, when expandable member 50 is in a contracted configuration, each strut 56 may be oriented at an angle with respect to the slidable leg 52 and the fixed leg 54 to which the respective strut is connected. For example, strut 56 may be oriented so as to define a first acute angle 60A between strut 56 and slidable leg 52, and a first acute angle 61A between strut 56 and fixed leg 54. In some examples, while expandable member 50 is in the contracted figuration, angles 60A and 61A may each be between about 15 degrees and 60 degrees, such as about 30 to 45 degrees, or about 35 degrees. In some examples, angle 60A is 35 degrees and angle 61A is 30 degrees. For angles greater than about 60 degrees, the expandability of expandable member 50 may be restricted in some examples. Strut 56 may also be oriented so as to define a first width w between slidable leg 52 and adjacent fixed leg 54 while expandable member 50 is in a contracted configuration.

As shown in FIG. 8B, in response to a proximal force (indicated by arrow 64) applied to slidable leg 52 via pull member 36, slidable leg 52 may move proximally relative to fixed legs 54. Accordingly, first end 56A of strut 56, which is coupled to slidable leg 52, may also move proximally relative to second end 56B of strut 56, which is coupled to fixed leg 54. The proximal motion of first end 56A of strut 56 causes strut 56 to rotate relative to both slidable leg 52 and fixed leg 54, widening acute angle 60A (FIG. 8A) into angle 60B (FIG. 8B) and widening acute angle 61A (FIG. 8A) into angle 61B (FIG. 8B). In some examples, while expandable member 50 is in the expanded configuration shown in FIG. 8B, angles 60B and 61B may each be between about 70 degrees and 90 degrees, such as about 75 degrees.

During the rotational motion of strut 56, strut 56 may apply a circumferential force between slidable leg 52 and fixed leg 54, causing at least distal end 54B of fixed leg 54 and distal end 52B of slidable leg 52 to move away from one another, thereby widening width w (FIG. 8A) into larger width W (FIG. 8B) between slidable leg 52 and fixed leg 54. When this mechanism is actuated at one or more points around the circumference of expandable member 50, expandable member 50 expands radially outwards (e.g., away from longitudinal axis 26) into an expanded configuration in order to provide additional space for the larger width W between each slidable leg 52 and each adjacent fixed leg 54. This expansion mechanism opens mouth 13 at distal end 12B of elongated body 12 to inner lumen 25, thereby increasing the aspiration potential of catheter 10. The expansion mechanism also enables controlled opening and closing of expandable member 50, potentially improving patient outcomes and care by enabling a clinician to control the opening and closing of expandable member 50 to better engage a clot or other material to be aspirated within a blood vessel or other hollow anatomical structure of a patient. In some examples, control circuitry 8 of FIGS. 1A and 1B may be configured to control the expansion and contraction of expandable member 50. For example, control circuitry 8 may manipulate slidable legs 52 to cyclically expand and contract expandable member 50 according to an expansion frequency or other timing, such as based on a cardiac cycle, a suction frequency, or other frequencies as detailed further below.

In some examples, when in an expanded configuration, struts 56 may be oriented approximately perpendicular or transverse to legs 52, 54 (e.g., angles 60B, 61B may form approximately ninety-degree angles). In other examples, angles 60B, 61B may remain acute angles, e.g., due to expansion tolerances of strut hinges 58.

In some examples, such as the example depicted in FIG. 7, all of slidable legs 52 and fixed legs 54 include rigid elongated structures that are substantially parallel with one another. Accordingly, when expanding into an expanded configuration, expandable member 50 may radially expand by an approximately equivalent distance along its entire length between proximal ends 52A, 54A, and distal ends 52B, 54B, of slidable legs 52 and fixed legs 54, respectively. In other examples, such as the example depicted in FIGS. 8A and 8B, either or both of slidable leg 52 and/or fixed legs 54 may include one or more leg hinges 62, enabling the respective leg to bend or flex at various points along its length, and enabling expandable member 50 to radially expand farther at some points along its length as compared to other points. For example, as shown in FIGS. 8A and 8B, fixed legs 54 each include two leg hinges 62, enabling expandable member 50 to radially expand near a distal end 54B of fixed legs 54, while remaining at a fixed radial distance near a proximal end 54A of fixed legs 54. As shown in FIG. 8A, in some examples, leg hinges 62 may be configured such that, while expandable member 50 is in a contracted configuration, a distal end 54B of legs 54 may be nearer to central longitudinal axis 26 than a proximal end 54A of legs 54 (e.g., width w is smaller near a distal end 54B than near a proximal end 54A. In these examples, expandable member 50 may define a tapered distal tip of catheter 10.

In some examples, such as the example shown in FIG. 7, expandable member 50 includes a "ring" of struts 56, wherein each strut 56 constitutes one of a plurality of struts 56 that extends generally circumferentially around expandable member 50 at a common axial distance along the length of legs 52, 54. In some examples, the struts in each ring can be longitudinally aligned along central longitudinal axis 26. FIG. 7 depicts an expandable member 50 having four rings of struts 56 evenly spaced between the proximal ends 52A, 54A and the distal ends 52B, 54B, of the respective legs. FIGS. 8A and 8B depict an expandable member 50 having two rings of struts 56. In other examples, however, expandable member 50 can include any suitable number of rings of struts 56, such as, but not limited to, one, three, four, or more. In some examples, different struts 56 may include elongated structures having different lengths. For example, a first ring of struts 56 that is located more distally along expandable member 50 may include struts 56 that are longer than struts of a second ring of struts that is proximal to the first ring of struts. This configuration may enable a wider expansion near a distal end of expandable member 50 than near a proximal end, forming a conical shape of expandable member 50 when in an expanded configuration.

In some examples, struts 56 may not be longitudinally aligned. For example, expandable member 50 may include a spiral-type pattern of struts 56 that both wraps circumferentially around expandable member 50, and also advances distally from proximal ends 52A, 54A, toward distal ends

52B, 54B of legs 52, 54, respectively. In these examples, the struts 56 that define the spiral-type pattern may not be longitudinally aligned with each other.

In some examples, expandable member 50 may include one or more curvilinear elements defining a distal rim 66. Rim 66 may include one or more sections of a generally circular shape (or any shape defined by a cross-sectional area of expandable member 50) with each portion affixed to a distal end 52B, 54B of one of legs 52, 54, respectively. In some examples, while in a contracted configuration, adjacent rim portions 66 may contact or nearly contact one another, so as to define a complete circular rim. While in an expanded configuration, expandable member 50 may define a gap between respective rim portions 66.

In some examples, struts 56 may be substantially linear (e.g., linear or linear within manufacturing tolerances). In other examples, such as shown in FIG. 7, struts 56 may be curvilinear so as to conform to a circumference of expandable member 50 when expandable member 50 is in a contracted configuration.

Struts 56 may be coupled to legs 52, 54 via strut hinges 58, which are joints that are configured to enable some relative movement between a strut 56 and respective legs 52, 54. Strut hinges 58 located at a connection point between each of legs 52, 54 and struts 56 may reduce an amount of mechanical stress located at these points and enable expansion of expandable member 50 without the use of significant force and/or without adverse effects to the structural integrity of the connection between struts 56 and legs 52, 54. In some examples, as shown in FIGS. 7-8B, strut hinges 58 may include curved (e.g., C-shaped) extensions of struts 56 (e.g., having a same thickness or cross-sectional area as struts 56), wherein the C-shape is configured to widen or narrow in response to a force applied to its ends via strut 56 and the respective leg 52, 54 to which strut 56 is coupled. In other examples, expandable member 50 may include any appropriate hinge mechanism, such as pin-type hinges typically used with door frames, spring hinges, butterfly-type hinges, etc.

In some examples, rather than expanding in response to a proximal motion of slidable legs 52, expandable member 50 may be configured to contract in response to a proximal motion of slidable legs 52. For example, in some examples, a default (e.g., heat-set) configuration of expandable member 50 may be an expanded configuration. In an opposite mechanism to that described above, a proximal motion of slidable legs 52 (e.g., via pull members 36) may cause struts 56 to rotate to become less transverse to legs 52, 54, applying an inward radial force to legs 52, 54, and causing expandable member 50 to collapse into a contracted configuration. In some examples, expandable member 50 may include both mechanisms. For example, a proximal motion of slidable legs 52 may cause expandable member to initially expand from the contracted configuration into the expanded configuration (e.g., as struts 56 rotate toward a transverse orientation), and then a continued proximal motion of slidable legs 52 may cause expandable member 50 to collapse back into the contracted configuration (e.g., as struts 56 rotate past the transverse orientation). A distal motion of slidable legs 52 (e.g., via pull members 36) may enable this process to run in reverse.

Although depicted in separate figures, the leg-and-strut mechanisms of FIGS. 7-8B may be used in combination with the flexible prong mechanisms of FIGS. 1-6B, such as within a common expandable member of a catheter 10. For example, an expandable member of a catheter may include at least one elongated structure that functions both as a flexible prong 34 as well as a leg 52, 54. In other examples, an expandable member may include both leg-and-strut mechanisms and flexible-prong mechanisms that are mechanically distinct but work in tandem to enable an expansion of the expandable member.

As detailed above with respect to expandable member 18, expandable member 50 may similarly include a flexible membrane 38 (not shown) positioned radially inward of legs 52, 54 and/or radially outward of legs 52, 54. The description of flexible membrane 38 provided with respect to expandable member 18 also applies to expandable member 50.

In some examples of catheter 10, expandable member 18 includes a magnetic material configured to enable the transition of expandable member 18 between an expanded configuration and a contracted configuration. For example, expandable member 18 may include strategically located and oriented regions of magnetic material configured to control or guide a folding of expandable member 18 into a contracted configuration and/or an unfolding of expandable member 18 into an expanded configuration, in response to user actuation of an electromagnetic controller mechanism. In any of the examples of an expandable member 18 including a magnetic material and in which the magnetic force (e.g., attractive or repulsive) of a magnetic material are configured to hold the expandable member in an expanded state, the magnetic forces may be sufficient to hold the expandable material in the expanded state even in the presence of a suction force applied by suction source 4 (FIG. 1A).

Figure 9A:
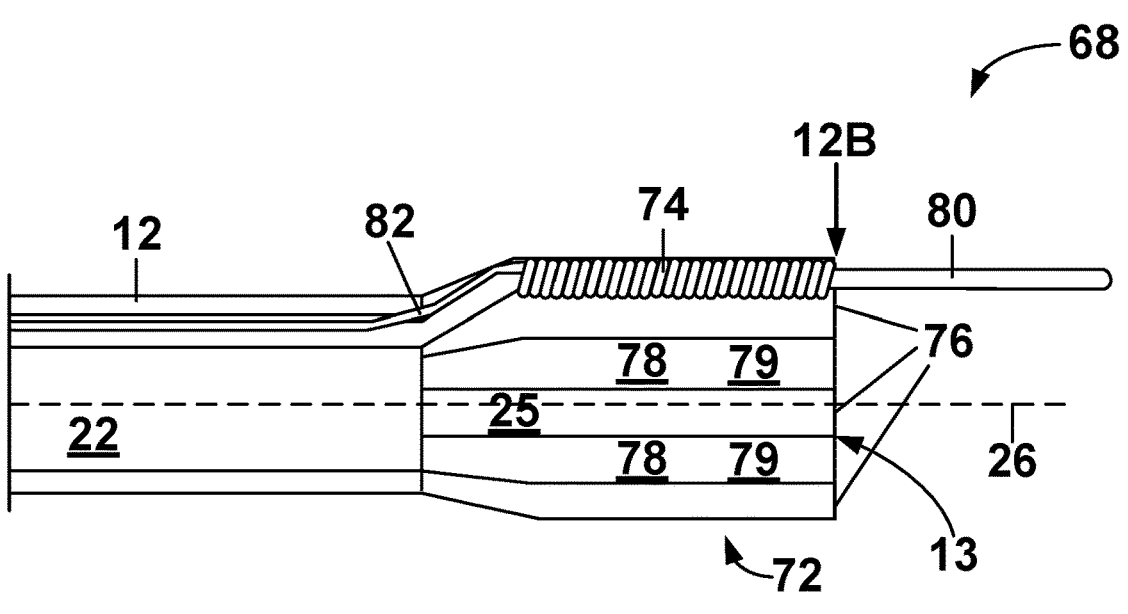
FIG. 9A is a conceptual cross-sectional side view.
Figure 9B:
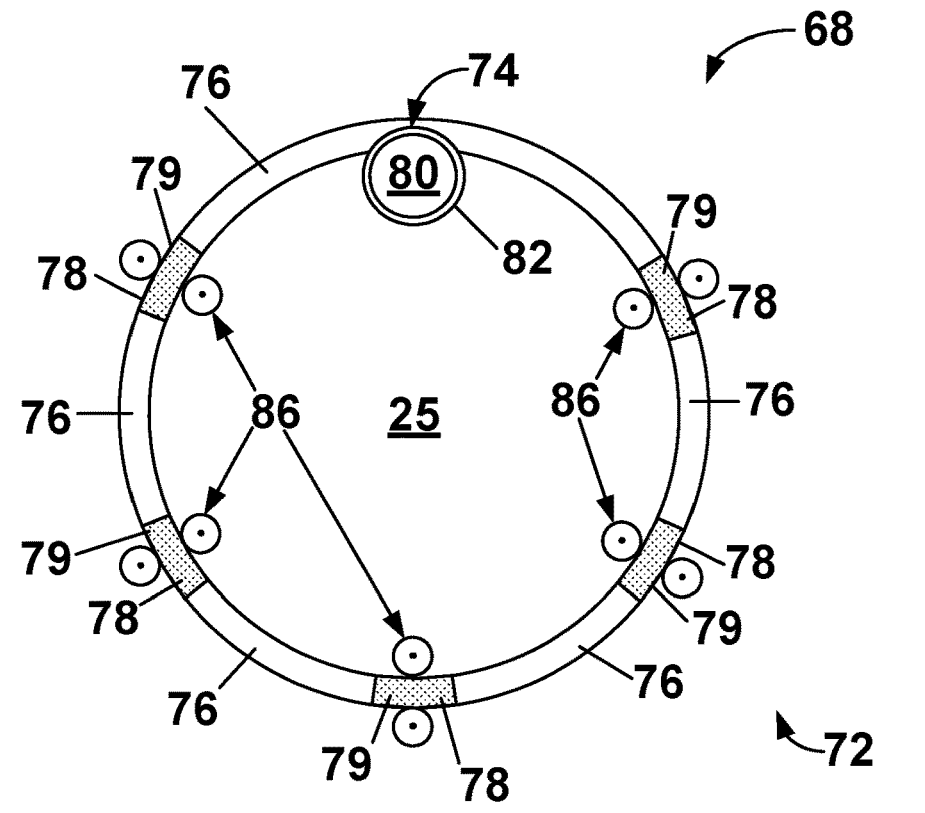
FIG. 9B is a conceptual end view, of another example expandable member of a catheter in an expanded configuration.
Figure 9C:
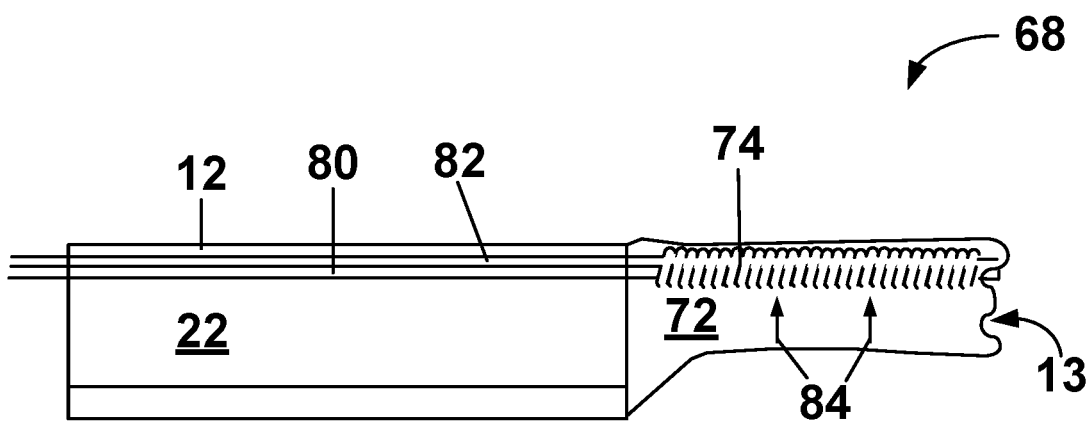
FIG. 9C is a conceptual cross-sectional side view.
Figure 9D:
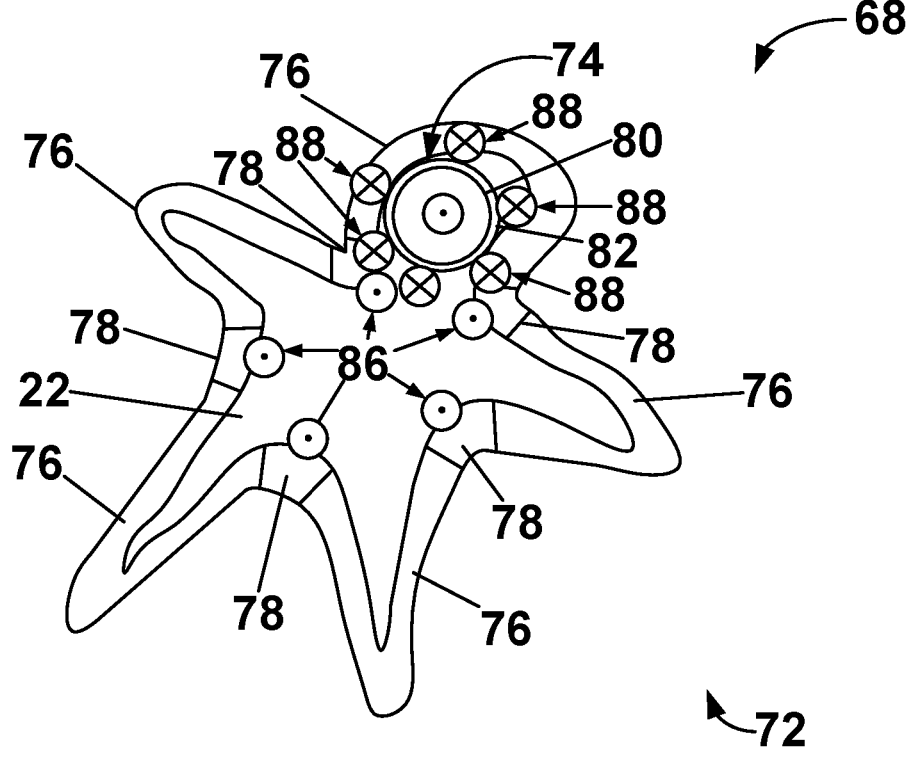
FIG. 9D is a conceptual end view, of the expandable member of FIGS. 9A and 9B in a contracted configuration.

FIGS. 9A-9D depict an example expandable member 68 of catheter 10 (FIG. 2A) that includes a magnetic material. Specifically, FIG. 9A is a conceptual cross-sectional side view of expandable member 68 in an expanded configuration; FIG. 9B is a conceptual end view of expandable member 68 in an expanded configuration; FIG. 9C is a conceptual cross-sectional side view of expandable member 68 in a contracted configuration; and FIG. 9D is a conceptual end view of expandable member 68 in a contracted configuration. Expandable member 68 is an example of expandable member 18 of FIG. 2A. For example, expandable member 68 may be mechanically coupled to structural support member 30, inner liner 28, and/or outer jacket 32 using any of the techniques described with reference to expandable member 18, above.

Expandable member 68 is configured to transition between an expanded configuration (FIGS. 9A and 9B) and a contracted configuration (FIGS. 9C and 9D) at least in response to magnetic attraction and/or repulsion. For example, expandable member 68 may expand and/or contract in response to application, removal, and/or activation of electromagnetic forces internal or external to expandable member 68.

In the example shown in FIGS. 9A-9D, expandable member 68 includes a body structure 72 and a magnetic material 78. In some examples, body structure 72 includes a flexible polymer, e.g., similar to membrane 38 as described above. The polymer may be a single piece of material or one or more discrete polymeric sections 76 connected directly together or interposed with magnetic material 78. For example, body structure 72 can include a plurality of discrete polymer sections 76 arranged in alternating fashion with magnetic material 78 in a circumferential and/or axial direction (e.g., in a direction along longitudinal axis 26 of elongated body 12).

Body structure 72 is depicted in FIGS. 9A and 9B as having a tubular structure (e.g., having a circular cross-sectional area) while in an expanded configuration. In other examples, however, body structure 72 can have another suitable shape having any suitable cross-sectional shape, such as, but not limited to, a non-circular closed geometrical shape.

Magnetic material 78 is coupled to or embedded within body structure 72. In some examples, magnetic material 78 includes a permanent magnetic material, such as a ferromagnetic material that is magnetized to produce its own magnetic field. In other examples, magnetic material 78 may include a ferromagnetic material that responds to an external magnetic field, but that does not generate one on its own.

Magnetic material 78 can have any suitable arrangement within expandable member 68 and relative to body structure 72. In some examples, magnetic material 78 is arranged in one or more discrete sections, such that there are some discrete regions of body structure 72 without magnetic material 78 and, for example, only polymer sections 76 or other non-magnetic structures. For example, the discrete sections of magnetic material may include longitudinal strips 79 oriented axially along body structure 72 (as shown in FIGS. 9A and 9B), one or more ring-shaped regions oriented partially or fully circumferentially around body structure 72, or other discrete shapes within body structure 72 or combinations thereof to define a predetermined pattern of magnetic areas. The discrete sections of magnetic material 78 may include one or more relatively larger, cohesive units of a solid magnetic material, either coupled to or embedded within body structure 72. In other examples, the discrete sections of magnetic material 78 can include a polymer substrate (e.g., a polymer of body structure 72) embedded with magnetic material 78.

In any of the examples of expandable members having magnetic materials described herein, the sections of the expandable member having the magnetic material can be formed separately from and attached to the polymer or other expandable membrane of the body structure, can be formed integrally with the polymer, or can be three-dimensionally printed onto a polymer. For example, magnetic material 78 can be three-dimensionally printed onto a polymer in a desired pattern (e.g., strips 79 or other discrete sections) in the presence of a magnetic to impart certain magnetic orientations) to the resulting sections of magnetic material.

In the example depicted in FIGS. 9A-9D, expandable member 68 includes a body structure 72 defining alternating strips of polymeric material 76 and magnetic strips 79 of a permanent magnetic material 78. Each magnetic strip 79 may extend axially (e.g., parallel to central longitudinal axis 26) and may be distributed circumferentially around body structure 72. In some examples, each magnetic strip 79 may distally extend from a proximal end of expandable member 68 to mouth 13 at distal end 12B of elongated body 12. In other examples, one or more of the magnetic strips may not extend the full axial length of expandable member 68. For example, some or all of the magnetic strips may begin distally of a proximal end of expandable member 68 and/or terminate proximally from distal end 12B. In some examples, one or more of the magnetic strips 79 may include two or more separate magnetic strips that are circumferentially aligned with one another and axially displaced from one another. The example depicted in FIGS. 9A and 9B depicts five magnetic strips 79, however, expandable member 68 may include any number of magnetic strips 79, each strip 79 having virtually any suitable width, measured in a circumferential direction along an outer perimeter of expandable member 68.

In some examples, but not all examples, all of magnetic strips 79 may be oriented such that their magnetic fields all align in a common direction. For example, magnetic strips 79 may be permanent magnets oriented such that their magnetic fields are parallel within a region internal to expandable member 68, for example, within inner lumen 25. In some examples, as indicated by magnetic-field directional indicators 86, the magnetic fields of permanent magnetic strips 79 all point in a distal direction within lumen 25, for example, in a direction toward mouth 13 at distal end 12B of elongated body 12. In other examples, magnetic strips 79 may be oriented such that their magnetic fields all point in a proximal direction within lumen 25. In such examples, the magnetic field of each permanent magnetic strip 79 naturally magnetically repels the magnetic fields of all of the other permanent magnetic strips 79. When no external magnetic field is applied to expandable member 68, the mutual magnetic repulsive force between each pair of permanent magnetic strips 79 imparts an outward radial force onto expandable member 68, holding expandable member 68 in the expanded configuration shown in FIGS. 9A and 9B.

In examples in which catheter 10 includes expandable member 68 including a magnetic material configured to expand radially outward or contract radially inward in response to a magnetic force proximate expandable member 68, an aspiration system including catheter 10 can further include a magnetic device 74 configured to generate the magnetic force (e.g., an external magnetic field). Magnetic device 74 is configured to enable a user or control circuitry 8 to control (e.g., actuate) the expansion and/or contraction of expandable member 68. For example, control circuitry 8 may be configured to cyclically expand and contract expandable member 68 at an expansion frequency or other timing, as detailed further below. Magnetic device 74 may be fixed relative to expandable member 68, or may be movable relative to expandable member 68. In some examples, magnetic device 74 distinct from (e.g., physically separate from and movable relative to) elongated body 12, while in other examples, magnetic device 74 is mechanically connected to elongated body 12 and/or expandable member 68.

In examples in which magnetic device 74 is connected to elongated body 12 and/or expandable member 68, magnetic device 74 may be fixed relative to expandable member 68 in a manner that does not permit movement of magnetic device 74 relative to expandable member 68, or maybe connected to catheter 10 in a manner that enables some relative movement of magnetic device 74 and expandable member 68. In some examples, magnetic device 74 may be external to elongated body 12, while in other examples, magnetic device 74 is positioned internal to elongated body 12, such as within lumen 22 or another lumen, e.g., parallel to lumen 22.

In the example of FIGS. 9A-9D, magnetic device 74 includes an electromagnet, such as a solenoid configured to generate a magnetic field when energy is applied to the solenoid. For example, a rod 80 may be wrapped with a coil of conductive wire 82, so as to create an electromagnet. Rod 80 can be, for example, a guidewire or another elongated structure that is configured to move relative to catheter 10. In these examples, rod 80 may also serve as a guide member that facilitates navigation of catheter 10 through vasculature of a patient. Rod 80 can be, for example, a nitinol wire or a stainless steel wire. In other examples, rod 80 is connected to catheter 10 and a separate guide member may be used to navigate catheter 10 through vasculature. Wire 82 may include any suitable electrically conductive material, such as, but not limited to, gold or copper. In some examples, a portion of conductive wire 82 (e.g., any portion that is not coiled around rod 80) may extend through the entire length of inner lumen 22 of elongated body 12 and into lumen 23 of handle 14 (FIG. 2A) and electrically connected to a power source. In such examples, aspiration system 2A (FIG. 1A) includes a battery or other source of electrical current to pass through conductive wire 82, activating the electromagnetic properties of magnetic device 74, for example, generating a magnetic field within and/or around expandable member 68.

In some examples in accordance with this disclosure, magnetic device 74 may enable expandable member 68 to convert between an expanded configuration (FIGS. 9A and 9B) and a collapsed or contracted configuration (FIGS. 9C and 9D). For example, while magnetic device 74 is deactivated (e.g., no electric current is passing through conductive wire 82), expandable member 68 may be in an expanded configuration, as described above.

As illustrated in FIG. 9D, when magnetic device 74 is activated (via electrical energy) while magnetic device 74 is within lumen 25 or outside of expandable member 70 and longitudinally adjacent to lumen 25, such as by a user actuating user-input device 20 (FIG. 2A), magnetic field 88 is generated around magnetic device 74, oriented or aligned in an opposing direction (e.g., a proximal direction, from the perspective of FIG. 9D) from the magnetic fields 86 of magnetic strips 79. Accordingly, magnetic field 88 may attract the magnetic fields 86 of the magnetic strips 79 of body structure 72. Because the attractive force between magnetic device 74 and magnetic strips 79 is configured to be stronger than the mutual repulsive force between each pair of magnetic strips 79 when magnetic device 74 is activated, activated magnetic device 74 pulls the magnetic material 78 of magnetic strips 79 toward magnetic device 74, causing the outer circumference of body structure 72 to contract inward toward magnetic device 74 (indicated by directional arrows 84 in FIG. 9C), collapsing expandable member 68 into a contracted configuration.

In other examples, instead of or in addition to discrete sections of magnetic material, such as longitudinal strips 79, an expandable member of catheter can include a plurality of relatively smaller particles of magnetic material, such as iron filings or another magnetic material, embedded within a polymer or other substrate of an expandable body structure. The magnetic particles may either include particles of a permanent magnetic material, or may include a ferromagnetic material that has been magnetized to become a permanent magnet. The magnetic material in each section may be oriented such that the section defines a respective magnetic domain where there is a substantially uniform magnetic field (e.g., uniform or functionally uniform).

Figure 10A:
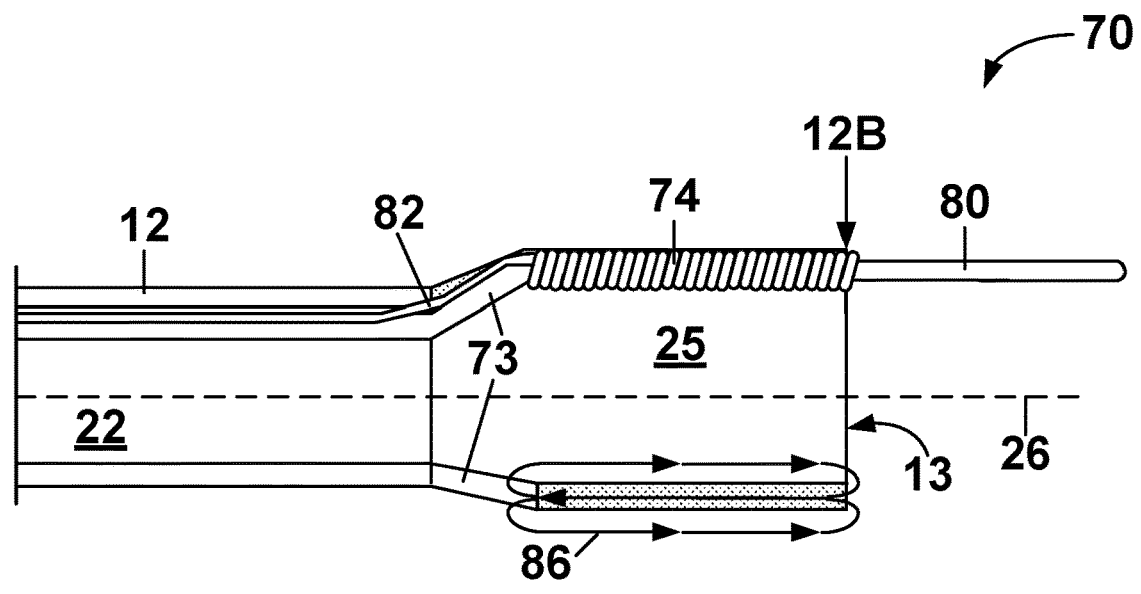
FIG. 10A is a conceptual cross-sectional side view.
Figure 10B:
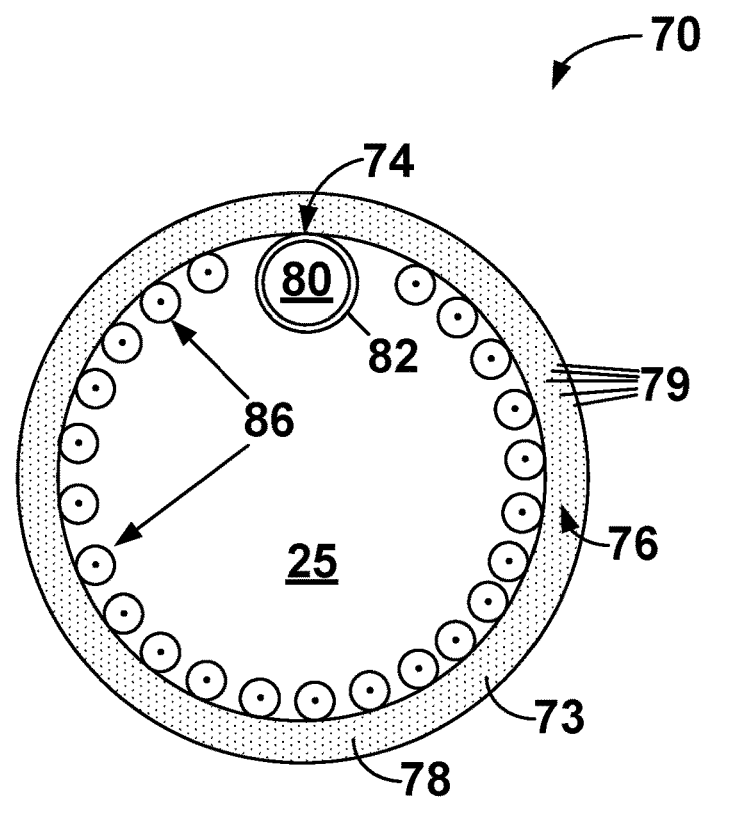
FIG. 10B is a conceptual end view of another example expandable member of a catheter in an expanded configuration.

FIGS. 10A and 10B depict another example expandable member 70 of catheter 10 (FIG. 2A) that includes a magnetic material. Specifically, FIG. 10A is a conceptual cross-sectional side view of expandable member 70 in an expanded configuration, and FIG. 10B is a conceptual end view of expandable member 70 in an expanded configuration.

Similar to expandable member 68 of FIGS. 9A-9D, expandable member 70 is configured to transition between an expanded configuration (FIGS. 10A and 10B) and a contracted configuration at least in response to magnetic attraction and/or repulsion. For example, expandable member 70 may expand and/or contract in response to application, removal, and/or activation of electromagnetic forces internal or external to expandable member 70. The contracted configuration of expandable member 70 may look like the contacted configuration of expandable member 68, e.g., shown in FIGS. 9C and 9D.

In the example shown in FIGS. 10A and 10B, expandable member 70 includes a body structure 73. In some examples, body structure 73 includes a flexible polymer, e.g., similar to membrane 38 and/or body structure 72 described above. The polymer may be embedded, or infused with magnetic material 78. In some examples, body structure 73 consists essentially of a single piece of polymer including magnetic material 78. In other examples, however, body structure 73 can include a plurality of pieces of polymer material mechanically connected together, e.g., via an adhesive, welding, thermal bonding, or the like.

Body structure 73 is depicted in FIGS. 10A and 10B as having a tubular structure (e.g., having a circular cross-sectional area) while in an expanded configuration. In other examples, however, body structure 73 can have another suitable shape having any suitable cross-sectional shape, such as, but not limited to, a non-circular closed geometrical shape.

Magnetic material 78 is coupled to or embedded within body structure 73. In some examples, magnetic material 78 includes a permanent magnetic material, such as a ferromagnetic material that is magnetized to produce its own magnetic field. In other examples, magnetic material 78 may include a ferromagnetic material that responds to an external magnetic field, but that does not generate one on its own.

Magnetic material 78 can have any suitable arrangement within expandable member 70 and relative to body structure 73. In some examples, magnetic material 78 may include a plurality of relatively smaller particles of magnetic material, such as iron filings or another magnetic material, embedded within polymer 76 of body structure 73. The magnetic particles may either include particles of a permanent magnetic material, or may include a ferromagnetic material that has been magnetized to become a permanent magnet. The magnetic material in each section may be oriented such that the section defines a respective magnetic domain. In some examples, all of the magnetic domains of magnetic material 78 of expandable member 70 point in a common direction (e.g., a proximal direction or a distal direction) in the region interior to body structure 73.

As shown in FIGS. 10A and 10B, in some examples, magnetic material 78 may be approximately evenly distributed throughout body structure 73. For example, magnetic material 78 may include a plurality of relatively smaller particles of magnetic material distributed substantially uniformly (e.g., uniformly but for manufacturing tolerances) throughout body structure 73. In any of these examples, all of the individual magnetic particles within body structure 73 may be oriented in or aligned to a common direction, such that the magnetic fields of the individual particles may combine to approximate a common magnetic domain within body structure 72. For example, as indicated by magnetic-field directional indicators 86, the magnetic fields of the magnetic particles of magnetic material 78 all point in a distal direction within lumen 25, for example, in a direction toward mouth 13 at the distal end 12B of elongated body 12. In other examples, magnetic particles of magnetic material 78 may be oriented such that their magnetic fields all point in a proximal direction within lumen 25. In all such examples, the magnetic field of each magnetic particle naturally magnetically repels the magnetic fields of all of the other permanent magnetic particles. The mutual magnetic repulsive force between every pair of permanent magnetic particles imparts an outward radial force onto expandable member 70, holding expandable member 70 in the expanded configuration shown in FIGS. 10A and 10B.

Similar to the example depicted in FIGS. 9C and 9D, expandable member 70 is configured such that when no external magnetic field is applied to expandable member 70, e.g., by magnetic device 74 or another device, expandable member 70 maintains its expanded configuration. When a user introduces (e.g., inserts and/or activates) magnetic device 74 into lumen 25 or outside of lumen 25 (e.g., along an outer surface of expandable member 70), magnetic field 88 of magnetic device 74 magnetically attracts the magnetic field 86 of the magnetic material 78 of body structure 73. Because the attractive force between magnetic device 74 and magnetic material 78 is configured to be stronger than the mutual repulsive force between each pair of magnetic particles, activated magnetic device 74 pulls the magnetic material 78 of body structure 73 toward magnetic device 74, causing the outer circumference of expandable member 70 to contract inward into a contracted configuration.

In another example of expandable member 70, body structure 73 includes an approximately even distribution of magnetic material 78, such as magnetic particles, however the magnetic material 78 is arranged into discrete sections of common magnetic domains. The magnetic domains may be oriented and arranged in a strategic pattern such that some of the magnetic domains magnetically attract other ones of the magnetic domains around the circumference of body structure 73. In the absence of any external magnetic fields or other external forces, the magnetic attractions between various magnetic domains of body structure 73 cause expandable member 70 to collapse into the contracted configuration, similar to the contracted configuration of expandable member 68 shown in FIGS. 9C and 9D. When a user introduces (e.g., inserts and/or activates) magnetic device 74 into lumen 25 or outside of lumen 25 (e.g., along an outer surface of expandable member 70), magnetic field 88 of magnetic device 74 magnetically repels the magnetic domains of body structure 73 having similarly oriented magnetic fields, causing expandable member 70 to expand outward into the expanded configuration shown in FIGS. 10A and 10B.

Figure 11B:
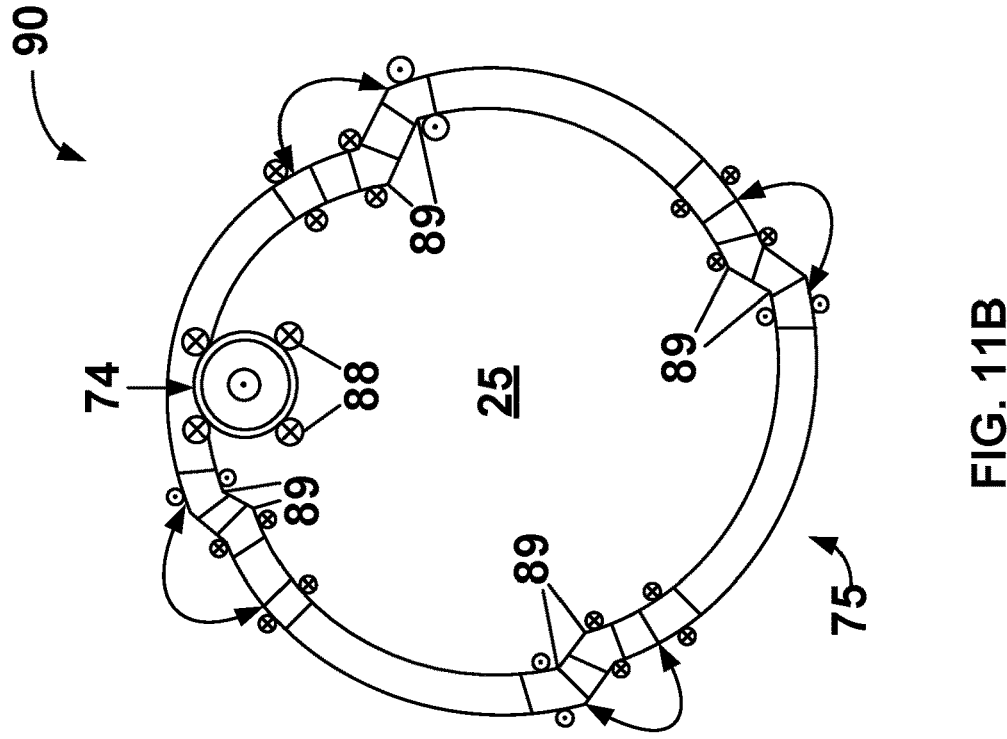
FIG. 11B is a conceptual end view of the expandable member of FIG. 11A in an expanded configuration.
Figure 11A:
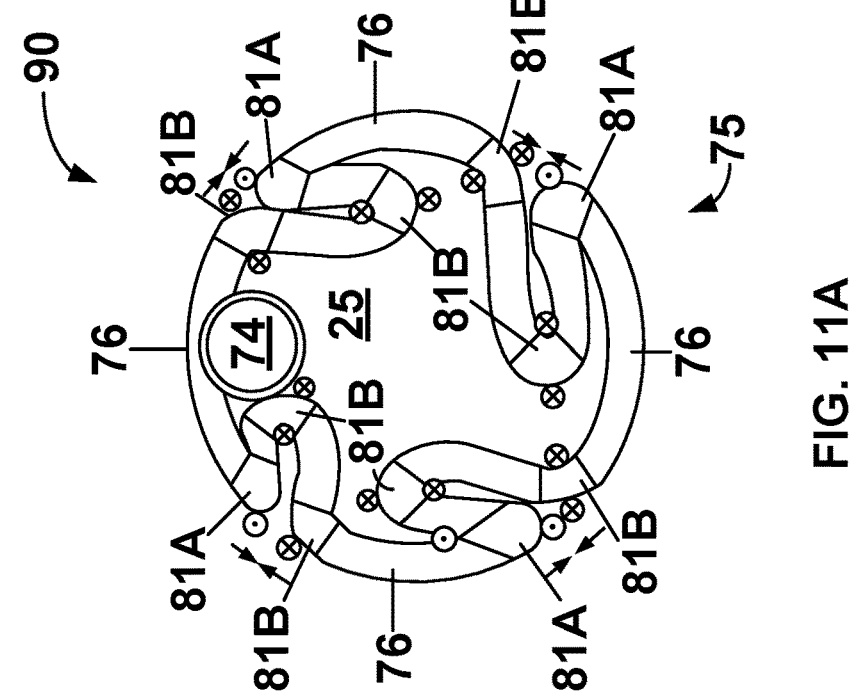
FIG. 11A is a conceptual end view of an example expandable member of a catheter in a contracted configuration.

FIGS. 11A and 11B depict another example expandable member 90 that includes a magnetic material 78 and is configured to expand and contract using the magnetic material 78. Expandable member 90 may be an example of expandable member 68 of FIGS. 9A-9D. Specifically, FIG. 11A is a conceptual end view of an example of expandable member 90 in a contracted configuration, and FIG. 11B is a conceptual end view of the example expandable member 90 of FIG. 11A in an expanded configuration. FIGS. 11A and 11B, as well as the other figures herein, may not be drawn to scale; the positions, sizes, and/or orientations of one or more components of the figures may be altered for purposes of clarifying and illustrating the techniques of this disclosure.

Unlike the example of expandable member 68 shown in FIGS. 9A-9D, in which all of magnetic strips 79 of body structure 72 are oriented such that their magnetic fields 86 are aligned in a common direction, expandable member 90 of FIGS. 11A and 11B includes body structure 75 having magnetic strips 81A, 81B (collectively, "magnetic strips 81") oriented such that two or more of the magnetic strips 81 have magnetic fields that are misaligned or anti-aligned (e.g., anti-parallel), in a strategic pattern. For example, as shown in FIG. 11A, expandable member 90 includes a first plurality of magnetic strips 81A with magnetic fields commonly aligned in a first direction (e.g., parallel to one another), and a second plurality of magnetic strips 81B with magnetic fields commonly aligned in a second direction (e.g., parallel to one another). The first direction may be directionally opposite to (e.g., oriented 180 degrees from) the second direction.

Magnetic strips 81 can each be discrete sections of magnetic material, whether in in the form of sections of substantially magnetic material (e.g., as described with reference to longitudinal strips 79 shown in FIGS. 9A-9D) or a polymer embedded with a magnetic material. Magnetic strips 81 are separated from each other by sections of nonmagnetic material, e.g., sections of polymer 76 not embedded with a magnetic material.

As shown in FIGS. 11A and 11B, magnetic strips 81A each generate a magnetic field pointing in a generally distal direction (e.g., a direction toward a distal end of catheter 10) in the region surrounding (e.g., external to) the strips. Magnetic strips 81B each generate a magnetic field pointing in a generally proximal direction (e.g., a direction toward a proximal end of catheter 10) in the region surrounding (e.g., external to) the strips. Accordingly, distal magnetic strips 81A naturally magnetically attract proximal magnetic strips 81B.

In some examples, expandable member 90 defines one or more folds 89. Folds 89 may be formed into the material of body structure 75, which may be an example of body structure 72, as described above. For example, folds 89 may be heat-set, cut, or sewn, or otherwise permanently integrated into the material of body structure 75, such as into polymeric material 76. Folds 89 may be configured to guide a bending of the material of body structure 75 along a desired direction or into a desired configuration in response to an applied force, e.g., from magnetic strips 81A, 81B repelling each other or attracting each other. In other examples, however, expandable member 90 does not have any predefined folds 89 and is configured to collapse more organically into the contracted configuration.

In some examples, the arrangement of magnetic strips 81A, 81B around the circumference of body structure 75 relative to folds 89 enables expandable member 90 to automatically fold into a contracted configuration while magnetic device 74 is not generating a magnetic field that influences the magnetization of magnetic strips 81A, 81B, e.g., is deactivated and/or removed from lumen 25. For example, as shown in FIGS. 11A and 11B, an arrangement may include groups of three magnetic strips 81, each group including one magnetic strip 81B located between one magnetic strip 81A and one magnetic strip 81B. The example depicted in FIGS. 11A and 11B includes four groups of magnetic strips, however, expandable member 90 may include any number of groups of magnetic strips, as well as other arrangements (e.g., number and/or sequence) of magnetic strips 81 in each group. In response to the magnetic attractions and repulsions between strips 81 within each group, and expandable member 90 may bend along pre-defined folds 89 such that the outer two magnetic strips of each group move toward each other under the force of magnetic attraction, and the middle strip of each group moves radially inward, collapsing expandable member 70 into the contracted configuration shown in FIG. 11A.

When a user activates magnetic device 74, such as by actuating user-input device 20 (FIG. 2A) or other user input device, magnetic device 74 generates a proximally oriented magnetic field (indicated by field indicators 88) in the immediate region external to magnetic device 74 that magnetically attracts distal magnetic strips 81A and magnetically repels proximal magnetic strips 81B. Because expandable member 90 includes more proximal magnetic strips 81B than distal magnetic strips 81A (e.g., twice as many proximal strips 81B as distal strips 81A in each group of strips 81), the net repulsive force between magnetic device 74 and proximal magnetic strips 81B may be stronger than the net attractive force between magnetic device 74 and distal magnetic strips 81A. Additionally or alternatively, due to a relatively large strength of the proximal magnetic field of magnetic device 74, the net repulsive force between magnetic device 74 and proximal magnetic strips 81B is stronger than the attractive force between the outer two magnetic strips of each group of magnetic strips. For at least one of these two reasons, activated magnetic device 74 magnetically repels proximal magnetic strips 81B away from magnetic device 74, such that body structure 75 unfolds, causing expandable member 90 to expand into the expanded configuration shown in FIG. 11B. Expandable member 90 may maintain the expanded configuration while magnetic device 74 is activated proximate expandable member 90 (e.g., close enough for the magnetic field generated by magnetic device 74 to attract magnetic strips 81B).

Figure 12B:
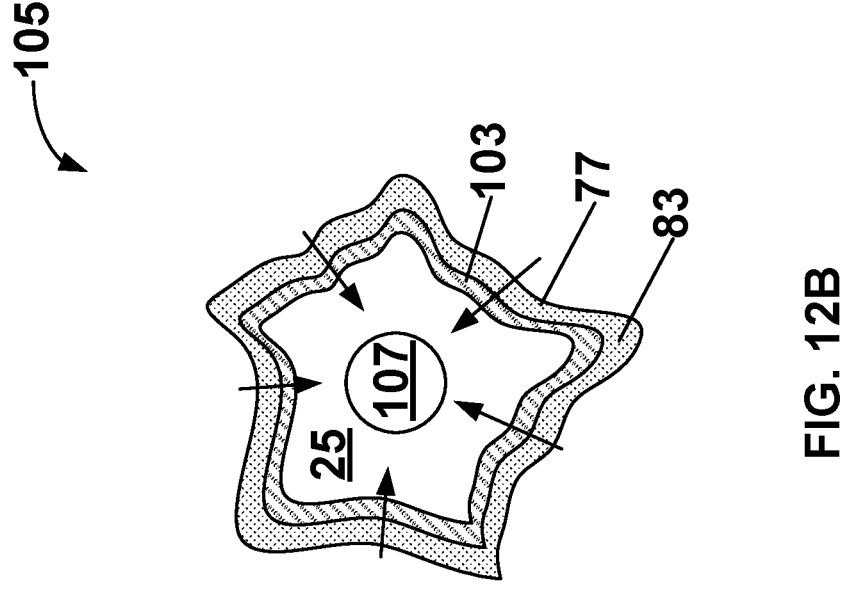
FIG. 12B is a conceptual end view of the expandable member of FIG. 12A in a contracted configuration.
Figure 12A:
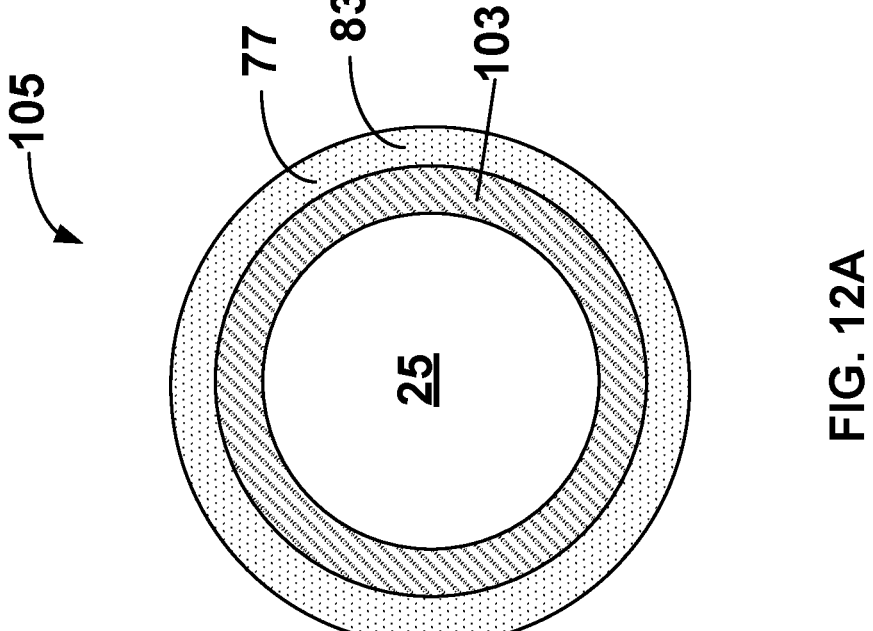
FIG. 12A is a conceptual end view of another example expandable member of a catheter in an expanded configuration.

FIGS. 12A and 12B depict another example expandable member 105, which may be an example of expandable member 70 of FIGS. 10A and 10B. Specifically, FIG. 12A is a conceptual end view of an example of expandable member 105 in an expanded configuration, and FIG. 12B is a conceptual end view of the example expandable member 105 of FIG. 12A in a contracted configuration.

Unlike example expandable members 68, 70, and 90, which include a permanent magnetic material 78 defining one or more permanent magnetic domains, expandable member 105 includes a ferromagnetic material 83 that is configured to react to an external magnetic field, but does not inherently generate a magnetic field of its own. For example, expandable member 105 includes body structure 77, which may be an example of body structures 72, 73, and/or 75, as described above. Body structure 77 includes a ferromagnetic material 83, such as embedded ferromagnetic particles. For example, ferromagnetic material 83 may include such as iron particles or another ferromagnetic material, coupled to or embedded within the material of body structure 77, such as a polymeric material.

Expandable member 105 includes self-expanding structure 103, referred to herein as a self-expanding tube herein, although self-expanding structure 103 can include another shape in other examples. In some examples, self-expanding tube 103 includes a flexible tubular member configured to remain in an expanded configuration in the absence of any applied forces, due to mechanical properties of its composing material. For example, self-expanding tube 103 may self-expand due to an intrinsic material spring mechanism, similar to a self-expanding stent. Self-expanding tube 103 may be located within the inner lumen 25 of expandable member 105, e.g., for example, internal to, and concentric with, body structure 77. Self-expanding tube 103 may fit snugly or tightly within body structure 77 such that its intrinsic expansion mechanism applies an outward radial force onto the interior surface of body structure 77. The outward radial force from self-expanding tube 103 may hold body structure 77 in an expanded configuration, as shown in FIG. 12A.

As shown in FIG. 12B, a user may introduce a magnet 107 into the inner lumen 25 of expandable member 105. Magnet 107 may be an example of magnetic device 74 described above. In some examples, magnet 107 may include a permanent magnet rigidly fixed to the end of an elongated structure, such as a guidewire. In other examples, magnet 107 may include an electromagnet, such as an electromagnetic solenoid as described above. In some examples, the user may manually feed magnet 107 distally through the lumen 22 of elongated body 12 and into lumen 25 of expandable member 105. In other examples, the user may actuate user-input device 20 (FIG. 2A) to distally insert magnet 107 into, and proximally retract magnet 107 from, lumen 25 of expandable member 105. When magnet 107 is positioned in lumen 25 of expandable member 105, magnet 107 magnetizes the ferromagnetic material 83 of body structure 77, magnetically attracting material 83 toward magnet 107. The magnetic attractive force pulls the circumference of body structure 77 radially inward, forcing expandable member 105 to collapse, as shown in FIG. 12B. For example, the magnetic attraction between magnet 107 and the ferromagnetic material 83 of body structure 77 may be stronger than the outward radial pressure from self-expanding tube 103, overcoming the outward radial pressure from self-expanding tube 103 and collapsing expandable member 105 into the contracted configuration shown in FIG. 12B.

Figures 13A, 13B:
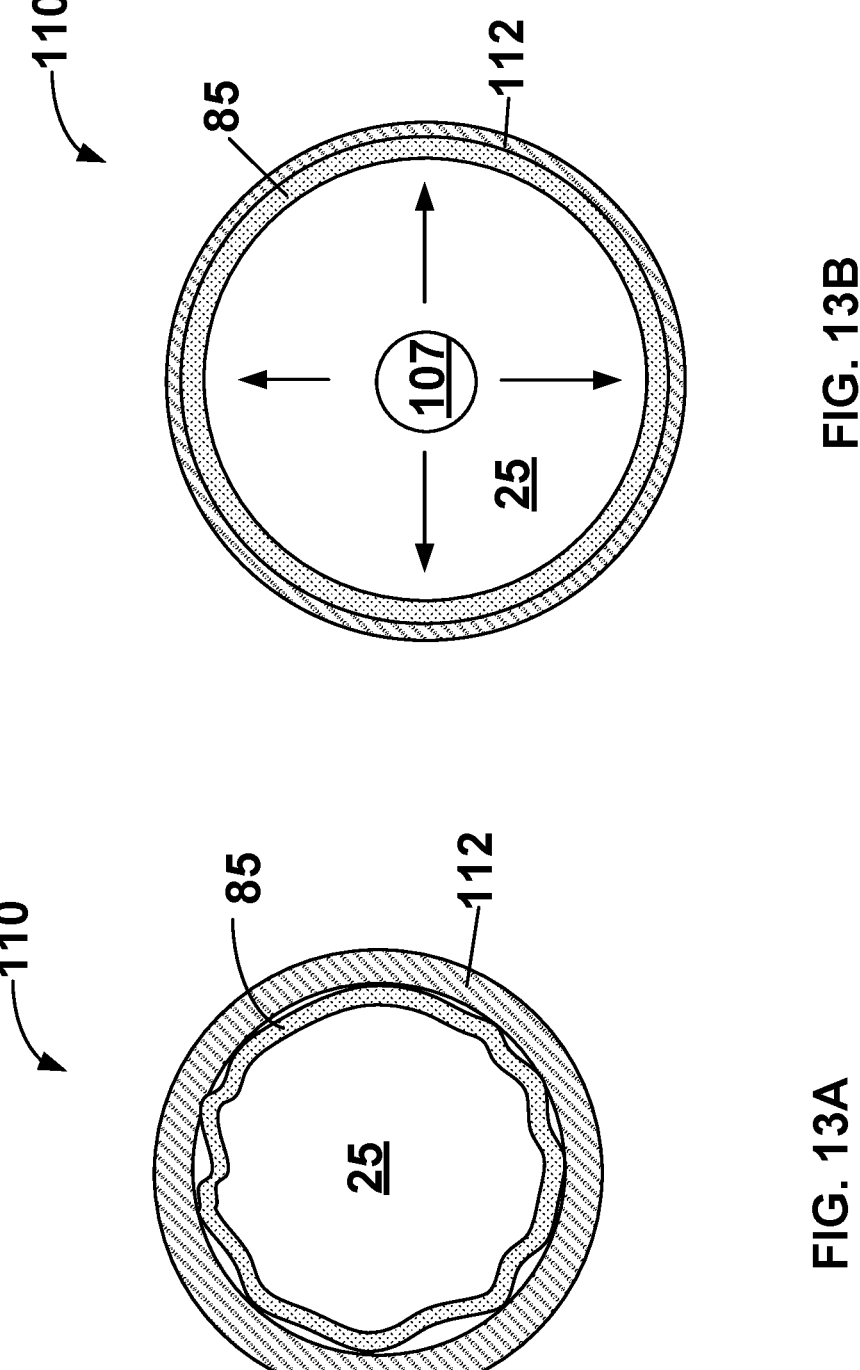
FIG. 13A is a conceptual end view of another example of expandable member in a contracted configuration.
FIG. 13B is a conceptual end view of the expandable member of FIG. 13A in an expanded configuration.

FIGS. 13A and 13B depict another example expandable member 110, which may be an example of expandable member 105 of FIGS. 12A and 12B. Specifically, FIG. 13A is a conceptual end view of an example of expandable member 110 in a contracted configuration, and FIG. 13B is a conceptual end view of the example expandable member 110 of FIG. 13A in an expanded configuration.

Unlike example expandable member 105 of FIGS. 12A and 12B, in which body structure 77 includes (non-permanent) ferromagnetic particles, expandable member 110 of FIGS. 13A and 13B includes body structure 85 having embedded permanent magnetic particles, similar to example expandable member 70 of FIGS. 10A and 10B. Permanent magnetic particles may be distributed around the entire circumference of body structure 85, which may be an example of body structures 72, 73, 75, and/or 77. In some examples, the permanent magnetic particles of body structure 85 are commonly oriented such that their intrinsic magnetic fields all repel each other, holding body structure 85 in an expanded configuration in the absence of any external forces.

Expandable member 110 includes self-contracting tube 112. Self-contracting tube 112 may be an example of self-expanding tube 103 of expandable member 105. For example, the intrinsic spring properties of the materials of both self-expanding tube 103 and self-contracting tube 112 may be configured to resist both compressive and expansive forces, and remain in a generally tubular structure in the absence of external forces. For example, self-contracting tube 112 may self-contract due to an intrinsic material spring mechanism. Self-contracting tube 112 may be located external to, and concentric with, body structure 85, such that body structure 85 is located within an inner lumen of self-contracting tube 112. Self-contracting tube 112 may fit snugly or tightly around body structure 85 such that its internal contraction mechanism applies an inward radial force to the exterior surface of body structure 85. For example, the inner diameter of self-contracting tube 112 may be smaller than the outer diameter of body structure 85, such that the inward radial force from self-contracting tube 112 may hold body structure 85 in a contracted configuration, as shown in FIG. 13A. For example, the inward radial force from self-contracting tube 112 may be stronger than the outward radial force of magnetic repulsion intrinsic to the permanent magnetic material of body structure 85, such that self-contracting tube 112 causes body structure 85 to partially or fully collapse into the contracted configuration of FIG. 13A.

As shown in FIG. 13B, a user may introduce a magnet 107 into the inner lumen 25 of expandable member 110. In some examples, magnet 107 may include a permanent magnet rigidly fixed to the end of an elongated structure, such as a guidewire. In other examples, magnet 107 may include an electromagnet, such as an electromagnetic solenoid as described above. In some examples, the user may manually feed magnet 107 distally through the lumen 22 of elongated body 12 and into lumen 25 of expandable member 110. In other examples, the user may actuate user-input device 20 (FIG. 2A) to distally insert magnet 107 into, and proximally retract magnet 107 from, lumen 25 of expandable member 110.

Magnet 107 may generate a magnetic field oriented in the same direction as the magnetic field of the permanent magnetic material of body structure 85, such that magnet 107 magnetically repels body structure 85 upon entering lumen 25 of expandable member 110. The magnetic repulsion force pushes the circumference of body structure 85 radially outward, forcing expandable member 110 to expand. For example, the magnetic repulsion between magnet 107 and the magnetic material of body structure 85 is stronger than the inward radial pressure from self-contracting tube 112, overcoming the inward radial pressure from self-contracting tube 112 and expanding expandable member 110 into the expanded configuration shown in FIG. 13B.

Figure 14:
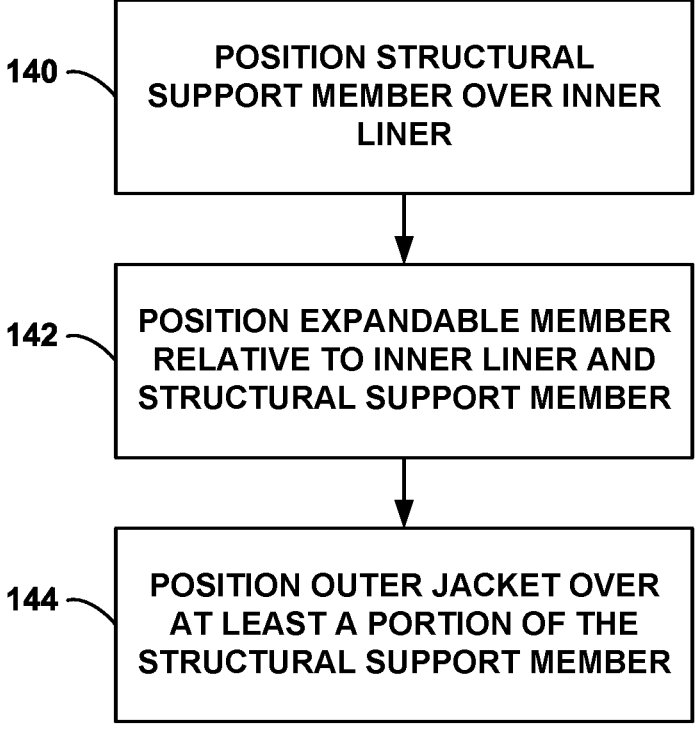
FIG. 14 is a flow diagram of an example method of forming a catheter.
Figure 15:
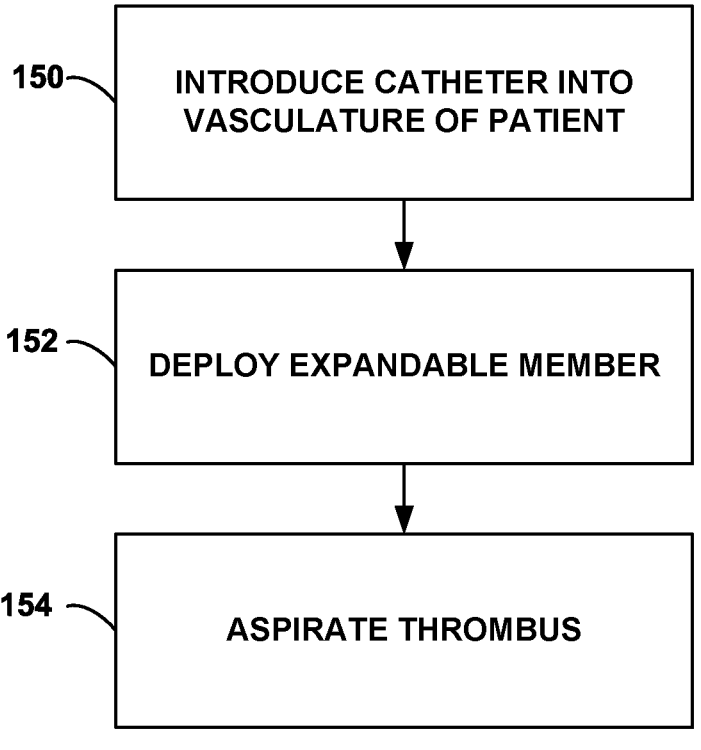
FIG. 15 is a flow diagram of an example method of using a catheter.

Catheters described herein may be formed using any suitable technique and can be used in any suitable medical procedure. FIGS. 14 and 15 describe example techniques for making and using, respectively, the catheters described herein. The techniques of FIGS. 14 and 15 are described with reference to the various aspects of aspiration system 4A of FIG. 1A and catheter 10 of FIGS. 1A-2B for illustrative purposes, however, such descriptions are not intended to be limiting. The technique of FIG. 14 may be used to form other catheters, or catheter 10 of FIGS. 1A-2B may be formed using techniques other than those described with reference to FIG. 14. Similarly, the technique of FIG. 15 may be used with other aspiration systems (e.g., aspiration system 2B of FIG. 1B) and/or catheters, or aspiration system 2A and/or catheter 10 of FIGS. 1A-2B may be used using techniques other than those described with reference to FIG. 15.

FIG. 14 is a flow diagram of an example method of forming catheter 10. The technique of FIG. 14 includes positioning structural support member 30 over inner liner 28 (140). In some examples, inner liner 28 is a tubular body and is placed on a mandrel prior to structural support member 30 being positioned over inner liner 28. Inner liner 28 may be fabricated using any suitable technique, such as by extrusion. In some examples, after positioning inner liner 28 over the mandrel, inner liner 28 may be heat shrunk onto the mandrel such that inner liner 28 conforms to the outer surface of the mandrel and acquires the profile of the mandrel. In other examples, however, heat shrinking may not be necessary. For example, in addition to, or instead of, heat shrinking, inner liner 28 may be longitudinally stretched over the mandrel in order to substantially conform to the outer surface of the mandrel.

Once inner liner 28 is positioned on the mandrel, structural support member 30 (e.g., a coil, a braid, or combinations thereof) may be positioned over inner liner 28 (140). For example, structural support member 30 may include one or more wire elements (e.g., flat wires, flat-round wires, or round wires) coiled or woven over inner liner 28, or precoiled or pre-woven and subsequently positioned over inner liner 28. Next, expandable member 18 may be positioned relative to inner liner 28 (e.g., over a portion of inner liner 28 or distal to inner liner 28) and structural support member 30 (142). In some examples, expandable member 18 is coupled to structural support member 30. For example, where expandable member 18 and structural support member 30 are each formed independently of one another, the proximal end of expandable member 18 may be joined to the distal end of structural support member 30 via welding, brazing, soldering, epoxy, mechanical hooks, or other suitable techniques. In other example, expandable member 18 may not be directly connected to structural support member 30 and may be held in place relative to each other via inner liner 28 and outer jacket 32.

In other examples, structural support member 30 and expandable member 18 may be integrally formed such that additional coupling is not necessary. For example, catheter 10 may include a hypotube that is cut to form all or a portion of structural support member 30 and expandable member 18 such that the two components are integrally formed from the same hypotube. The hypotube may then be stretched and positioned over inner liner 28. In other examples, structural support member 30 and expandable member 18 may both be formed using metal wires wherein structural support member 30 and expandable member 18 represent different structures (e.g., coil vs weave) formed by the wires.

In some examples, the structural configuration of structural support member 30 and/or expandable member 18 may be at least partially defined prior to being positioned over inner liner 28. For example, a shape memory wire (e.g., Nitinol alloy) or other structure of an otherwise heat-settable metal, alloy, or polymer base may be formed over a different mandrel where the structure is heat set to define a desired shape of structural support member 30 and/or expandable member 18. After being heat set, structural support member 30 and/or expandable member 18 may then be subsequently removed from the mandrel, and then repositioned over inner liner 28.

In some examples, defining some or all of the structural characteristics of structural support member 30 and/or expandable member 18 prior to positioning the structure over inner liner 28 may help control the structural characteristics of structural support member 30 and/or expandable member 18 (e.g., gap spacings, pitch, expansion characteristics, or the like), as well as control product consistency and uniformity of structural support member 30 and/or expandable member 18 for use in multiple catheters. In addition, shape-setting of the metal structures on a separate, heat-resistant mandrel enables the construction of the elongated body 12 without damaging inner liner 28.

Structural support member 30 and expandable member 18, where applicable, may be secured in place relative to inner liner 28 using any suitable technique. For example, structural support member 30 may be adhered to inner liner 28. In some examples, an adhesive may be positioned over inner liner 28 prior to positioning structural support member 30 over inner liner 28. In addition to, or instead of, an adhesive, outer jacket 32 may be used to secure portions of structural support member 30 and expandable member 18 to inner liner 28.

The technique of FIG. 14 also includes positioning outer jacket 32 over inner liner 28 and structural support member 30 (144). For example, the one or more sections forming outer jacket 32 may be independently formed (e.g., extruded) and slid over inner liner 28, structural support member 30, and, in some examples, expandable member 18 in the desired arrangement. Outer jacket 32 may be connected to inner liner 28 using any suitable technique. For example, outer jacket 32 may be heat shrunk over inner liner 28. A suitable technique for connecting outer jacket 32 to inner liner 28 may include, heating outer jacket 32 while outer jacket 32 is in heat shrink tubing enough to cause the material of outer jacket 32 to melt, then reflow the material of outer jacket 32. In some examples, the heat shrinking of outer jacket 32 may help secure the respective positions of structural support member 30 and/or expandable member 18 along elongated body 12. This may help minimize the wall thickness of elongated body 12 and, therefore, increase the inner diameter of elongated body 12 for a given outer diameter by limiting the inclusion of addition layer within the wall construction of elongated body 12. In addition, the absence of additional layers (e.g., an adhesive/tie/support layer) that joins inner liner 28 to outer jacket 32 may contribute to an increased flexibility of catheter 10. In some examples, during the heat-shrink process, the various sections of outer jacket 32 may also be bonded (e.g., fused) together.

FIG. 15 is a flow diagram of an example method of aspiration using catheter 10. In accordance with the technique shown in FIG. 15, a clinician introduces catheter 10 into vasculature of a patient (150) and navigates catheter 10 to a target treatment site within a patient. In some examples, the clinician navigates catheter 10 to the target site with the aid of a guidewire, guide catheter or another guide member. For example, catheter 10 may be advanced over a guidewire to the target treatment site. Additionally, or alternatively, the clinician may introduce catheter 10 into vasculature of a patient through a guide catheter that has been initially introduced into vasculature of the patient.

Once adjacent a target treatment site, expandable member 18 may be deployed from a collapsed configuration to an expanded configuration within the vasculature (152) either manually by a user or automatically or otherwise under the control of control circuitry 8 (FIGS. 1 and 2A), e.g., as described with reference to FIG. 16. For example, when distal end 12B of elongated body 12 is positioned as desired relative to a target treatment site, the user may actuate one or more pull members 36 or control circuitry 8 may cause pull members 36 to be actuated in order to radially bend a set of flexible prongs 34 (FIGS. 1-6B) of expandable member 18. Additionally or alternatively, the user may actuate one or more pull members 36, or control circuitry 8 may cause pull members 36 to be actuated in order to reorient two or more circumferential struts 56 of example expandable member 50 of FIGS. 7-8B. In other examples, expandable member 18 can be configured to expand in response to actuation members other than or in addition to pull members 36.

Additionally or alternatively, control circuitry 8, automatically or based on input from a user received via user input device 20 (FIG. 2A), may deactivate magnetic device 74 in order to remove a magnetic attractive force acting upon a set of permanent magnetic strips 79 or magnetic material 78 of example expandable member 68 (FIGS. 9A-9D) and expandable member 70 (FIGS. 10A and 10B). Additionally or alternatively, control circuitry 8, automatically or based on input from a user received via user input device 20, may actuate magnetic device 74 in order to magnetically repel one or more permanent magnetic strips 81B of example expandable member 90 (FIGS. 11A and 11B). Additionally or alternatively, the user or control circuitry 8 may proximally withdraw magnet 107 in order to remove a magnetic attractive force acting upon body structure 77 of example expandable member 105 (FIGS. 12A and 12B) to cause expandable member 105 to expand radially outward. Additionally or alternatively, the user or control circuitry 8 may proximally insert magnet 107 in order to apply a magnetic repulsive force acting upon body structure 85 of example expandable member 110 (FIGS. 13A and 13B) to cause expandable member 110 to expand radially outward.

After mouth 13 of catheter 10 is positioned as desired proximate a thrombus in the vasculature, control circuitry 8, alone or based on input from a user received via user input device 20, controls suction source 4 to apply a suction force to lumens 22, 25 of catheter 10 to aspirate the thrombus from the vasculature via the lumens 22, 25 (154).

In some, but not all, examples, control circuitry 8 is configured to control a cyclical expanding and contracting of expandable member 18 between the contracted and expanded configurations according to an expansion frequency and while expandable member 18 is in the vasculature of the patient proximate a thrombus, which may improve the outcome of an aspiration procedure. The expansion frequency can be a fixed frequency over a period of time (e.g., a treatment session) or can vary over the period of time.

Figure 16:
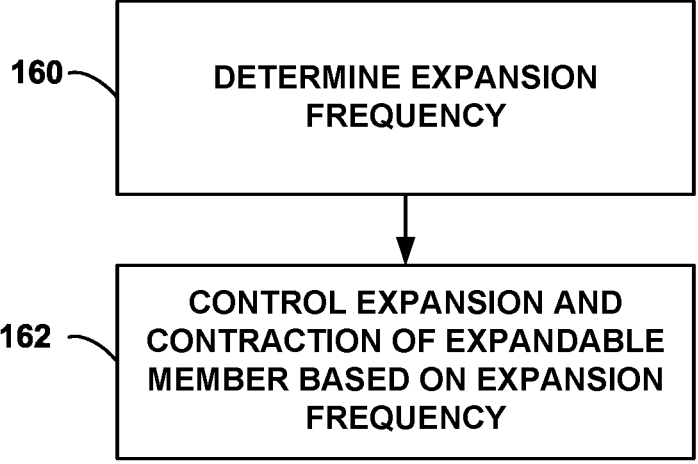
FIG. 16 is a flow diagram of an example method of expanding an expandable member of a catheter.

FIG. 16 is a flow diagram of an example method of controlling expandable member 18 according to an expansion frequency. The method of FIG. 16 is primarily described with reference to aspiration system 2A of FIG. 1A and expandable member 18 of FIGS. 2A and 2B, but can be used with any suitable aspiration system and/or any of the expandable members described herein. In addition, any or all of the technique shown in FIG. 16 may be performed by control circuitry of another device in addition to or instead of control circuitry 8 of aspiration system 2A.

In accordance with the technique shown in FIG. 16, control circuitry 8 determines an expansion frequency for expanding and contracting expandable member 18 (160), and then controls the expansion and contraction of expandable member 18 based on the determined expansion frequency (162). The expansion frequency can be, for example, the frequency with which control circuitry 8 controls expandable member 18 to move between a fully or partially expanded configuration and a less expanded configuration or a fully collapsed configuration. In some examples, the expansion frequency indicates the number of times expandable member 18 is in the expanded configuration or the contracted configuration per unit of time. For ease of description, the expansion frequency is primarily referred to describe the timing with which control circuitry 8 causes expandable member 18 to move between an expanded configuration and a contracted configuration. The "expanded" configuration can be a fully expanded or a partially expanded configuration, and the "contracted" configuration can be a less expanded state (e.g., a fully contracted configuration or a partially contracted configuration). In some examples, the expansion frequency of expandable member 18 may be between about 0.5 Hz and about 30 Hz, such as about 1 Hz to about 15 Hz, or about 5 Hz to about 10 Hz. As some non-limiting examples, the expansion frequency may be about 1 Hz, about 5 Hz, about 10 Hz, or about 15 Hz, according to one or more of the examples detailed further below. In some examples, 1 Hz may correspond to a cardiac cycle of some patients.

It is believed that cyclically controlling the expansion and contraction of expandable member 18 according to a particular expansion frequency may more quickly and/or more effectively remove a thrombus from a blood vessel of a patient by varying an amount of suction force applied to the thrombus. For example, a more-expanded configuration of expandable member 18 increases cross-sectional area of mouth 13 of catheter 10 (the cross-section being taken in a direction orthogonal to longitudinal axis 26 of elongated body 12), which may result in a greater amount of suction force (from suction source 4) being applied to an outer surface of the thrombus proximate mouth 13 compared to the suction force applied when expandable member 18 is a more-contracted configuration. Control circuitry 8 can cause expandable member 18 to move between the expanded and contracted configurations according to the expansion frequency while suction source 4 (FIG. 1A) is applying a steady-state, constant or substantially constant suction force (referred to herein as non-cyclic aspiration) to lumen 22 of catheter 10 or while suction source 4 is modifying the suction force (referred to herein as cyclic aspiration) to lumen 22 of catheter 10. In any of these examples, the expansion frequency can be fixed or control circuitry 8 can change the expansion frequency over time (e.g., during an aspiration procedure).

Control circuitry 8 can determine the expansion frequency (160) using any suitable technique. As some non-limiting examples, control circuitry 8 may determine the expansion frequency based on user input, based on a value stored in memory 9 (FIGS. 1A and 1B) or a memory of another device, based on a natural frequency (e.g., a resonant frequency) of a thrombus, based on a cardiac cycle of a patient, and/or based on a suction frequency of a suction source 4. In cyclic aspiration examples, the suction frequency of suction source 4 is the frequency with which suction source 4 cycles the suction force between a relatively high suction force and a relatively low suction force. In some examples, the suction frequency is modified by control of only a pump (if present) of suction source 4, of only the evacuation volume, or of only pulsator 7 (if present), or of any combination of those components. The suction frequency can be determined using any suitable technique, such as based on user input, based on the natural frequency (e.g., resonant frequency) of a thrombus, or based on a cardiac cycle of a patient.

In some examples, control circuitry 8 determines the expansion frequency (160) by at least receiving user input indicating the expansion frequency via user-input device 20 or another user input mechanism. For example, user-input device 20 or another user input mechanism can include a button, a keypad, a touchscreen, a microphone configured to receive voice commands, or the like, through which the user can input a selected expansion frequency. In some examples, control circuitry 8 is configured to receive user input selecting an expansion frequency from a plurality of predetermined expansion frequencies (e.g., stored by memory 9 of aspiration system 2A or a memory of another device). In these examples, user-input device 20 may include a display, a rotating dial, or the like that presents the predetermined expansion frequencies to the user, from which the user can select one or more expansion frequencies for controlling the expansion of expandable member 18. In addition to or instead of determining the expansion frequency based on user input, in some examples, control circuitry 8 is configured to receive user input indicating a desired expansion frequency value.

In some examples, sensing circuitry 11 is configured to detect a natural frequency (e.g., a resonant frequency) of a clot within the patient's vasculature. As one example, the natural frequency of the clot may be between about 5 Hz and 10 Hz. In such examples, control circuitry 8 may determine the expansion frequency of expandable member 18 (160) based the signal generated by sensing circuitry 11 and indicative of the natural frequency of the clot. The contact between a thrombus and the vasculature in which the thrombus is positioned may include certain properties such that, when the suction force with which aspiration system 2A aspirates the thrombus is periodically modified according to a particular frequency, the thrombus may more effectively become dislodged and aspirated into lumens 22, 25 of catheter 10.

In other examples, the expansion frequency is predetermined. In these examples, control circuitry 8 may determine the expansion frequency (160) by retrieving the predetermined expansion frequency from memory 9 or a memory of another device and without any user input indicating the expansion frequency.

In addition to or instead of any of the other previous examples for determining an expansion frequency, in some examples, control circuitry 8 is configured to determine the expansion frequency (160) based on a cardiac cycle of a patient. It is believed that coordinating the extent to which expandable member 18 is expanded with the cardiac cycle may impact the amount of suction force applied to thrombus proximate mouth 13. For example, synchronizing the expansion, or the attainment of the expanded state of, expandable member 18 with certain parts of the cardiac cycle (e.g., diastole or systole) may more quickly and more effectively remove a thrombus from a blood vessel of a patient than applying a continuous or steady suction force, or other forms of cyclic aspiration.

A cardiac cycle includes different phases, such as diastole, during which the heart muscles are relaxed and a heart chamber fills with blood, and systole, during which the heart muscles contract and pump blood out of the heart chamber. For example, in a patient with a healthy heart, atrial systole occurs during ventricular diastole to actively fill the ventricles during their diastole. In some examples, the phases of a cardiac cycle can include cardiac diastole, atrial systole, and ventricular systole. Atrial systole can be associated with a P-wave of a PQRST complex of an electrical cardiac signal, such as a cardiac electrogram (EGM) or electrocardiogram (ECG), and ventricular systole can be associated with a Q-deflection of the PQRST complex of the electrical cardiac signal. Systole referenced herein may refer to atrial systole or ventricular systole. In addition, diastole referenced herein may refer to atrial diastole or ventricular diastole. In addition to or instead of these phases, the phases of a cardiac cycle can be described by the fluid flow in the heart. As an example, the phases of a cardiac cycle can be referred to as isovolumetric relaxation, ventricular filling, ventricular filling with atrial systole, isovolumetric contraction, and ejection.

In some examples, control circuitry 8 may first determine (e.g., measure, detect, or receive from another device) a cardiac cycle of the patient, and then determine the expansion frequency of expandable member 18 based on the cardiac cycle. For example, control circuitry 8 can select the expansion frequency such that expandable member 18 is in its expanded configuration at certain parts of the cardiac cycle (e.g., systole or diastole) and in its contracted configuration at other parts of the cardiac cycle (e.g., the other of systole or diastole). In these examples, as well as other examples described herein, the expansion frequency changes over time (e.g., heartbeat to heartbeat, or every few heartbeats) as the cardiac cycle of the patient changes (e.g., becomes shorter or faster, or speeds up or slows down over time. As one example, the cardiac cycle of the patient at one point in time may be on the order of 60 beats per minute (bpm). In some such examples, control circuitry 8 may select the expansion frequency to be on the order of about 1 Hz.

Control circuitry 8 of aspiration system 2A can determine a cardiac cycle (e.g., the current phase of a cardiac cycle) using any suitable technique. For example, control circuitry 8 can determine a current phase of a cardiac cycle of a patient based on an electrical cardiac signal, a blood pressure, blood oxygen saturation, or another physiological parameter that changes as a function of a cardiac cycle of the patient. In some examples, aspiration system 2A includes or is otherwise communicatively coupled to sensing circuitry 11 configured to generate a signal indicative of a physiological parameter of the patient indicative of the cardiac cycle, and control circuitry 8 is configured to receive the signal and determine the cardiac cycle (e.g., a specific phase of the cardiac cycle) based on the signal. The signal can include, for example, one or more of an ECG, an EGM, a photoplethysmogram (PPG), a heart sound phonocardiogram, or a blood pressure signal. Sensing circuitry 11 can include, for example, one or more of an electrocardiogram sensor, an electrogram sensor, a blood oxygen saturation sensor, or an arterial blood pressure sensor.

In addition to or instead of receiving physiological signals from sensing circuitry 11, in some examples, control circuitry 8 may receive signals from another device that determines the current part of the cardiac cycle and transmits the determined part of the cardiac cycle to control circuitry 8. Thus, although not shown in FIG. 1A, in some examples, aspiration system 2A includes communication circuitry configured to receive information from another device. The communication circuitry may be operable to communicate with external devices via one or more networks by transmitting and/or receiving network signals on the one or more networks. For example, control circuitry 8 may use the communication circuitry to transmit and/or receive radio signals on a radio network such as a cellular radio network, or on a satellite network. Examples of such communication circuitry include a network interface card (e.g. such as an Ethernet card), an optical transceiver, a radio frequency transceiver, or any other type of device that can send and/or receive information. Other examples of communication circuitry may include Near-Field Communications (NFC) units, Bluetooth® radios, short wave radios, cellular data radios, wireless network (e.g., Wi-Fi®) radios, as well as universal serial bus (USB) controllers.

In some examples, control circuitry 8 may determine the expansion frequency (160) based on an operating frequency of a suction source, such as a suction frequency of suction source 4 of aspiration system 2A. It is believed that in some cases, controlling and/or varying the amount of suction force applied to lumen 22 of aspiration catheter 10 may more quickly and more effectively remove a thrombus from a blood vessel of a patient than applying a continuous or steady suction force. The amount of suction force generated by suction source 4 may be varied according to a particular suction frequency or other timing. In some examples, control circuitry 8 is configured to control the suction force applied by suction source 4 (FIG. 1A) or pump 5 (FIG. 1B) to catheter 10 by modifying the operation of suction source 4 to vary the suction force applied by suction source 4 to inner lumen 22 (e.g., by controlling the motor speed, or stroke length, volume or frequency, or other operating parameters, of suction source 4) and/or by operating, or controlling the state of, pulsator 7 (FIG. 1B), if present, positioned between pump 5 (or discharge reservoir 6, where present) and catheter 10. As discussed above, pulsator 7 can fluidically couple or uncouple the catheter 10 to or from the suction source 4 as needed. Pulsator 7 can comprise a valve, tubing clamp, tubing pincher, fluid switch, or the like, preferably configured for selective actuation as needed to fluidically couple or uncouple catheter 10 to or from pump 5 in accordance with control of aspiration system 2B.

Accordingly, in some examples, control circuitry 8 may first determine a suction frequency of suction source 4, and then determine the expansion frequency based on the suction frequency. For example, control circuitry 8 may determine the expansion frequency to be equivalent to or correlated with the suction frequency. In some examples, control circuitry 8 can determine the expansion frequency based on the suction frequency by at least selecting the expansion frequency to coordinate the time at which expandable member 18 is in its expanded configuration with the time at which suction source 4 is applying a relatively greatest suction force to lumen 22 and the time at which expandable member is in its contracted configuration (or a less expanded state) with the time at which suction source 4 is applying less suction force, such as no suction force or other suction force less than the relatively greatest suction force.

In some other examples in which control circuitry 8 varies an amount of suction force, but not according to any periodic suction frequency, control circuitry 8 may still correlate an expansion and contraction of expandable member 18 with a relative amount of suction force of suction source 4. For example, control circuitry 8 may vary the strength of the suction force or vacuum pressure of suction source 4 such that, as the vacuum pressure increases (e.g., via a user-input device and/or control circuitry 8), expandable member 18 expands by a proportional amount. For example, if during an aspiration procedure, suction source 4 cycles suction force between a minimum vacuum pressure and a maximum vacuum pressure, control circuitry 8 may control expandable member 18 to achieve an expanded configuration when the maximum vacuum pressure is applied. In other examples, expandable member 18 may be configured to remain in a contracted configuration until suction source 4 applies maximum vacuum pressure, at which time control circuitry 8 causes expandable member 18 to transition to a partially expanded or fully expanded configuration. In other examples, suction source 4 is configured to apply constant suction from to lumen 22 of catheter 10, in which case control circuitry 8 does not consider the frequency with which suction source 4 applies suction force to lumens 22, 25 when determining the expansion frequency.

Control circuitry 8 can determine the suction frequency using any suitable technique. Similar to a direct determination of the expansion frequency, control circuitry 8 may determine the suction frequency based on one or more of user input, a resonant frequency of a clot, a predetermined value stored in memory 9, or a cardiac cycle of a patient, as non-limiting examples.

For example, control circuitry 8 may determine the suction frequency by receiving user input via user-input device 20 or by retrieving the suction frequency from memory 9. The user input can, for example, indicate a quantitative or qualitative value for desired suction frequency. In some examples, control circuitry 8 is configured to receive user input selecting a suction frequency from a plurality of predetermined pump frequencies (e.g., stored by memory 9 of aspiration system 2A or a memory of another device).

In some examples, control circuitry 8 is configured to determine the suction frequency based on a cardiac cycle of a patient, using similar techniques to those described above with respect to determining an expansion frequency based on a cardiac cycle. Control circuitry 8 may then determine the expansion frequency of expandable member 18 based on based on the cardiac cycle of the patient, e.g., to coordinate the expanded and contracted configurations of expandable member 18 and the application of relatively high suction force and relatively low or no suction force with selected or predetermined parts of a cardiac cycle.

For example, after determining the cardiac cycle of the patient, control circuitry 8 may determine a suction frequency so as to control (e.g., strategically vary) a suction force of suction source 4 (e.g., via direct control of a pump, via controlling an associated pulsator 7 implemented as a valve, or fluid switch, or via other techniques of controlling suction source 4, as discussed herein) in accordance with the cardiac cycle. For example, control circuitry 8 can control suction source 4 to apply a first suction force to inner lumen 22 of catheter 10 during a first part of a cardiac cycle (e.g., diastole or systole) to generate a first suction force at mouth 13 of catheter 10, and control suction source 4 to apply a second suction force to inner lumen 22 during another part of the cardiac cycle (e.g., the other of diastole or systole) to generate a second suction force at mouth 13 of catheter 10, the first suction force being different from the second suction force. In some examples, the first suction force is greater than the second suction force. In other examples, the first suction force is less than the suction force.

For example, the first suction force or the second suction force can be zero such that suction source 4 does not actively apply any suction force to catheter 10 during the respective first or second part of the cardiac cycle. However, in some cases, even if suction source 4 is not actively applying a suction force to catheter 10, there may be some residual vacuum in inner lumen 22 of catheter 10 due to its length and the time required for the pressure in inner lumen 22 to equalize with the environment external to catheter 10 at mouth 13. Thus, even when suction source 4 is in an off-phase, in which suction source 4 is not actively operating to apply a suction force to catheter 10, a negative pressure in inner lumen 22 may still be observed. Thus, control circuitry 8 can be configured to cycle suction source 4 between an on-phase and an off-phase based on the cardiac cycle without causing the pressure differential between inner lumen 22 and the environment external to catheter 10 at mouth 13 to be zero.

In some examples, control circuitry 8 is configured to control suction source 4 to apply a suction force to lumen 22 of catheter 10, the applied suction force having a magnitude between a first suction force and a second suction force greater than the first suction force. For example, control circuitry 8 can be configured to control the suction force applied by suction source 4 to lumen 22 by at least controlling suction source 4 to cycle the suction force between the first and second suction forces according to a predetermined frequency or according to a cardiac cycle of a patient. The suction force range bounded by the first and second suction forces may be referred to as a suction force window. In some examples, the first suction force is 0 millimeters of mercury (mmHg). In some examples, control circuitry 8 controls suction source 4 to apply a greatest suction force of the suction force window to inner lumen 22 of catheter 10 during diastole. In these examples, control circuitry 8 may control suction source 4 to apply a lowest suction force of the suction force window to inner lumen 22 during systole or during another part of the cardiac cycle. Aligning a relatively highest (within the suction force window) suction force with diastole (e.g., between heart beats) may enable aspiration system 2A to apply a relatively greatest suction force to a thrombus when the blood vessel is relaxed and, therefore, may be less engaged with the thrombus.

In other examples, control circuitry 8 controls suction source 4 to apply a greatest suction force of the suction force window to inner lumen 22 (and/or controls expandable member 18 to reach its expanded state) of catheter 10 during systole. In these examples, control circuitry 8 may control suction source 4 to apply a lowest suction force of the suction force window to inner lumen 22 (and/or controls expandable member 18 to reach its expanded state) during diastole or during another part of the cardiac cycle. Aligning a relatively highest (within the suction force window) suction force (and/or a relatively most expanded state of expandable member 18) with diastole may enable aspiration system 2A to establish a greater pressure differential between inner lumen 22 of catheter 10 and the blood vessel, as the blood pressure within the blood vessel may be greater during systole than during diastole.

During a cardiac cycle, control circuitry 8 may cycle suction source 4 between the highest and lowest vacuum pressures of the suction force window at a frequency of about 0.5 Hertz (Hz) to about 5 Hz (e.g., within 5%, 10%, or 20% of these values), or from about 0.5 Hz to about 10 Hz, or to about 20 Hz. In examples in which the lower bound of the suction force window is 0 mmHg, suction source 4 can be considered to be in an off-phase at the lower bound of the suction force window and in an on-phase at the higher bound of the suction force window.

After determining the expansion frequency (160), control circuitry 8 controls the expansion and contraction of expandable member 18 based on the determined expansion frequency (162). For example, control circuitry 8 can cause expandable member 18 to transition between a fully contracted configuration and a fully expanded configuration, or between a fully contracted configuration and a partially expanded configuration, or between a partially contracted configuration and a partially expanded configuration, or between a partially contracted configuration and a fully expanded configuration, according to the determined expansion frequency. For example, once adjacent a target treatment site, expandable member 18 may be cyclically deployed from at least a partially contracted configuration (e.g., shown in FIGS. 2A, 3A, 3B, 5, 7, 9C, 9D, 11A, 12B) to at least a partially expanded configuration (e.g., shown in FIGS. 2B, 3C, 8B, 9A, 9B, 10A, 10B, 11B, and 12A) within the vasculature, under the control of control circuitry 8 (FIGS. 1 and 2A).

As an example, with reference to the examples of expandable member 18 discussed with reference to FIGS. 2A-6B, control circuitry 8 may control an actuation mechanism to proximally withdraw pull members 36 in order to radially bend a set of flexible prongs 34 and expand expandable member 18 to the expanded state of expandable member 18 and release the pull members 36 to return expandable member 18 to a contracted configuration, where the proximal withdrawal and release of the pull members 36 occurs according to the expansion frequency. In some examples, the actuation mechanism may include a relatively small battery and an electric motor contained within handle 14 (FIG. 2A). In some such examples, the electric motor is configured to drive a linear movement of pull members 36 back and forth along longitudinal axis 26.

Additionally or alternatively, control circuitry 8 may control the actuation mechanism to cycle, according to the expansion frequency, between proximally withdrawing pull members 36 in order to reorient two or more circumferential struts 56 of example expandable member 50 of FIGS. 7-8B and expand expandable member 50, and releasing the pull members 36 return expandable member 18 to a compressed state.

In addition to or instead of the examples including pull members 36 to expand and contract an expandable member, in some examples, control circuitry 8 may cyclically expand and contract an expandable member by at least deactivating magnetic device 74 in order to remove a magnetic attractive force acting upon a set of permanent magnetic strips 79 or magnetic material 78 of example expandable member 68 (FIGS. 9A-9D) and expandable member 70 (FIGS. 10A and 10B), according to the determined expansion frequency. Additionally or alternatively, control circuitry 8 may cyclically actuate magnetic device 74 in order to magnetically repel one or more permanent magnetic strips 81B of example expandable member 90 (FIGS. 11A and 11B), according to the determined expansion frequency. Additionally or alternatively, control circuitry 8 may cyclically proximally withdraw and distally insert magnet 107 in order to remove a magnetic attractive force acting upon body structure 77 of example expandable member 105 (FIGS. 12A and 12B) to cause expandable member 105 to expand radially outward, according to the determined expansion frequency. Additionally or alternatively, control circuitry 8 may cyclically distally insert and proximally withdraw magnet 107 in order to apply a magnetic repulsive force acting upon body structure 85 of example expandable member 110 (FIGS. 13A and 13B) to cause expandable member 110 to expand radially outward, according to the determined expansion frequency.

In examples in which the expansion frequency and/or the suction frequency are determined based on a cardiac cycle of a patient, control circuitry 8 can be configured to modify (e.g., vary) the amount of suction force present at mouth 13 of catheter 10 at various parts of the cardiac cycle by controlling the extent to which expandable member 18 is expanded at various parts of the cardiac cycle. For example, control circuitry 8 is configured to control expandable member 18 to expand to an expanded configuration during a first part of the cardiac cycle (e.g., to assume the expanded configuration during the first part of the cardiac cycle) and to control expandable member 18 to contract during a second part of the cardiac cycle different from the first part (e.g., to assume the contracted configuration during the second part of the cardiac cycle). As an example, the second part can correspond to diastole, such as, but not limited to, the start of diastole, a mid-point of diastole, or an end of diastole. As another example, the second part of the cardiac cycle can correspond to systole, such as, but not limited to, the start of systole, a mid-point of systole, or an end of systole. As yet another example, the second part of the cardiac cycle can correspond to a maximum ejection phase of the cardiac cycle (e.g., as indicated by an M-wave of a PQRST complex of an electrical cardiac signal). Other manners of controlling the cyclical expansion of expandable member 18 based on the cardiac cycle of a patient can be used in other examples.

As one example, control circuitry 8 may control expandable member 18 to contract or be in a fully or partially contracted configuration during systole or during another part of the cardiac cycle. Expanding expandable member 18 or causing expandable member to be in a partially or fully expanded configuration during diastole (e.g., between heart beats) may enable aspiration system 2A to apply a relatively greatest suction force to a thrombus when the blood vessel is relaxed and, therefore, may be less engaged with the thrombus.

In other examples, control circuitry 8 controls expandable member 18 to expand or be in a fully or partially expanded configuration during systole. In these examples, control circuitry 8 may control expandable member 18 to contract or be in a fully or partially contracted configuration during diastole or during another part of the cardiac cycle. Expanding expandable member 18 or causing expandable member to be in a partially or fully expanded configuration during diastole may enable aspiration system 2A to establish a greater pressure differential between inner lumen 22 of catheter 10 and the blood vessel, as the blood pressure within the blood vessel may be greater during systole than during diastole.

In some examples in which the expansion frequency is determined based on a suction frequency and/or an amount of suction force of suction source 4, control circuitry 8 may be configured to control the amount of suction force applied by suction source 4 and the cyclical expansion of expandable member 18 according to a common frequency, e.g., expandable member 18 is cyclically expanded in accordance with periodic higher-pressure "pulls" of suction source 4. In other examples, control circuitry 8 may cyclically expand and contract expandable member 18 while suction source 4 applies a substantially constant suction force (e.g., constant but for functionally negligible variations) to lumen 22 of catheter 10. In other examples, control circuitry 8 may be configured to independently control a suction frequency of suction source 4 and the expansion frequency of expandable member 18, wherein the suction frequency and the expansion frequency are either correlated or uncorrelated with one another. For example, the expansion frequency may be a multiple or a fraction of the suction frequency, or vice versa. In examples in which both the suction frequency and the expansion frequency are determined based on the cardiac cycle, control circuitry 8 may synchronize both the suction frequency and the expansion frequency with the cardiac cycle to cause suction source 4 to apply increased suction forces when expandable member 18 is in an expanded state, thereby more effectively removing a thrombus during an aspiration procedure.

In some examples, electrical energy may be applied to expandable member 18 to better engage the clot. For example, control circuitry 8 can control an energy source, e.g., of aspiration system 2A, to delivery an electrical energy to the exposed portions of expandable member 18 via one or more electrical conductors (not shown) electrically coupled to expandable member 18. The electrical conductors may be within lumen 22, external to elongated body 12, or embedded in elongated body 12. The electrical energy may be positively charged to electrostatically engage a clot. Characteristics of the electrical energy may be adjusted to better engage the clot, such as polarity, or an amount or type of current delivered. For example, pulsed direct current may be employed, optionally with a non-square and/or non-negative waveform.

In some examples, the technique of FIG. 16 further includes removing catheter 10 from the vasculature of the patient once the procedure is complete. For example, expandable member 18 may be collapsed into a contracted configuration as described above, and catheter 10 may be proximally withdrawn from the vasculature of the patient.

The techniques described in this disclosure, including those attributed to control circuitry 8, and sensing circuitry 11, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as clinician or patient programmers, medical devices, or other devices. Processing circuitry, control circuitry, and sensing circuitry, as well as other processors and controllers described herein, may be implemented at least in part as, or include, one or more executable applications, application modules, libraries, classes, methods, objects, routines, subroutines, firmware, and/or embedded code, for example. In addition, analog circuits, components and circuit elements may be employed to construct one, some or all of the control circuitry 8, and sensing circuitry 11, instead of or in addition to the partially or wholly digital hardware and/or software described herein. Accordingly, analog or digital hardware may be employed, or a combination of the two. Whether implemented in digital or analog form, or in a combination of the two, control circuitry 8 can comprise a timing circuit configured to command the expansion and contraction of expandable member 18, 50, 68, 70, 90 of a catheter according to a predetermined frequency, the application of a suction force (via, e.g., command of a pulsator in fluid communication with suction source 4) in synchrony with the patient's cardiac cycle or another predetermined frequency, or any combination thereof.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. The computer-readable medium may be an article of manufacture including a non-transitory computer-readable storage medium encoded with instructions. Instructions embedded or encoded in an article of manufacture including a non-transitory computer-readable storage medium encoded, may cause one or more programmable processors, or other processors, to implement one or more of the techniques described herein, such as when instructions included or encoded in the non-transitory computer-readable storage medium are executed by the one or more processors. Example non-transitory computer-readable storage media may include RAM, ROM, programmable ROM (PROM), erasable programmable ROM (EPROM), electronically erasable programmable ROM (EEPROM), flash memory, a hard disk, a compact disc ROM (CD-ROM), a floppy disk, a cassette, magnetic media, optical media, or any other computer readable storage devices or tangible computer readable media.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

The functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements.

The following clauses provide some examples of the disclosure.

Clause 1: In some examples, a catheter includes an elongated body defining an inner lumen and a central longitudinal axis, the elongated body including an expandable member at a distal portion of the elongated body, the expandable member including a plurality of prongs disposed around the central longitudinal axis; and a pull member coupled to at least one prong of the plurality of prongs, wherein the at least one prong is configured to expand radially outward relative to the central longitudinal axis in response to a tensile force applied to the pull member.

Clause 2: In some examples of the catheter of clause 1, the catheter further includes a plurality of pull members including the pull member, wherein each pull member of the plurality of pull members is coupled to a respective prong of the plurality of prongs, and wherein when the tensile force is applied to the plurality of pull members, the plurality of prongs expand radially outward to expand the expandable member radially outward.

Clause 3: In some examples of the catheter of clause 1 or clause 2, the expandable member includes a laser-cut nickel-titanium structure.

Clause 4: In some examples of the catheter of any of clauses 1-3, each prong includes a generally oval or flower-petal shape.

Clause 5: In some examples of the catheter of any of clauses 1-3, each prong includes a generally rectangular-prism shape.

Clause 6: In some examples of the catheter of any of clauses 1-5, the at least one prong includes one or more hinges configured to define a pivot point of the prong along which the prong bends in response to the tensile force from the pull member.

Clause 7: In some examples of the catheter of clause 6, each hinge includes one or more openings cut into a material of the respective prong.

Clause 8: In some examples of the catheter of clause 6 or clause 7, each prong includes two hinges.

Clause 9: In some examples of the catheter of any of clauses 6-8, each prong includes one hinge positioned at a proximal-most end of the expandable member.

Clause 10: In some examples of the catheter of any of clauses 1-9, the expandable member further includes a flexible membrane disposed over or under the prongs.

Clause 11: In some examples of the catheter of clause 9, the polymer includes a fluid-impermeable polymer.

Clause 12: In some examples of the catheter of any of clauses 1-11, the expandable member is mechanically coupled to the structural support member at a plurality of circumferential positions of the structural support member.

Clause 13: In some examples of the catheter of any of clauses 1-12, the elongated body defines an inner lumen, and wherein the expandable member defines a distal opening to the inner lumen.

Clause 14: In some examples of the catheter of any of clauses 1-13, an inner surface of the expandable member includes a plurality of engagement members configured to engage a thrombus.

Clause 15: In some examples of the catheter of any of clauses 1-14, the expandable member defines a tapered distal tip of the elongated body.

Clause 16: In some examples, a catheter includes an elongated body including a proximal portion and a distal portion; a handle coupled to the proximal portion of the elongated body; and an expandable member coupled to the distal portion of the elongated body, the expandable member including a plurality of flexible prongs disposed circumferentially around a central longitudinal axis of the catheter; and an elongated pull member defining a proximal pull end and a distal pull end, wherein: the distal pull end is rigidly coupled to at least one prong of the plurality of prongs; the proximal pull end is mechanically coupled to an actuator device on the handle; and the at least one prong is configured to expand radially outward from the central longitudinal axis in response to a tensile force applied via the pull member in response to actuation of the actuator device.

Clause 17: In some examples of the catheter of clause 16, the catheter further includes a plurality of pull members including the pull member, wherein each pull member of the plurality of pull members is coupled to a respective prong of the plurality of prongs, and wherein the tensile force is applied to the plurality of pull members, the plurality of prongs expand radially outward to expand the expandable member radially outward.

Clause 18: In some examples of the catheter of clause 16 or clause 17, the expandable member includes a laser-cut nickel titanium structure.

Clause 19: In some examples of the catheter of any of clauses 16-18, each prong includes a generally oval or flower-petal shape.

Clause 20: In some examples of the catheter of any of clauses 16-18, each prong includes a generally rectangular-prism shape.

Clause 21: In some examples, a method includes controlling, by control circuitry, an expandable member of a catheter to expand radially outward from a contracted configuration to an expanded configuration, wherein the expandable member includes a plurality of prongs disposed around the central longitudinal axis; and a pull member coupled to at least one prong of the plurality of prongs, wherein the at least one prong is configured to expand radially outward relative to the central longitudinal axis in response to a tensile force applied to the pull member; and controlling, by the control circuitry, the expandable member to contract radially inward from the expanded configuration to the contracted configuration.

Clause 22: In some examples of the method of clause 21, controlling the expandable member to expand radially outward includes controlling an actuation mechanism to apply the tensile force to the pull member.

Clause 23: In some examples of the method of clause 21 or clause 22, controlling the expandable member to contract radially inward includes controlling the actuation mechanism to release the tensile force applied to the pull member.

Clause 24: In some examples of the method of any of clauses 21-23, the method further includes receiving user input, wherein controlling the expandable member to expand radially outward includes controlling the expandable member to expand radially outward in response to receiving the user input.

Clause 25: In some examples of the method of any of clauses 21-24, controlling the expandable member includes controlling, by the control circuitry, the expandable member to move between the expanded configuration and the collapsed configuration based on a predetermined expansion frequency.

Clause 26: In some examples of the method of any of clauses 21-25, the catheter includes the catheter of any of clauses 1-20.

Clause 27: In some examples, a catheter includes an elongated body defining an inner lumen and a central longitudinal axis, the elongated body including an expandable member at a distal portion of the elongated body, the expandable member including a slidable leg configured to move proximally and distally along the central longitudinal axis; a first fixed leg; a second fixed leg, wherein the slidable leg is disposed between the first and second fixed legs; a strut having a first end hingedly connected to the slidable leg and a second end hingedly connected to the first fixed leg; and a second strut having a third end hingedly connected to the slidable leg and a fourth end hingedly connected to the second fixed leg, wherein a proximal motion of the slidable leg relative to the first and second fixed legs causes the first and second fixed legs to expand radially outward.

Clause 28: In some examples of the catheter of clause 27, a leg longitudinal axis of the slidable leg is parallel to the central longitudinal axis.

Clause 29: In some examples of the catheter of clause 27 or clause 28, the first strut and the second strut are configured to increase a width between the slidable leg and the respective first and second fixed legs in response to the proximal motion of the slidable leg.

Cause 30: In some examples of the catheter of any of clauses 27-29, the proximal motion of the slidable leg increases a strut angle between the slidable leg and the first and second struts.

Clause 31: In some examples of the catheter of any of clauses 27-30, the first and second struts are connected to the slidable leg by a respective first strut hinge and to the respective first and second fixed legs by a respective second strut hinge.

Clause 32: In some examples of the catheter of clause 31, each of the first strut hinge and the second strut hinge includes a C-shaped hinge configured to widen in response to the proximal motion of the slidable leg.

Clause 33: In some examples of the catheter of any of clauses 27-32, the catheter further includes a pull member coupled the slidable leg, the pull member configured to apply a proximal tensile force to the slidable leg to cause the proximal motion of the slidable leg.

Clause 34: In some examples of the catheter of any of clauses 27-33, the expandable member includes a plurality of slidable legs including the slidable leg; a plurality of struts including the first and second struts; and a plurality of fixed legs including the first and second fixed legs, wherein the fixed legs are disposed circumferentially around the central longitudinal axis, wherein the at least one slidable leg of the plurality of slidable legs is disposed between two fixed legs of the plurality of fixed legs and connected to the two fixed legs via respective struts of the plurality of struts.

Clause 35: In some examples of the catheter of clause 34, the plurality of struts defines a spiral pattern, wherein circumferentially adjacent struts are not longitudinally aligned.

Clause 36: In some examples of the catheter of clause 34 or clause 35, the plurality of slidable legs includes four to six slidable legs, and the plurality of fixed legs includes an equal number of fixed legs as slidable legs.

Clause 37: In some examples of the catheter of any of clauses 27-36, the expandable member includes a laser-cut nickel-titanium structure.

Clause 38: In some examples of the catheter of any of clauses 27-37, the expandable member further includes a flexible membrane disposed over or under the slidable leg and the first and second fixed legs.

Clause 39: In some examples of the catheter of clause 38, the membrane includes a fluid-impermeable polymer.

Clause 40: In some examples of the catheter of any of clauses 27-39, the elongated body defines an inner lumen, and the expandable member defines a distal opening to the inner lumen.

Clause 41: In some examples of the catheter of any of clauses 27-40, an inner surface of the expandable member includes a plurality of engagement members configured to engage with a thrombus.

Clause 42: In some examples of the catheter of any of clauses 27-41, the expandable member defines a tapered distal tip of the elongated body.

Clause 43: In some examples of the catheter of any of clauses 27-42, each of the first and second fixed legs includes one or more leg hinges positioned proximally from the first and second struts.

Clause 44: In some examples, a catheter includes an elongated body having a proximal portion and a distal portion; a handle coupled to the proximal portion of the elongated body; and an expandable member coupled to the distal portion of the elongated body, the expandable member including a slidable leg configured to move proximally and distally along the central longitudinal axis; a first fixed leg; a second fixed leg, wherein the slidable leg is disposed between the first and second fixed legs; and a strut having a first end hingedly connected to the slidable leg and a second end hingedly connected to the first fixed leg; and a second strut having a first end hingedly connected to the slidable leg and a second end hingedly connected to the second fixed leg, wherein a proximal motion of the slidable leg relative to the first and second fixed legs causes the first and second fixed legs to expand radially outward.

Clause 45: In some examples of the catheter of clause 44, the first and second struts are configured to increase a width between the slidable leg and the respective first and second fixed legs in response to the proximal motion of the slidable leg.

Clause 46: In some examples of the catheter of clause 44 or 45, the expandable member includes a laser-cut nickel-titanium structure.

Clause 47: In some examples, a method includes controlling, by control circuitry, an expandable member of a catheter to expand radially outward from a contracted configuration to an expanded configuration, wherein the expandable member includes a slidable leg configured to move proximally and distally along the central longitudinal axis; a first fixed leg; a second fixed leg, wherein the slidable leg is disposed between the first and second fixed legs; a strut having a first end hingedly connected to the slidable leg and a second end hingedly connected to the first fixed leg; and a second strut having a third end hingedly connected to the slidable leg and a fourth end hingedly connected to the second fixed leg, wherein a proximal motion of the slidable leg relative to the first and second fixed legs causes the first and second fixed legs to expand radially outward; and controlling, by the control circuitry, the expandable member to contract radially inward from the expanded configuration to the contracted configuration.

Clause 48: In some examples of the method of clause 47, controlling the expandable member to expand radially outward includes controlling an actuation mechanism to proximally move the slidable leg relative to the first and second fixed legs.

Clause 49: In some examples of the method of clause 47 or clause 48, the expandable member further includes a pull member coupled the slidable leg, wherein controlling the actuation mechanism to proximally move the slidable leg relative to the first and second fixed legs includes controlling the actuation mechanism to apply a proximal tensile force to the pull member.

Clause 50: In some examples of the method of any of clauses 47-49, controlling the expandable member to contract radially inward includes causing distal movement of the slidable leg relative to the first and second fixed legs.

Clause 51: In some examples of the method of any of clauses 47-50, the method further includes receiving user input, wherein controlling the expandable member to expand radially outward includes controlling the expandable member to expand radially outward in response to receiving the user input.

Clause 52: In some examples of the method of any of clauses 47-51, controlling the expandable member to includes controlling, by the control circuitry, the expandable member to move between the expanded configuration and the collapsed configuration based on a predetermined expansion frequency.

Clause 53: In some examples of the method of any of clauses 47-52, the catheter includes the catheter of any of clauses 27-46.

Clause 54: In some examples, a catheter includes an elongated body defining an inner lumen and including an expandable member at a distal portion of the elongated body, the expandable member including a body structure including a magnetic material, wherein the expandable member is configured to expand radially outward or contract radially inward in response to a magnetic force proximate the expandable member.

Clause 55: In some examples of the catheter of clause 54, the catheter further includes a magnetic device configured to generate the magnetic force.

Clause 56: In some examples of the catheter of clause 55, the magnetic device is fixed relative to the expandable member.

Clause 57: In some examples of the catheter of clause 55, the magnetic device is movable relative to the expandable member.

Clause 58: In some examples of the catheter of any of clauses 55-57, the magnetic device includes a permanent magnetic configured to generate the magnetic force.

Clause 59: In some examples of the catheter of any of clauses 55-57, the magnetic device includes a solenoid configured to generate the magnetic force when energy is applied to the solenoid.

Clause 60: In some examples of the catheter of clause 59, the solenoid includes a conductive wire wrapped around a nitinol rod.

Clause 61: In some examples of the catheter of any of clauses 54-60, the magnetic material includes one or more permanent magnetic strips extending along a central longitudinal axis of the elongated body and distributed circumferentially around the body structure.

Clause 62: In some examples of the catheter of clause 61, the magnetic force is a magnetic attractive force, and wherein the one or more permanent magnetic strips includes a plurality of magnetic strips having magnetic domains oriented to magnetically repel each other through a magnetic repulsive force, the catheter further including a magnetic device configured to generate the magnetic attractive force, wherein the magnetic device is configured to magnetically attract the plurality of magnetic strips through the magnetic attractive force, the magnetic attractive force being stronger than the magnetic repulsive force, such that the expandable member collapses into a contracted configuration when the magnetic device is applying the magnetic attractive force proximate to the expandable member.

Clause 63: In some examples of the catheter of clause 62, the magnetic repulsive force is configured to cause the expandable member to self-expand into an expanded configuration when the magnetic device is not applying the magnetic attractive force proximate to the expandable member.

Clause 64: In some examples of the catheter of clause 61, the magnetic force is a magnetic repulsive force, wherein the one or more permanent magnetic strips includes a first permanent magnetic strip and a second permanent magnetic strip, the first permanent magnetic strip being oriented to magnetically attract the second permanent through a magnetic attractive force, the catheter further including a magnetic device configured to generate the magnetic repulsive force, wherein the magnetic device is configured to magnetically repel the second permanent magnetic strip through the magnetic repulsive force, the magnetic repulsive force being greater than the magnetic attractive force, such that the expandable member expands into an expanded configuration when the magnetic device applies the magnetic force proximate to the expandable member.

Clause 65: In some examples of the catheter of any of clauses 54-64, the body structure defines a plurality of folds configured to guide a folding of the expandable member into a contracted configuration.

Clause 66: In some examples of the catheter of any of clauses 54-60, the catheter further includes a magnet configured to move into an inner lumen of the expandable member, wherein the magnet is configured to magnetically attract the magnetic material through the magnetic force to cause the expandable member to contract radially inwards.

Clause 67: In some examples of the catheter of clause 66, the catheter further includes a self-expanding structure disposed within the body structure, wherein the self-expanding structure is configured to apply an outward radial force to an interior surface of the body structure to expand the expandable member into an expanded configuration in the absence of the magnet in the inner lumen of the expandable member.

Clause 68: In some examples of the catheter of any of clauses 54-67, the magnetic material includes a ferromagnetic material embedded within the body structure.

Clause 69: In some examples of the catheter of clause 68, the ferromagnetic material includes iron particles.

Clause 70: In some examples of the catheter of any of clauses 54-69, the body structure includes a flexible polymer, and wherein the magnetic material includes discrete sections of magnetic material connected to the flexible polymer.

Clause 71: In some examples of the catheter of any of clauses 54-70, the body structure includes a flexible polymer and the magnetic material is embedded in the flexible polymer.

Clause 72: In some examples, an aspiration system includes a catheter defining a lumen terminating in a mouth, the catheter including an expandable member defining the mouth, wherein the expandable member includes a body structure including a magnetic material; and a magnetic device configured to apply a magnetic force proximate to the expandable member to cause the expandable member to expand radially outward or contract radially inward.

Clause 73: In some examples of the aspiration system of clause 72, the magnetic device is fixed relative to the expandable member.

Clause 74: In some examples of the aspiration system of clause 72, the magnetic device is movable relative to the expandable member.

Clause 75: In some examples of the aspiration system of any of clauses 72-74, the magnetic device includes a permanent magnetic configured to generate the magnetic force.

Clause 76: In some examples of the aspiration system of any of clauses 72-74, the magnetic device includes a solenoid configured to generate the magnetic force when energy is applied to the solenoid.

Clause 77: In some examples of the aspiration system of clause 76, the solenoid includes a conductive wire wrapped around a nitinol rod.

Clause 78: In some examples of the aspiration system of any of clauses 72-77, the magnetic material includes one or more permanent magnetic strips extending along a central longitudinal axis of the elongated body and distributed circumferentially around the body structure.

Clause 79: In some examples of the aspiration system of clause 78, the magnetic force is a magnetic attractive force, and wherein the one or more permanent magnetic strips includes a plurality of magnetic strips having magnetic domains oriented to magnetically repel each other through a magnetic repulsive force, wherein the magnetic device is configured to generate the magnetic attractive force, and wherein the magnetic device is configured to magnetically attract the plurality of magnetic strips through the magnetic attractive force, the magnetic attractive force being stronger than the magnetic repulsive force, such that the expandable member collapses into a contracted configuration when the magnetic device is applying the magnetic attractive force proximate to the expandable member.

Clause 80: In some examples of the aspiration system of clause 79, the magnetic repulsive force is configured to cause the expandable member to self-expand into an expanded configuration when the magnetic device is not applying the magnetic attractive force proximate to the expandable member.

Clause 81: In some examples of the aspiration system of clause 78, the magnetic force is a magnetic repulsive force, wherein the one or more permanent magnetic strips includes a first permanent magnetic strip and a second permanent magnetic strip, the first permanent magnetic strip being oriented to magnetically attract the second permanent through a magnetic attractive force, wherein the magnetic device is configured to generate the magnetic repulsive force, and wherein the magnetic device is configured to magnetically repel the second permanent magnetic strip through the magnetic repulsive force, the magnetic repulsive force being greater than the magnetic attractive force, such that the expandable member expands into an expanded configuration when the magnetic device applies the magnetic force proximate to the expandable member.

Clause 82: In some examples of the aspiration system of any of clauses 72-81, the body structure defines a plurality of folds configured to guide a folding of the expandable member into a contracted configuration.

Clause 83: In some examples of the aspiration system of any of clauses 72-82, the magnetic device includes a magnet configured to move into an inner lumen of the expandable member, wherein the magnet is configured to magnetically attract the magnetic material through the magnetic force to cause the expandable member to contract radially inwards.

Clause 84: In some examples of the aspiration system of clause 83, the catheter further includes a self-expanding structure disposed within the body structure, wherein the self-expanding structure is configured to apply an outward radial force to an interior surface of the body structure to expand the expandable member into an expanded configuration in the absence of the magnet in the inner lumen of the expandable member.

Clause 85: In some examples of the aspiration system of any of clauses 72-84, the magnetic material includes a ferromagnetic material embedded within the body structure.

Clause 86: In some examples of the aspiration system of clause 85, the ferromagnetic material includes iron particles.

Clause 87: In some examples of the aspiration system of any of clauses 72-86, the body structure includes a flexible polymer and the magnetic material includes discrete sections of magnetic material connected to the flexible polymer.

Clause 88: In some examples of the aspiration system of any of clauses 72-87, the body structure includes a flexible polymer and the magnetic material is embedded in the flexible polymer.

Clause 89: In some examples, a method includes controlling, by control circuitry, an expandable member of a catheter to expand radially outward from a contracted configuration to an expanded configuration, wherein the expandable member includes a body structure including a magnetic material, wherein the expandable member is configured to expand radially outward or contract radially inward in response to a magnetic force proximate the expandable member; and controlling, by the control circuitry, the expandable member to contract radially inward from the expanded configuration to the contracted configuration.

Clause 90: In some examples of the method of clause 89, controlling the expandable member to expand radially outward includes controlling a magnetic device to apply the magnetic force proximate the expandable member.

Clause 91: In some examples of the method of clause 89 or clause 90, the catheter comprises the catheter of any of clauses 1-18 or the aspiration system of any of clauses 19-35.

Clause 92: In some examples, an aspiration system includes a catheter including an elongated body defining an inner lumen; and an expandable member at a distal portion of the elongated body, wherein the expandable member is configured to expand radially outward from a contracted configuration to an expanded configuration; and control circuitry configured to control the expandable member to move between the expanded configuration and the contracted configuration based on the expansion frequency.

Clause 93: In some examples of the aspiration system of clause 92, the expanded configuration is a fully expanded configuration of the expandable member.

Clause 94: In some examples of the aspiration system of clause 92, the expanded configuration is a partially expanded configuration of the expandable member.

Clause 95: In some examples of the aspiration system of any of clauses 92-94, the contracted configuration is a fully contracted configuration of the expandable member.

Clause 96: In some examples of the aspiration system of any of clauses 92-94, the contracted configuration is a partially contracted configuration of the expandable member.

Clause 97: In some examples of the aspiration system of any of clauses 92-96, the system further includes a user input device, wherein the control circuitry is configured to receive, via the user input device, user input indicating the expansion frequency.

Clause 98: In some examples of the aspiration system of any of clauses 92-97, the control circuitry is configured to determine the expansion frequency.

Clause 99: In some examples of the aspiration system of clause 98, the control circuitry is configured to determine the expansion frequency based on a cardiac cycle of a patient.

Clause 100: In some examples of the aspiration system of clause 99, the control circuitry is configured to control the expandable member to expand radially outward from the contracted configuration to the expanded configuration according to the expansion frequency by at least controlling the expandable member to expand to the expanded configuration during a first part of the cardiac cycle and controlling the expandable member to contract to the contracted configuration during a second part of the cardiac cycle.

Clause 101: In some examples of the aspiration system of clause 98, the system further includes a suction source configured to apply a suction force to the catheter to remove fluid from the catheter, wherein the control circuitry is configured to determine the expansion frequency based on the suction force applied by the suction source to the catheter.

Clause 102: In some examples of the aspiration system of clause 101, the control circuitry is configured to control the suction source to cycle the suction force between first and second suction forces according to a suction frequency, and wherein the control circuitry is configured to determine the expansion frequency based on the suction frequency.

Clause 103: In some examples of the aspiration system of clause 101, the suction source is configured to apply a first suction force to the catheter and a second suction force to the catheter, wherein the control circuitry is configured to control the expandable member to expand radially outward from the contracted configuration to the expanded configuration according to the expansion frequency by at least controlling the expandable member to expand to the expanded configuration when the suction source is applying the first suction force to the catheter and controlling the expandable member to contract to the contracted configuration when the suction source is applying the second suction force to the catheter.

Clause 104: In some examples of the aspiration system of clause 101, the control circuitry is configured to control the suction force applied by the suction source to the catheter based on a cardiac cycle of a patient.

Clause 105: In some examples of the aspiration system of clause 98, the control circuitry is configured to determine the expansion frequency based on a resonant frequency of a thrombus.

Clause 106: In some examples of the aspiration system of any of clauses 98-104 or clause 104, the system further includes sensing circuitry configured to generate a signal indicative of a cardiac cycle of the patient or a resonant frequency of a thrombus in vasculature of a patient, wherein the control circuitry is configured to receive the signal from the sensing circuitry and determine the expansion frequency based on the signal.

Clause 107: In some examples of the aspiration system of clause 106, the signal includes at least one of an electrocardiogram, an electrogram, a photoplethysmogram, a transcranial doppler, or a blood pressure signal.

Clause 108: In some examples of the aspiration system of any of clauses 92-107, the expandable member includes a plurality of prongs disposed around the central longitudinal axis; and a pull member coupled to at least one prong of the plurality of prongs, wherein the at least one prong is configured to expand radially outward relative to the central longitudinal axis in response to a tensile force applied to the pull member, and wherein the control circuitry is configured to control the expandable member to move between the expanded configuration and the collapsed configuration based on the expansion frequency by at least controlling a timing with which an actuation mechanism applies the tensile force to the pull member based on the expansion frequency.

Clause 109: In some examples of the aspiration system of any of clauses 92-108, the expandable member includes a slidable leg configured to move proximally and distally along a longitudinal axis of the elongated body; a first fixed leg; a second fixed leg, wherein the slidable leg is disposed between the first and second fixed legs; a strut having a first end hingedly connected to the slidable leg and a second end hingedly connected to the first fixed leg; and a second strut having a third end hingedly connected to the slidable leg and a fourth end hingedly connected to the second fixed leg, wherein a proximal motion of the slidable leg relative to the first and second fixed legs causes the first and second fixed legs to expand radially outward, and wherein the control circuitry is configured to control the expandable member to move between the expanded configuration and the collapsed configuration based on the expansion frequency by at least controlling the slidable leg to move proximally and distally based on the expansion frequency.

Clause 110: In some examples of the aspiration system of any of clauses 92-109, the expandable member includes a magnetic material, the expandable member is configured to expand radially outward or contract radially inward in response to a magnetic force proximate the expandable member, and the control circuitry is configured to control the expandable member to move between the expanded configuration and the collapsed configuration based on the expansion frequency by at least controlling a timing with the magnetic force is applied to the expandable member.

Clause 111: In some examples of the aspiration system of clause 110, the control circuitry is configured to control the timing with which the magnetic force is applied to the expandable member by at least controlling movement of a magnet relative to the expandable member.

Clause 112: In some examples of the aspiration system of clause 110, the control circuitry is configured to control the timing with which the magnetic force is applied to the expandable member by at least controlling application of energy to a solenoid, the solenoid being configured to generate the magnetic force.

Clause 113: In some examples of the aspiration system of any of clauses 92-113, the control circuitry is configured to control the expandable member to move between the expanded configuration and the collapsed configuration based on the expansion frequency by at least controlling the number of times the expandable member is in the expanded configuration per unit of time based on the expansion frequency.

Clause 114: In some examples, an aspiration system includes a suction source configured to apply a suction force to a catheter to remove fluid from the catheter during a medical aspiration procedure; and control circuitry configured to control an expandable member of the catheter to expand and contract during the medical aspiration procedure.

Clause 115: In some examples of the aspiration system of clause 114, the control circuitry is configured to control the expandable member to expand and contract by at least controlling when the expandable member is in a contracted configuration and when the expandable member is in an expanded configuration based on an expansion frequency.

Clause 116: In some examples of the aspiration system of clause 115, the expanded configuration is a fully expanded configuration or a partially expanded configuration of the expandable member.

Clause 117: In some examples of the aspiration system of clause 115 or clause 116, wherein the contracted configuration is a fully contracted configuration or a partially contracted configuration of the expandable member.

Clause 118: In some examples of the aspiration system of any of clauses 115-117, further including a user input device, wherein the control circuitry is configured to receive, via the user input device, user input indicating the expansion frequency.

Clause 119: In some examples of the aspiration system of any of clauses 115-117, wherein the control circuitry is configured to determine the expansion frequency.

Clause 120: In some examples of the aspiration system of any of clauses 115-119, further including sensing circuitry configured to generate a signal indicative of a cardiac cycle of the patient or a resonant frequency of a thrombus in vasculature of a patient, wherein the control circuitry is configured to determine the expansion frequency based on the signal.

Clause 121: In some examples of the aspiration system of any of clauses 115-120, the control circuitry is configured to determine the expansion frequency based on a suction force applied by the suction source to the catheter.

Clause 122: In some examples of the aspiration system of any of clauses 115-121, the control circuitry is configured to determine the expansion frequency based a resonant frequency of a thrombus.

Clause 123: In some examples of the aspiration system of any of clauses 115-120, the system further includes sensing circuitry configured to generate a signal indicative of a cardiac cycle of the patient or a resonant frequency of a thrombus in vasculature of a patient, wherein the control circuitry is configured to determine the expansion frequency based on the signal from the sensing circuitry.

Clause 124: In some examples, a method includes determining, by control circuitry, an expansion frequency for an expandable member of a catheter, the catheter including an elongated body defining an inner lumen; and the expandable member at the distal portion of the elongated body, wherein the expandable member is configured to expand radially outward from a contracted configuration to an expanded configuration; and controlling, by the control circuitry, the expandable member to move between the expanded configuration and the collapsed configuration based on the expansion frequency.

Clause 125: In some examples of the method of clause 124, the expanded configuration is a fully expanded configuration or a partially expanded configuration of the expandable member.

Clause 126: In some examples of the method of clause 124 or clause 125, the collapsed configuration is a fully collapsed configuration or a partially collapsed configuration of the expandable member.

Clause 127: In some examples of the method of any of clauses 124-126, controlling the expandable member to move between the expanded configuration and the collapsed configuration based on the expansion frequency includes controlling the number of times the expandable member is in the expanded configuration per unit of time based on the expansion frequency.

Clause 128: In some examples of the method of any of clauses 124-127, determining the expansion frequency includes receiving, via a user input device, user input indicating the expansion frequency.

Clause 129: In some examples of the method of any of clauses 124-127, determining the expansion frequency includes determining, by the control circuitry, the expansion frequency based on a cardiac cycle of a patient.

Clause 130: In some examples of the method of clause 129, controlling the expandable member to move between the expanded configuration and the collapsed configuration based on the expansion frequency includes controlling the expandable member to expand to the expanded configuration during a first part of the cardiac cycle and controlling the expandable member to contract to the contracted configuration during a second part of the cardiac cycle.

Clause 131: In some examples of the method of any of clauses 124-128, wherein determining the expansion frequency includes determining, by the control circuitry, the expansion frequency based on a suction force applied by a suction source to the catheter.

Clause 132: In some examples of the method of any of clauses 124-128, the method further includes controlling, by the control circuitry, the suction source to cycle the suction force between first and second suction forces according to a suction frequency, and wherein determining the expansion frequency includes determining the expansion frequency based on the suction frequency.

Clause 133: In some examples of the method of any of clauses 124-128, the method further includes controlling, by the control circuitry, the suction force applied by the suction source to the catheter based on a cardiac cycle of a patient.

Clause 134: In some examples of the method of any of clauses 124-128, determining the expansion frequency includes determining, by the control circuitry, the expansion frequency based on a resonant frequency of a thrombus.

Clause 135: In some examples of the method of any of clauses 124-134, the method further including generating, by sensing circuitry, a signal indicative of a cardiac cycle of the patient or a natural frequency of a thrombus in vasculature of a patient, wherein determining the expansion frequency includes determining, by the control circuitry, the expansion frequency based on the signal from the sensing circuitry.

Clause 136: In some examples of the method of clause 135, the signal includes at least one of an electrocardiogram, an electrogram, a photoplethysmogram, or a blood pressure signal.

Clause 137: In some examples of the method of any of clauses 124-136, the expandable member includes a plurality of prongs disposed around the central longitudinal axis; and a pull member coupled to at least one prong of the plurality of prongs, wherein the at least one prong is configured to expand radially outward relative to the central longitudinal axis in response to a tensile force applied to the pull member, and wherein controlling the expandable member to move between the expanded configuration and the collapsed configuration based on the expansion frequency includes controlling an actuation mechanism to apply the tensile force to the pull member based on the expansion frequency.

Clause 138: In some examples of the method of any of clauses 124-137, the expandable member includes a slidable leg configured to move proximally and distally along a longitudinal axis of the elongated body; a first fixed leg; a second fixed leg, wherein the slidable leg is disposed between the first and second fixed legs; a strut having a first end hingedly connected to the slidable leg and a second end hingedly connected to the first fixed leg; and a second strut having a third end hingedly connected to the slidable leg and a fourth end hingedly connected to the second fixed leg, wherein a proximal motion of the slidable leg relative to the first and second fixed legs causes the first and second fixed legs to expand radially outward, and wherein controlling the expandable member to move between the expanded configuration and the collapsed configuration based on the expansion frequency includes controlling the slidable leg to move proximally and distally based on the expansion frequency.

Clause 139: In some examples of the method of any of clauses 124-138, the expandable member includes a magnetic material, wherein the expandable member is configured to expand radially outward or contract radially inward in response to a magnetic force proximate the expandable member, and wherein controlling the expandable member to move between the expanded configuration and the collapsed configuration based on the expansion frequency includes controlling a timing with the magnetic force is applied to the expandable member.

Clause 140: In some examples of the method of clause 139, controlling the timing with which the magnetic force is applied to the expandable member includes controlling, by the control circuitry, movement of a magnet relative to the expandable member.

Clause 141: In some examples of the method of clause 139, controlling the timing with which the magnetic force is applied to the expandable member includes controlling application of energy to a solenoid, the solenoid being configured to generate the magnetic force.

Clause 142: The method of any of clauses 124-141, wherein the catheter includes the catheter of any of clauses 92-123 and/or wherein the control circuitry includes the control circuitry of any of clauses 92-123.

The examples described herein may be combined in any permutation or combination.

Various aspects of the disclosure have been described. These and other aspects are within the scope of the following claims.

What is claimed is:

1. An aspiration system comprising:
a catheter including:
an elongated body defining an inner lumen; and
an expandable member at a distal portion of the elongated body, wherein the expandable member includes a radially expandable mouth, wherein the radially expandable mouth is configured to expand radially outward from a contracted configuration to an expanded configuration to physically engage a clot; and
control circuitry configured to control the expandable mouth to move between the expanded configuration and the contracted configuration based on an expansion frequency.

2. The aspiration system of claim 1, wherein the expanded configuration is a fully expanded configuration of the expandable mouth.

3. The aspiration system of claim 1, wherein the expanded configuration is a partially expanded configuration of the expandable mouth.

4. The aspiration system of claim 1, wherein the contracted configuration is a fully contracted configuration of the expandable mouth.

5. The aspiration system of claim 1, wherein the contracted configuration is a partially contracted configuration of the expandable mouth.

6. The aspiration system of claim 1, wherein the control circuitry is configured to determine the expansion frequency based on a cardiac cycle of a patient.

7. The aspiration system of claim 6, wherein the control circuitry is configured to control the expandable mouth to expand radially outward from the contracted configuration to the expanded configuration according to the expansion frequency by at least controlling the expandable mouth to expand to the expanded configuration during a first part of the cardiac cycle and controlling the expandable mouth to contract to the contracted configuration during a second part of the cardiac cycle.

8. The aspiration system of claim 1, wherein the control circuitry is configured to determine the expansion frequency based on a signal indicative of one or more sensed physiological parameters.

9. The aspiration system of claim 1, wherein the expandable mouth is configured to expand radially outward from the contracted configuration to the expanded configuration in response to one or more control signals from the control circuitry.

10. An aspiration system comprising:

a suction source configured to apply a suction force to a catheter to remove fluid from the catheter during a medical aspiration procedure; and control circuitry configured to control a radially expandable mouth of the catheter to expand and contract during the medical aspiration procedure to physically engage a clot.

11. The aspiration system of claim 10, wherein the control circuitry is configured to control the expandable mouth to expand and contract by at least controlling when the expandable mouth is in a contracted configuration and when the expandable mouth is in an expanded configuration based on an expansion frequency.

12. The aspiration system of claim 11, wherein the expanded configuration is a fully expanded configuration or a partially expanded configuration of the expandable mouth, and wherein the contracted configuration is a fully contracted configuration or a partially contracted configuration of the expandable mouth.

13. The aspiration system of claim 11, wherein the control circuitry is configured to determine the expansion frequency based on a cardiac cycle of a patient.

14. The aspiration system of claim 11, wherein the control circuitry is configured to determine the expansion frequency based on a signal indicative of one or more sensed physiological parameters.

15. An aspiration system comprising:

a catheter defining an inner lumen, the catheter comprising a radially expandable mouth defining a distal opening to the inner lumen, wherein the expandable mouth is configured to physically engage a clot;

sensing circuitry configured to generate a signal indicative of one or more sensed physiological parameters; and control circuitry configured to:

determine an expansion frequency based on the signal; and control the expandable mouth to expand and contract according to the expansion frequency.

16. The aspiration system of claim 15, wherein the control circuitry is configured to determine the expansion frequency based on a cardiac cycle of a patient.

\* \* \* \* \*